United States Patent
Sparre-Ulrich et al.

(10) Patent No.: US 10,968,266 B2
(45) Date of Patent: Apr. 6, 2021

(54) GIP PEPTIDE ANALOGUES

(71) Applicant: University of Copenhagen, Copenhagen K (DK)

(72) Inventors: Alexander Hovard Sparre-Ulrich, Copenhagen N (DK); Mette Marie Rosenkilde, Hellerup (DK); Jens Juul Holst, Hellerup (DK); Filip Krag Knop, Hellerup (DK); Mikkel Bring Christensen, Brønshøj (DK); Lærke Smidt Gasbjerg, Vanløse (DK)

(73) Assignee: UNIVERSITY OF COPENHAGEN, Copenhagen K (DK)

( * ) Notice: Subject to any disclaimer, the term of this patent is extended or adjusted under 35 U.S.C. 154(b) by 0 days.

(21) Appl. No.: 15/508,037

(22) PCT Filed: Sep. 7, 2015

(86) PCT No.: PCT/DK2015/050266
§ 371 (c)(1),
(2) Date: Mar. 1, 2017

(87) PCT Pub. No.: WO2016/034186
PCT Pub. Date: Mar. 10, 2016

(65) Prior Publication Data
US 2018/0258152 A1    Sep. 13, 2018

(30) Foreign Application Priority Data
Sep. 5, 2014 (DK) .............. PA201470545

(51) Int. Cl.
| | | |
|---|---|---|
| *C07K 14/605* | (2006.01) | |
| *A61K 38/26* | (2006.01) | |
| *A61K 38/00* | (2006.01) | |
| *A61P 3/00* | (2006.01) | |
| *A61P 5/00* | (2006.01) | |

(52) U.S. Cl.
CPC ............ *C07K 14/605* (2013.01); *A61K 38/26* (2013.01); *A61K 38/00* (2013.01); *A61P 3/00* (2018.01); *A61P 5/00* (2018.01)

(58) Field of Classification Search
CPC ...... A61K 38/00; A61K 38/26; C07K 14/605; A61P 3/00; A61P 5/00
See application file for complete search history.

(56) References Cited

U.S. PATENT DOCUMENTS

| | | |
|---|---|---|
| 6,004,297 A | 12/1999 | Steenfeldt-Jensen et al. |
| 6,268,343 B1 | 7/2001 | Knudsen et al. |
| 6,384,016 B1 | 5/2002 | Kaarsholm |
| 6,410,508 B1 | 6/2002 | Isales et al. |
| 6,458,924 B2 | 10/2002 | Knudsen et al. |
| 7,326,688 B2 | 2/2008 | O'Harte et al. |
| 7,875,587 B2 | 1/2011 | Gault et al. |
| 8,450,266 B2 | 5/2013 | Dong et al. |
| 9,072,703 B2 | 7/2015 | Dong |
| 2001/0011071 A1 | 8/2001 | Knudsen et al. |
| 2005/0059605 A1* | 3/2005 | Peri ............ C07K 14/575 514/7.3 |
| 2005/0272652 A1 | 12/2005 | Gault et al. |
| 2007/0167370 A1 | 7/2007 | Gault et al. |
| 2008/0009603 A1 | 1/2008 | Gault et al. |
| 2008/0312157 A1 | 12/2008 | Levy et al. |
| 2014/0162945 A1* | 6/2014 | Ma ............. C07K 14/605 514/5.3 |
| 2019/0330332 A1 | 10/2019 | Okahara et al. |
| 2019/0330333 A1 | 10/2019 | Okahara et al. |
| 2019/0330334 A1 | 10/2019 | Okahara et al. |

FOREIGN PATENT DOCUMENTS

| | | |
|---|---|---|
| EP | 3560514 A1 | 10/2019 |
| EP | 3560515 A1 | 10/2019 |
| EP | 3569248 A1 | 11/2019 |
| WO | WO-1996/29342 A1 | 9/1996 |
| WO | WO-1998/08871 A1 | 3/1998 |
| WO | 1998/24464 A1 | 6/1998 |
| WO | 1999/43708 A1 | 9/1999 |
| WO | 2000/20592 A1 | 4/2000 |
| WO | 2000/34331 A2 | 6/2000 |
| WO | 2000/58360 A2 | 10/2000 |
| WO | 200246227 A2 | 6/2002 |
| WO | 2003082898 A2 | 10/2003 |
| WO | 2004067548 A2 | 8/2004 |
| WO | 2006086769 A2 | 8/2006 |
| WO | 2006097537 A2 | 9/2006 |
| WO | 2007109354 A2 | 9/2007 |
| WO | 2010016935 A2 | 2/2010 |
| WO | 2010016936 A1 | 2/2010 |
| WO | 2010016938 A2 | 2/2010 |

(Continued)

OTHER PUBLICATIONS

Health line (Nutrition and Metabolism Disorders, http://www.healthline.com/health/nutrition-metabolism-disorders, accessed on Jan. 28, 2019).*

Gault, Characterisation and biological activity of Glu3 amino acid substituted GIP receptor antagonists, Archives of Biochemistry and Biophysics 461 (2007) 263-274.*

RA Perry, Characterisation of Glucose-Dependent Insulinotropic Polypeptide Receptor Antagonists in Rodent Pancreatic Beta Cells and Mice, Clinical Medicine Insights: Endocrinology and Diabetes, 2019.*

(Continued)

*Primary Examiner* — James H Alstrum-Acevedo
*Assistant Examiner* — Erinne R Dabkowski

(57) ABSTRACT

Provided herein are glucose-dependent insulinotropic polypeptide (GIP)-derived peptide analogues, for example GIP (3-30), and their use as antagonists of the GIP receptor and for treatment of disorders such as obesity, diabetes mellitus and insulin resistance.

18 Claims, 9 Drawing Sheets
Specification includes a Sequence Listing.

(56) References Cited

FOREIGN PATENT DOCUMENTS

| WO | 2010016940 A2 | 2/2010 |
|---|---|---|
| WO | 2010016944 A2 | 2/2010 |
| WO | 2012055770 A1 | 5/2012 |
| WO | WO-2012/088379 A2 | 6/2012 |
| WO | 2012167744 A1 | 12/2012 |
| WO | 2016034186 A1 | 3/2016 |
| WO | WO-2016/066744 A2 | 5/2016 |
| WO | 2016205488 A1 | 12/2016 |
| WO | WO-2018/220123 A1 | 12/2018 |

OTHER PUBLICATIONS

Ravn et al. Structural and Pharmacological Characterization of Novel Potent and Selective Monoclonal Antibody Antagonists of Glucose-dependent Insulinotropic Polypeptide Receptor.Journal of Biological Chemistry (2013), 288 (27), 19760-19772.

Rosenkilde et al. Mutations along transmembrane segment II of the NK-1 receptor affect substance P competition with non-peptide antagonists but not substance P binding. Journal of Biological Chemistry. J Biol Chem (1994), 269, 28160-28164.

Sauber J, Grothe J, Behm M, Scherag A, Grallert H, Illig T, et al. Association of variants in gastric inhibitory polypeptide receptor gene with impaired glucose homeostasis in obese children and adolescents from Berlin. European journal of endocrinology. 2010;163(2):259-64.

Song et al. Glucose-Dependent Insulinotropic Polypeptide Enhances Adipocyte Development and Glucose Uptake in Part Through Akt Activation. Gastroenterology (2007), 133(6), 1796-1805.

Sparre-Ulrich AH, Gabe MN, Gasbjerg LS, Christiansen CB, Svendsen B, Hartmann B, et al. GIP(3-30)NH2 is a potent competitive antagonist of the GIP receptor and effectively inhibits GIP-mediated insulin, glucagon, and somatostatin release. Biochemical pharmacology. 2017;131:78-88.

Starich et al. GIP increases insulin receptor affinity and cellular sensitivity in adipocytes. Am J Physiol (1985), 249(6 Pt 1), E603-E607.

Tseng et al. Postprandial stimulation of insulin release by glucose-dependent insulinotropic polypeptide (GIP). Effect of a specific glucose-dependent insulinotropic polypeptide receptor antagonist in the rat. J Clin Invest (1996), 98(11), 2440-2445.

Widenmaier et al. . A GIP Receptor Agonist Exhibits beta-Cell Anti-Apoptotic Actions in Rat Models of Diabetes Resulting in Improved beta-Cell Function and Glycemic Control.PLoS One (2010), 5(3), e9590.

Adrian et al. Pancreatic polypeptide, glucagon and insulin secretion from the isolated perfused canine pancreas. Diabetologia (1978), 14(6), 413-417.

Ahlqvist et al. Link Between GIP and Osteopontin in Adipose Tissue and Insulin Resistance.Diabetes (2013), 62(6), 2088-2094.

Asmar et al. Glucose-Dependent Insulinotropic Polypeptide May Enhance Fatty Acid Re-esterification in Subcutaneous Abdominal Adipose Tissue in Lean Humans. Diabetes (2010), 59(9), 2160-2163.

Baggio et al. Biology of Incretins: GLP-1 and GIP. Gastroenterology (2007), 132(6), 2131-2157.

Brunicardi et al. Selective neurohormonal interactions in islet cell secretion in the isolated perfused human pancreas. Journal of Surgical Research (1990), 48(4), 273-278.

Brons et al. Impact of short-term high-fat feeding on glucose and insulin metabolism in young healthy men. The Journal of Physiology (2009), 587(10), 2387-2397.

Calanna et al. Secretion of Glucose-Dependent Insulinotropic Polypeptide in Patients With Type 2 Diabetes: Systematic review and meta-analysis of clinical studies. Diabetes Care (2013), 36(10), 3346-3352.

Christensen et al. Glucose-Dependent Insulinotropic Polypeptide Augments Glucagon Responses to Hypoglycemia in Type 1 Diabetes. Diabetes. Jan. 2015;64(1):72-8. Epub Jul. 22, 2014.

Christensen et al. Glucose-Dependent Insulinotropic Polypeptide: A Bifunctional Glucose-Dependent Regulator of Glucagon and Insulin Secretion in Humans. Diabetes (2011), 60(12), 3103-3109.

Christensen et al. Glucose-dependent Insulinotropic Polypeptide: Blood Glucose Stabilizing Effects in Patients With Type 2 Diabetes. J Clin Endocrinol Metab. Mar. 2014;99(3):E418-26. Epub Dec. 11, 2013.

Deacon et al. GIP-(3-42) does not antagonize insulinotropic effects of GIP at physiological concentrations. American Journal of Physiology—Endocrinology and Metabolism (2006), 291(3), E468-475.

Deblasi et al. Calculating receptor number from binding experiments using same compound as radioligand and competitor. Trends in Pharmacological Sciences (1989), 10, 227-229.

Deschamps et al. Effects of diet on insulin and gastric inhibitory polypeptide levels in obese children. Pediatr Res (1980), 14(4 Pt 1), 300-303.

Ding et al. Glucagon-like peptide I and glucose-dependent insulinotropic polypeptide stimulate Ca2+-induced secretion in rat alpha-cells by a protein kinase A-mediated mechanism. Diabetes (1997), 46(5), 792-800.

Dupre J et al., Stimulation of Glucagon Secretion by Gastric Inhibitory Polypeptide in Patients with Hepatic Cirrhosis and Hyperglucagonemia. The Journal of Clinical Endocrinology & Metabolism 1991;72(1):125-129.

Ebert et al. Release of gastric inhibitory polypeptide (GIP) by intraduodenal acidification in rats and humans and abolishment of the incretin effect of acid by GIP-antiserum in rats. Gastroenterology (1979), 76(3), 515-523.

Fujita et al. Differential processing of pro-glucose-dependent insulinotropic polypeptide in gut. American Journal of Physiology—Gastrointestinal and Liver Physiology (2010), 298(5):G608-G14.

Fulurija et al. Vaccination against GIP for the Treatment of Obesity. PLoS One (2008), 3(9), e3163.

Gault et al. Characterization of the Cellular and Metabolic Effects of a Novel Enzyme-Resistant Antagonist of Glucose-Dependent Insulinotropic Polypeptide. Biochemical and Biophysical Research Communications (2002), 290(5):1420-1426.

Gelling et al. GIP(6-30amide) contains the high affinity binding region of GIP and is a potent inhibitor of GIP1-42 action in vitro. Regulatory Peptides (1997), 69(3), 151-154.

Getty-Kaushik et al. Glucose-Dependent Insulinotropic Polypeptide Modulates Adipocyte Lipolysis and Reesterification. Obesity (2006), 14(7), 1124-1131.

Goetze et al. Peptide hormones and their prohormones as biomarkers. Biomarkers Med (2009), 3(4), 335-338.

Goetze et al. Processing-independent analysis of peptide hormones and prohormones in plasma.Front Biosci (2012), 17, 1804-1815.

Graham et al. A new technique for the assay of infectivity of human adenovirus 5 DNA. Virology (1973), 52(2), 456-467.

Gutniak et al. Antidiabetogenic Effect of Glucagon-like Peptide-1 (7-36)amide in Normal Subjects and Patients with Diabetes Mellitus. N Engl J Med (1992), 326(20), 1316-1322.

Hansen et al., N-terminally and C-terminally truncated forms of glucose-dependent insulinotropic polypeptide are high-affinity competitive antagonists of the human GIP receptor. British Journal of Pharmacology (2016) 173(5): 826-838.

Hauner et al. Effects of gastric inhibitory polypeptide on glucose and lipid metabolism of isolated rat adipocytes. Ann Nutr Metab (1988), 32(5-6), 282-288.

Heer et al. Glucagon-like peptide-1, but not glucose-dependent insulinotropic peptide, inhibits glucagon secretion via somatostatin (receptor subtype 2) in the perfused rat pancreas. Diabetologia (2008), 51(12), 2263-2270.

Hinke et al. Identification of a bioactive domain in the amino-terminus of glucose-dependent insulinotropic polypeptide (GIP). Biochimica et Biophysica Acta (BBA)—Protein Structure and Molecular Enzymology (2001), 1547(1), 143-155.

Hinke et al. Structure-Activity Relationships of Glucose-Dependent Insulinotropic Polypeptide (GIP). Biological Chemistry (2003), 384(3), 403-407.

Hinke et al., In depth analysis of the N-terminal bioactive domain of gastric inhibitory polypeptide. Life Sciences (2004) 75(15): 1857-1870.

(56) References Cited

OTHER PUBLICATIONS

Holst JJ. On the Physiology of GIP and GLP-1. Horm Metab Res (2004), 36(11/12), 747-754.
Holst, J. J. & Bersani, M., 1—Assays for Peptide Products of Somatostatin Gene Expression. In: Conn, P. M.(ed.) Methods in Neurosciences. Academic Press; 1991, p. 3-22.
Hoejberg et al. Four weeks of near-normalisation of blood glucose improves the insulin response to glucagon-like peptide-1 and glucose-dependent insulinotropic polypeptide in patients with type 2 diabetes. Diabetologia (2009), 52(2), 199-207.
Irwin et al. Active immunisation against gastric inhibitory polypeptide (GIP) improves blood glucose control in an animal model of obesity-diabetes. Biological Chemistry, (2009), 390(1), 75-80.
Irwin et al. Biological activity and antidiabetic potential of synthetic fragment peptides of glucose-dependent insulinotropic polypeptide, GIP(1-16) and (Pro3)GIP(1-16). Regulatory Peptides (2006), 135(1-2), 45-53.
Jorgensen et al. Exaggerated Glucagon-Like Peptide 1 Response Is Important for Improved β-Cell Function and Glucose Tolerance After Roux-en-Y Gastric Bypass in Patients With Type 2 Diabetes. Diabetes (2013), 62(9), 3044-3052.
Kerr et al. Characterization and biological actions of N-terminal truncated forms of glucose-dependent insulinotropic polypeptide. Biochemical and Biophysical Research Communications (2011), 404(3), 870-876.
Kim et al. GIP-Overexpressing Mice Demonstrate Reduced Diet-Induced Obesity and Steatosis, and Improved Glucose Homeostasis. PLoS ONE (2012), 7(7), e40156.
Kissow et al. Glucagon-like peptide-1 (GLP-1) receptor agonism or DPP-4 inhibition does not accelerate neoplasia in carcinogen treated mice. Regulatory Peptides (2012), 179 (1-3), 91-100.
Lazareno et al. Estimation of competitive antagonist affinity from functional inhibition curves using the Gaddum, Schild and Cheng-Prusoff equations. Br J Pharmacol, (1993) 109(4), 1110-1119.
Martin et al. A novel acylated form of (d-Ala(2))GIP with improved antidiabetic potential, lacking effect on body fat stores. Biochimica et Biophysica Acta, (2013), 1830(6), 3407-3413.
Meier et al. Gastric inhibitory polypeptide (GIP) dose-dependently stimulates glucagon secretion in healthy human subjects at euglycaemia. Diabetologia (2003), 46(6), 798-801.
Miyawaki et al. Glucose intolerance caused by a defect in the entero-insular axis: A study in gastric inhibitory polypeptide receptor knockout mice. Proceedings of the National Academy of Sciences (1999), 96(26), 14843-14847.
Miyawaki et al. Inhibition of gastric inhibitory polypeptide signaling prevents obesity. Nat Med (2002), 8(7), 738-742.
Nakamura et al. Biological and functional characteristics of a novel low-molecular weight antagonist of glucose-dependent insulinotropic polypeptide receptor, SKL-14959, in vitro and in vivo. Diabetes, Obesity and Metabolism (2012), 14(6), 511-517.
Nasteska et al. Chronic Reduction of GIP Secretion Alleviates Obesity and Insulin Resistance Under High-Fat Diet Conditions. Diabetes (2014), 63(7), 2332-2343.
Pathak et al. Antagonism of gastric inhibitory polypeptide (GIP) by palmitoylation of GIP analogues with N- and C-terminal modifications improves obesity and metabolic control in high fat fed mice. Molecular and Cellular Endocrinology (2015), 401(5), 120-129.
Pederson et al. Interaction of Gastric Inhibitory Polypeptide, Glucose, and Arginine on Insulin and Glucagon Secretion from the Perfused Rat Pancreas. Endocrinology (1978), 103(2), 610-615.
Raufman et al. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry (1991), 266(5), 2897-2902.
Irwin, N. et al.: "GIP(Lys$^{16}$PAL) and GIP(Lys$^{37}$PAL): Novel Long-Acting Acylated Analogues of Glucose-Dependent Insulinotropic Polypeptide with Improved Antidiabetic Potential", Journal of Medicinal Chemistry, 49(3):1047-1054, 2006.
Pathak, V. et al.: "Sequential induction of beta cell rest and stimulation using stable GIP inhibitor and GLP-1 mimetic peptides improves metabolic control in C57BL/KsJ db/db mice", Diabetologica, 58(9),2144-2153, 2015.
Gault, V. et al., Evidence that the major degradation product of glucose-dependent insulinotropic polypeptide, GIP(3-42), is a GIP receptor antagonist in vivo, Journal of Endocrinology, 175: 525-533, 2002.
Extended European Search Report for Application No. 18182456.6-1111/3530671, dated Oct. 14, 2019.

* cited by examiner

GIP PEPTIDE ANALOGUES

FIELD OF INVENTION

The present invention relates to Glucose-dependent insulinotropic peptide-derived peptide analogues and their use for treatment of disorders such as obesity, diabetes mellitus and insulin resistance.

BACKGROUND OF INVENTION

Glucose-dependent insulinotropic peptide (GIP) is a hormone secreted from the K cells of the gut following a meal[1]. Like its sister hormone glucagon-like peptide 1 (GLP-1), GIP is a potent insulin secretagogue[2]. In contrast to the glucagonostatic effect of GLP-1[3, 4], GIP has been shown to display glucagon-releasing properties under certain conditions ([3, 5-13]). The interest in understanding the biology of GIP was intensified by the association between rodent GIPR (GIP receptor) and adiposity[14-17, 17-21]. In humans, although less clear, there is likewise evidence for a role of GIP in fat metabolism with the demonstration of the GIPR expression in adipose tissue[22], an association between high BMI and increased GIP levels[22, 23], increased adipose tissue blood flow and TAG (triacylglycerol) deposition following GIP administration in a state of high insulin and high glucose[24], decreased basal and postprandial GIP levels observed in obese children put on a diet[25], and increased fasting GIP levels observed in healthy young men put on a high fat diet[26].

Thus, in addition to the general demand from researchers who witnessed the advances in the understanding of GLP-1 following the discovery of the GLP-1 receptor antagonist, exendin(9-39)[27, 28], the potential as an anti-obesity agent has attracted additional attention for the development of potent GIPR antagonists. Many different strategies have been undertaken in order to antagonize GIP's function, e.g. a small molecule receptor antagonist[29], immunization against GIP[30-32], various truncations and mutations of the GIP molecule with antagonistic properties[33-39], and recently a potent antagonist antibody against the GIPR[40].

Under physiological conditions the 42 amino acid hormone, GIP, is degraded by the enzyme dipeptidylpeptidase 4 (DPP-4), which cleaves at the third position of the GIP molecule to yield GIP3-42. Synthetic porcine GIP3-42 displayed no antagonist properties in pigs or perfused rat pancreata in physiological concentrations while in vitro it antagonized the hGIPR[41]. Many peptide hormones are post-translationally modified resulting in various biological forms with different lengths and amino acid modifications[42, 43]. Thus, it has been shown that GIP1-30 is produced as a result of post-translational processing[44] and that it is an agonist on the GIPR[33, 45]. If GIP1-30 is secreted into the circulation in humans, the cleavage catalyzed by DPP-4 would result in GIP3-30 (see FIG. 1).

U.S. Pat. No. 7,875,587 discloses GIP receptor antagonists derived from GIP(1-42) having enhanced resistance to degradation by DPP-4, and their use for treatment of insulin resistance and obesity. In WO2004/067548 DPP-4 metabolites are modified by covalent coupling of a pharmacophore to achieve the longer half-life associated with the peptide metabolites and to retain the biological activity of the cleaved peptides similar to the native peptides, including GIP. WO2012/055770 discloses GIP(3-42) as an endogenous metabolite that is readily cleared and with GIPR antagonist effects, and GIP(2-30) as an example of a truncated GIP analogue with GIPR agonist activity. WO1998/24464 discloses the antagonist GIP(7-30).

SUMMARY OF INVENTION

The present inventors have characterized GIP peptide analogues and evaluated their affinity to GIPRs, in particular the hGIPR (human GIPR), and their ability to antagonize GIPR activity, in particular the hGIPR. Thus, highly potent antagonists of the hGIPR are disclosed herein.

In one aspect, the invention relates to a peptide consisting of 21 to 39 contiguous amino acid residues derived from gastric inhibitory peptide (GIP)
wherein said peptide comprises at least the sequence TFISDYSIAMDKIX$_1$QQDFVNW (GIP5-25, SEQ ID NO: 5),
wherein X$_1$ is any amino acid,
wherein said peptide does not comprise the Tyr amino acid of position 1 of SEQ ID NO: 4, and wherein said peptide does not comprise the Ala amino acid of position 2 of SEQ ID NO: 4,
or a functional variant thereof having at least 60% identity to said peptide.

In a particular embodiment the peptide of the invention is hGIP3-30 (SEQ ID NO: 1), hGIP(3-30)H18R or rGIP3-30 (SEQ ID NO: 2), or hGIP(3-30)H18R/K30R or mGIP3-30 (SEQ ID NO: 3), or functional variants thereof.

In another aspect, the invention relates to the use of such peptides as a medicament.

In yet another aspect, the invention relates to the use of such peptides in a method of antagonizing a GIP receptor; or treating metabolic disorders (or metabolic syndrome), such as obesity, diabetes mellitus, insulin resistance and fatty acid metabolism disorder. In other aspects the invention relates to methods of treating cancer. In other aspects the invention relates to methods of treating a bone density disorder.

DEFINITIONS

Figure 1:
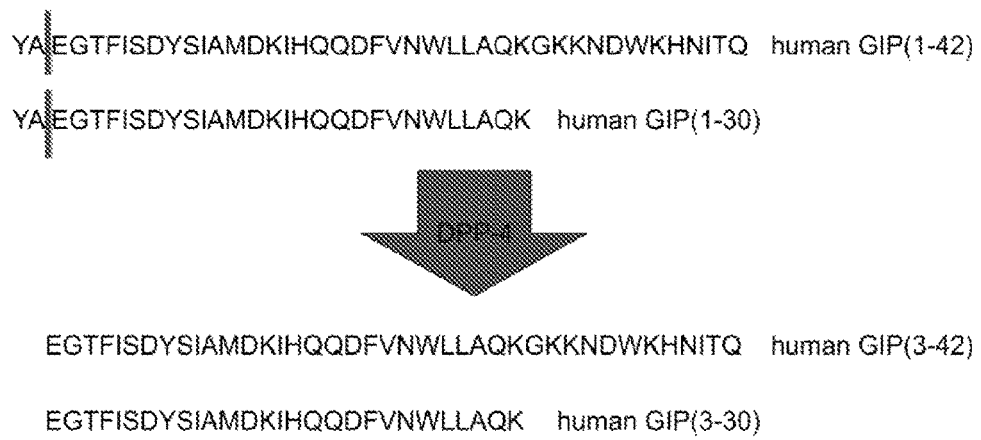
FIG. 1. The degradation of hGIP(1-42) (SEQ ID NO: 65) and hGIP(1-30) (SEQ ID NO:69) by DPP-4 into hGIP(3-42) (SEQ ID NO: 62) and hGIP(3-30) (SEQ ID NO: 1).

The term "affinity" refers to the strength of binding between a receptor and its ligand(s). In the present context, affinity of an antagonist for its binding site (Ki) will determine the duration of inhibition of agonist activity. The affinity of an antagonist can be determined experimentally using Schild regression or for competitive antagonists in radioligand binding studies using the Cheng-Prusoff equation (cf. examples).

The term "IC50" represents the half maximal inhibitory concentration (IC50), which is a measure of the effectiveness of a substance in inhibiting a specific biological or biochemical function. This quantitative measure indicates how much of a particular drug or other substance (e.g. antagonist) is needed to inhibit a given biological process (or component of a process, i.e. an enzyme, cell, cell receptor or microorganism) by half. It is commonly used as a measure of antagonist drug potency in pharmacological research. IC50 represents the concentration of a drug that is required for 50% inhibition in vitro. In the present context, the IC50 value can also refer to the concentration of a drug at which 50% of a radio labelled ligand is displaced from the receptor, which is a characterization of drug affinity done in competition binding experiments.

The term "agonist" in the present context refers to a peptide as defined herein, capable of binding to and activating a receptor.

The term "antagonist" in the present context refers to a peptide as defined herein, capable of binding to and blocking or reducing agonist-mediated responses of a receptor. Antagonists usually do not provoke a biological response themselves upon binding to a receptor. Antagonists have affinity but no efficacy for their cognate receptors, and binding will disrupt the interaction and inhibit the function of an agonist or inverse agonist at receptors. Antagonists mediate their effects by binding to the active (orthosteric) site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists typically achieve their potency by competing with endogenous ligands or substrates at structurally defined binding sites on receptors. Antagonists may be competitive, non-competitive, uncompetitive, silent antagonists, partial agonists or inverse agonists.

A competitive antagonist (also known as surmountable antagonist) reversibly binds to receptors at the same binding site (i.e. at the active site) as the endogenous ligand or agonist, but without activating the receptor. Agonists and antagonists thus "compete" for the same binding site on the receptor. Once bound, an antagonist blocks agonist binding. The level of activity of the receptor is determined by the relative affinity of each molecule for the site and their relative concentrations. High concentrations of a competitive antagonist will increase the proportion of receptors that the antagonist occupies, higher concentrations of the agonist will be required to obtain the same degree of binding site occupancy.

The term "non-competitive antagonism" (also called non-surmountable or insurmountable antagonism) describes two distinct phenomena with functionally similar results: one in which the antagonist binds to the active site of the receptor, and one in which the antagonist binds to an allosteric site of the receptor. Unlike competitive antagonists, which affect the amount of agonist necessary to achieve a maximal response but do not affect the magnitude of that maximal response, non-competitive antagonists reduce the magnitude of the maximum response that can be attained by any amount of agonist.

An uncompetitive antagonist requires receptor activation by an agonist before it can bind to a separate allosteric binding site. This type of antagonism produces a kinetic profile in which the same amount of antagonist blocks higher concentrations of agonist better than lower concentrations of agonist.

The term "silent antagonist" refers to a competitive receptor antagonist that has absolutely no intrinsic activity for activating a receptor.

The term "partial agonist" refers to an agonist that, at a given receptor, might differ in the amplitude of the functional response that it elicits after maximal receptor occupancy. Partial agonists can act as a competitive antagonist in the presence of a full agonist (or a more efficacious agonist), as it competes with the full agonist for receptor occupancy, thereby producing a net decrease in the receptor activation as compared to that observed with the full agonist alone.

The term "inverse agonist" refers to agonists having effects similar to those of antagonists, but causing a distinct set of downstream biological responses. Constitutively active receptors that exhibit intrinsic or basal activity can have inverse agonists, which not only block the effects of binding agonists like a classical antagonist but also inhibit the basal activity of the receptor.

The term "Individual" refers to vertebrates, particular members of the mammalian species, preferably primates including humans. As used herein, 'subject' and 'individual' may be used interchangeably.

An "isolated peptide" is a peptide separated and/or recovered from a component of their natural, typically cellular, environment, that is essentially free from contaminating cellular components, such as carbohydrate, lipid, or other proteinaceous impurities associated with the polypeptide in nature. Typically, a preparation of isolated peptide contains the peptide in a highly purified form, i.e., at least about 80% pure, at least about 90% pure, at least about 95% pure, greater than 95% pure, or greater than 99% pure. The term "isolated" does not exclude the presence of the same peptide in alternative physical forms, such as dimers, tetramers or alternatively glycosylated or derived forms.

An "amino acid residue" can be a natural or non-natural amino acid residue linked by peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed herewith: Y, G, F, M, A, S, I, L, T, V, P, K, H, Q, E, W, R, D, N and C. Non-natural amino acids are those not listed immediately above. Also, non-natural amino acid residues include, but are not limited to, modified amino acid residues, L-amino acid residues, and stereoisomers of D-amino acid residues.

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

Within the meaning of the term "equivalent amino acid substitution" as applied herein, one amino acid may be substituted for another, in one embodiment, within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

A "functional variant" of a peptide is a peptide capable of performing essentially the same functions as the peptide it is a functional variant of. In particular, a functional variant can bind the same molecules, preferably with the same affinity, as the peptide it is a functional variant of.

A "bioactive agent" (i.e. a biologically active substance/agent) is any agent, drug, compound, composition of matter or mixture which provides some pharmacologic, often beneficial, effect that can be demonstrated in vivo or in vitro. It refers to the peptide sequences according to the present invention, compounds or compositions comprising these and nucleic acid constructs encoding said peptides. As used herein, this term further includes any physiologically or pharmacologically active substance that produces a localized or systemic effect in an individual. A 'bioactive agent' as used herein denotes collectively a peptide, a nucleic acid construct encoding said peptide, and a composition comprising a peptide according to the present invention.

The terms "drug" and "medicament" as used herein include biologically, physiologically, or pharmacologically active substances that act locally or systemically in the human or animal body.

The terms "treatment" and "treating" as used herein refer to the management and care of a patient for the purpose of combating a condition, disease or disorder. The term is intended to include the full spectrum of treatments for a given condition from which the patient is suffering, and refer equally to curative therapy, prophylactic or preventative therapy and ameliorating or palliative therapy, such as administration of the peptide or composition for the purpose of: alleviating or relieving symptoms or complications; delaying the progression of the condition, partially arresting the clinical manifestations, disease or disorder; curing or eliminating the condition, disease or disorder; amelioration or palliation of the condition or symptoms, and remission (whether partial or total), whether detectable or undetectable; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The term "palliation", and variations thereof, as used herein, means that the extent and/or undesirable manifestations of a physiological condition or symptom are lessened and/or time course of the progression is slowed or lengthened, as compared to not administering compositions of the present invention.

The individual to be treated is preferably a mammal, in particular a human being. Treatment of animals, such as mice, rats, dogs, cats, cows, horses, sheep and pigs, is, however, also within the scope of the present invention.

An "individual in need thereof" refers to an individual who may benefit from the present invention. In one embodiment, said individual in need thereof is a diseased individual, wherein said disease may be a metabolic disease or disorder such as obesity or diabetes, a bone density disorder or a cancer.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

A treatment according to the invention can be prophylactic, ameliorating and/or curative.

"Pharmacologically effective amount", "pharmaceutically effective amount" or "physiologically effective amount" of a "bioactive agent" is the amount of a bioactive agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered.

"Co-administering" or "co-administration" as used herein refers to the administration of one or more peptides of the present invention and a state-of-the-art pharmaceutical composition. The at least two components can be administered separately, sequentially or simultaneously.

DETAILED DESCRIPTION OF THE INVENTION

GIP refers to glucose-dependent insulinotropic polypeptide, also known as Gastric Inhibitory Peptide (or polypeptide). As used herein the abbreviation hGIP is human GIP (Uniprot accession number P09681), mGIP is mouse GIP (Uniprot accession number P48756) and rGIP is rat GIP (Uniprot accession number Q06145). GIP is derived from a 153-amino acid proprotein and circulates as a biologically active 42-amino acid peptide. It is synthesized by K cells of the mucosa of the duodenum and the jejunum of the gastrointestinal tract.

GIPR (or GIP receptor) refers to gastric inhibitory polypeptide receptors. These seven-transmembrane proteins are found at least on beta-cells in the pancreas. As used herein the abbreviation hGIPR is human GIPR (Uniprot accession number P48546), mGIPR is mouse GIPR (Uniprot accession number Q0P543) and rGIPR is rat GIPR (Uniprot accession number P43219).

The present inventors have identified GIP analogues with novel properties and surprisingly found that the GIP analogues of the present invention are antagonists of one or more GIPRs. This makes them potentially useful in a range of therapeutic applications.

Peptides According to the Invention

The present invention is directed to GIP peptide analogues which GIP peptide analogues do not comprise the two most N-terminal amino acid residues of native GIP. In some embodiments the GIP peptide analogues do not comprise the 2, 3 or 4 most N-terminal amino acid residues of native GIP.

It is an aspect of the invention to provide a peptide consisting of 21 to 39 contiguous amino acid residues derived from gastric inhibitory peptide (GIP) (e.g. SEQ ID NO: 4), wherein said peptide comprises at least the sequence TFISDYSIAMX$_{0a}$X$_{0b}$IX$_1$QQDFVNW (GIP5-25; SEQ ID NO: 73) or TFISDYSIAMDKIX$_1$QQDFVNW (GIP5-25, SEQ ID NO: 5), wherein X$_{0a}$, X$_{0b}$, X$_1$ and X$_1$ individually is any amino acid, wherein said peptide does not comprise the Tyr amino acid of position 1 of SEQ ID NO: 4 (nor any other amino acid at position 1 of SEQ ID NO: 4), and wherein said peptide does not comprise the Ala amino acid of position 2 of SEQ ID NO: 4 (nor any other amino acid at position 2 of SEQ ID NO: 4), or a functional variant thereof having at least 60% identity to said peptide.

In one embodiment the peptides are selected from the group consisting of (GIP3-30; SEQ ID NO: 74)
EGTFISDYSIAMX$_{0a}$X$_{0b}$IX$_1$QQDFVNWLLAQX$_2$, (GIP4-30; SEQ ID NO: 75)
GTFISDYSIAMX$_{0a}$X$_{0b}$IX$_1$QQDFVNWLLAQX$_2$,
and (GIP5-30; SEQ ID NO: 76)
TFISDYSIAMX$_{0a}$X$_{0b}$IX$_1$QQDFVNWLLAQX$_2$, wherein X$_{0a}$, X$_{0b}$, X$_1$ and X$_2$ are individually any amino acid.

In one embodiment the peptides are selected from any one of SEQ ID NOs: 1-3, 5-61 and 72-91.

In one embodiment the peptides are selected from the group consisting of EGTFISDYSIAMX$_{0a}$X$_{0b}$IX$_1$QQDFVNWLLAQX$_2$—NH$_2$, GTFISDYSIAMX$_{0a}$X$_{0b}$IX$_1$QQDFVNWLLAQX$_2$—NH$_2$ and TFISDYSIAMX$_{0a}$X$_{0b}$IX$_1$QQDFVNWLLAQX$_2$—NH$_2$, wherein X$_{0a}$, X$_{0b}$, X$_1$ and X$_2$ are individually any amino acid.

It is a further aspect of the invention to provide hGIP(2-30), hGIP(6-30), hGIP(7-30), hGIP(8-30) and hGIP(9-30), or a functional variant thereof, per se or in a method as defined herein elsewhere.

In one embodiment, the peptides of the invention are capable of binding to and antagonising a GIPR. In some embodiments, the GIPR is the human GIPR (Uniprot accession number P48546), the mouse GIPR (Uniprot accession number Q0P543) or the rat GIPR (Uniprot accession number P43219).

The terms 'peptide' and 'isolated peptide' may be used interchangeably herein. The terms 'variant' and 'functional variant' may be used interchangeably herein. According to the present invention, a peptide as defined herein may be a functional variant of said defined amino acid sequence.

When reference is made to a 'peptide' herewith, this term will encompass both references to a peptide per se, and also to a peptide for use according to the present invention.

Functional variants of the peptides according to the present invention are the functional equivalents of said sequences, i.e. they retain at least some effect associated with the native sequence.

In one embodiment a functional variant retains the same biological activity or capabilities as the native peptide or the peptide from which it is derived. In one embodiment a peptide and a functional variant thereof according to the present invention is capable of one or more of: Binding to one or more GIPRs; antagonizing one or more GIPRs; displacing GIP1-42 and/or GIP1-30 from one or more GIPRs; having a higher affinity for a given GIPR than GIP1-42 and/or GIP1-30; antagonizing somatostatin secretion induced by native GIP, GIP1-42 and/or GIP1-30; antagonizing insulin secretion induced by native GIP, GIP1-42 and/or GIP1-30; and antagonising glucagon secretion induced by native GIP, GIP1-42 and/or GIP1-30.

In one embodiment a peptide and a functional variant thereof according to the invention is capable of binding (or binds) to one or more of the hGIPR (Uniprot accession number P48546), the rGIPR (Uniprot accession number P43219) and the mGIPR (Uniprot accession number Q0P543).

In one embodiment a peptide and a functional variant thereof according to the invention is capable of inhibiting (reducing, antagonizing) one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR and vii) release of GIP following a meal (post-prandial GIP release).

In one embodiments, the peptide comprises at least the sequence TFISDYSIAMDKIX$_1$QQDFVNW (GIP5-25, SEQ ID NO: 5), wherein X$_1$ at position 18 is any amino acid, such as a naturally occurring or a non-naturally occurring amino acid as defined herein.

In one embodiments, the peptide comprises at least the sequence TFISDYSIAMDKIX$_1$QQDFVNWLLAQX$_2$ (GIP5-30, SEQ ID NO: 78), wherein X$_1$ at position 18 and X$_2$ at position 30 is individually any amino acid, such as a naturally occurring or a non-naturally occurring amino acid as defined herein.

In one embodiment, the peptides of the invention do not comprise the first two amino acids of GIP, i.e. the peptides of the invention do not comprise the Tyr amino acid of position 1 and do not comprise the Ala amino acid of position 2 of SEQ ID NO: 4.

A peptide that comprises or consists of a sequence means that the peptide can comprise the sequence, consist of the sequence, or comprise at least the full sequence. A peptide that 'comprises at least' a peptide sequence, such as 'comprising at least the sequence TFISDYSIAMDKIX$_1$QQDFVNW', means that the peptide includes all of the peptide sequence TFISDYSIAMDKIX$_1$QQDFVNW (GIP5-25, SEQ ID NO: 5). It does, however, not exclude that additional components or amino acids are present.

In one embodiment the peptide is non-naturally occurring.
In one embodiment the peptide is synthetic.
In one embodiment the peptide is an isolated peptide.

In one embodiment the peptide is selected from the group consisting of

EGTFISDYSIAMX$_{0a}$X$_{0b}$IX$_1$QQDFVNWLLAQX$_2$, (GIP3-30; SEQ ID NO: 74)

GTFISDYSIAMX$_{0a}$X$_{0b}$IX$_1$QQDFVNWLLAQX$_2$, (GIP4-30; SEQ ID NO: 75) and

TFISDYSIAMX$_{0a}$X$_{0b}$IX$_1$QQDFVNWLLAQX$_2$, (GIP5-30; SEQ ID NO: 76)

wherein X$_{0a}$, X$_{0b}$, X$_1$ and X$_2$ are individually any amino acid,
or a functional variant thereof having at least 75% sequence identity to said peptide.

In one embodiment the peptide is selected from the group consisting of

EGTFISDYSIAMDKIX$_1$QQDFVNWLLAQX$_2$, (GIP3-30; SEQ ID NO: 11)

GTFISDYSIAMDKIX$_1$QQDFVNWLAQX$_2$, (GIP4-30; SEQ ID NO: 28)

TFISDYSIAMDKIX$_1$QQDFVNWLLAQX$_2$, (GIP5-30; SEQ ID NO: 45)

wherein X$_{0a}$, X$_{0b}$, X$_1$ and X$_2$ are individually any amino acid,
or a functional variant thereof having at least 75% sequence identity to said peptide.

The peptide of the invention is in one embodiment selected from the group consisting of:

EGTFISDYSIAMDKIX$_1$QQDFVNW, (GIP3-25, SEQ ID NO: 6)

EGTFISDYSIAMDKIX$_1$QQDFVNWL, (GIP3-26, SEQ ID NO: 7)

EGTFISDYSIAMDKIX$_1$QQDFVNWLL, (GIP3-27, SEQ ID NO: 8)

EGTFISDYSIAMDKIX$_1$QQDFVNWLLA, (GIP3-28, SEQ ID NO: 9)

EGTFISDYSIAMDKIX$_1$QQDFVNWLLAQ, (GIP3-29, SEQ ID NO: 10)

EGTFISDYSIAMDKIX$_1$QQDFVNWLLAQX$_2$, (GIP3-30, SEQ ID NO: 11)

EGTFISDYSIAMDKIX$_1$QQDFVNWLLAQX$_2$G, (GIP3-31, SEQ ID NO: 12)

EGTFISDYSIAMDKIX$_1$QQDFVNWLLAQX$_2$GK, (GIP3-32, SEQ ID NO: 13)

EGTFISDYSIAMDKIX$_1$QQDFVNWLLAQX$_2$GKK, (GIP3-33, SEQ ID NO: 14)

EGTFISDYSIAMDKIX$_1$QQDFVNWLLAQX$_2$GKKN, (GIP3-34, SEQ ID NO: 15)

EGTFISDYSIAMDKIX$_1$QQDFVNWLLAQX2GKKND, (GIP3-35, SEQ ID NO: 16)

EGTFISDYSIAMDKIX$_1$QQDFVNWLLAQX$_2$GKKNDW, (GIP3-36, SEQ ID NO: 17)

EGTFISDYSIAMDKIX$_1$QQDFVNWLLAQX$_2$GKKNDWK, (GIP3-37, SEQ ID NO: 18)

EGTFISDYSIAMDKIX$_1$QQDFVNWLLAQX$_2$GKKNDWKH, (GIP3-38, SEQ ID NO: 19)

EGTFISDYSIAMDKIX$_1$QQDFVNWLLAQX$_2$GKKNDWKHN, (GIP3-39, SEQ ID NO: 20)

EGTFISDYSIAMDKIX$_1$QQDFVNWLLAQX$_2$GKKNDWKHNI, (GIP3-40, SEQ ID NO: 21)

EGTFISDYSIAMDKIX$_1$QQDFVNWLLAQX$_2$GKKNDWKHNIT, (GIP3-41, SEQ ID NO: 22)

or a functional variant thereof, wherein X$_1$ and X$_2$ are individually any amino acid, such as a naturally occurring or a non-naturally occurring amino acid as defined herein.

In a particular embodiment the peptide of the invention is EGTFISDYSIAMDKIX$_1$QQDFVNWLLAQX$_2$ (GIP3-30, SEQ ID NO: 11), or a functional variant thereof, wherein X$_1$ and X$_2$ are individually any amino acid.

In a particular embodiment, the peptide is hGIP3-30 (SEQ ID NO: 1), or a variant thereof. In a preferred embodiment, the peptide consists of hGIP3-30 (SEQ ID NO: 1).

In a particular embodiment, the peptide is rGIP3-30 (SEQ ID NO: 2), or a variant thereof. In a preferred embodiment, the peptide consists of rGIP3-30 (SEQ ID NO: 2).

In a particular embodiment, the peptide is mGIP3-30 (SEQ ID NO: 3), or a variant thereof. In a preferred embodiment, the peptide consists of mGIP3-30 (SEQ ID NO: 3).

In some embodiment the peptide of the invention does not comprise the Glu amino acid of position 3 (or any other amino acid at position 3) of SEQ ID NO: 4. In this embodiment the peptide is selected from the group consisting of:

GTFISDYSIAMDKIX$_1$QQDFVNW, (GIP4-25, SEQ ID NO: 23)

GTFISDYSIAMDKIX$_1$QQDFVNWL, (GIP4-26, SEQ ID NO: 24)

GTFISDYSIAMDKIX$_1$QQDFVNWLL, (GIP4-27, SEQ ID NO: 25)

GTFISDYSIAMDKIX$_1$QQDFVNWLLA, (GIP4-28, SEQ ID NO: 26)

GTFISDYSIAMDKIX$_1$QQDFVNWLLAQ, (GIP4-29, SEQ ID NO: 27)

GTFISDYSIAMDKIX$_1$QQDFVNWLLAQX$_2$, (GIP4-30, SEQ ID NO: 28)

GTFISDYSIAMDKIX$_1$QQDFVNWLLAQX$_2$G, (GIP4-31, SEQ ID NO: 29)

GTFISDYSIAMDKIXVQQDFVNWLLAQX$_2$GK, (GIP4-32, SEQ ID NO: 30)

GTFISDYSIAMDKIX$_1$QQDFVNWLLAQX$_2$GKK, (GIP4-33, SEQ ID NO: 31)

GTFISDYSIAMDKIX$_1$QQDFVNWLLAQX$_2$GKKN, (GIP4-34, SEQ ID NO: 32)

GTFISDYSIAMDKIX$_1$QQDFVNWLLAQX$_2$GKKND, (GIP4-35, SEQ ID NO: 33)

GTFISDYSIAMDKIX$_1$QQDFVNWLLAQX$_2$GKKNDW, (GIP4-36, SEQ ID NO: 34)

GTFISDYSIAMDKIX$_1$QQDFVNWLLAQX$_2$GKKNDWK, (GIP4-37, SEQ ID NO: 35)

-continued

```
                                 (GIP4-38, SEQ ID NO: 36)
GTFISDYSIAMDKIX₁QQDFVNWLLAQX₂GKKNDWKH, (GIP4-39, SEQ ID NO: 37)
GTFISDYSIAMDKIX₁QQDFVNWLLAQX₂GKKNDWKHN, (GIP4-40, SEQ ID NO: 38)
GTFISDYSIAMDKIX₁QQDFVNWLLAQX₂GKKNDWKHNI, (GIP4-41, SEQ ID NO: 39)
GTFISDYSIAMDKIX₁QQDFVNWLLAQX₂GKKNDWKHNIT, (GIP4-42, SEQ ID NO: 40)
GTFISDYSIAMDKIX₁QQDFVNWLLAQX₂GKKNDWKHNITQ,
``` or a functional variant thereof, wherein $X_1$ and $X_2$ are individually any amino acid, such as a naturally occurring or a non-naturally occurring amino acid as defined herein.

In some embodiment the peptide of the invention does not comprise the Glu amino acid of position 3 (or any other amino acid at position 3) and the Gly amino acid of position 4 (or any other amino acid at position 4) of SEQ ID NO: 4. In this embodiment the peptide is selected from the group consisting of:

```
                                 (GIP5-25, SEQ ID NO: 5)
TFISDYSIAMDKIX₁QQDFVNW, (GIP5-26, SEQ ID NO: 41)
TFISDYSIAMDKIX₁QQDFVNWL, (GIP5-27, SEQ ID NO: 42)
TFISDYSIAMDKIX₁QQDFVNWLL, (GIP5-28, SEQ ID NO: 43)
TFISDYSIAMDKIX₁QQDFVNWLLA, (GIP5-29, SEQ ID NO: 44)
TFISDYSIAMDKIX₁QQDFVNWLLAQ, (GIP5-30, SEQ ID NO: 45)
TFISDYSIAMDKIX₁QQDFVNWLLAQX₂, (GIP5-31, SEQ ID NO: 46)
TFISDYSIAMDKIX₁QQDFVNWLLAQX₂G, (GIP5-32, SEQ ID NO: 47)
TFISDYSIAMDKIX₁QQDFVNWLLAQX₂GK, (GIP5-33, SEQ ID NO: 48)
TFISDYSIAMDKIX₁QQDFVNWLLAQX₂GKK, (GIP5-34, SEQ ID NO: 49)
TFISDYSIAMDKIX₁QQDFVNWLLAQX₂GKKN, (GIP5-35, SEQ ID NO: 50)
TFISDYSIAMDKIX₁QQDFVNWLLAQX₂GKKND, (GIP5-36, SEQ ID NO: 51)
TFISDYSIAMDKIX₁QQDFVNWLLAQX₂GKKNDW, (GIP5-37, SEQ ID NO: 52)
TFISDYSIAMDKIX₁QQDFVNWLLAQX₂GKKNDWK, (GIP5-38, SEQ ID NO: 53)
TFISDYSIAMDKIX₁QQDFVNWLLAQX₂GKKNDWKH (GIP5-39, SEQ ID NO: 54)
TFISDYSIAMDKIX₁QQDFVNWLLAQX₂GKKNDWKHN, (GIP5-40, SEQ ID NO: 55)
TFISDYSIAMDKIX₁QQDFVNWLLAQX₂GKKNDWKHNI, (GIP5-41, SEQ ID NO: 56)
TFISDYSIAMDKIX₁QQDFVNWLLAQX₂GKKNDWKHNIT, (GIP5-42, SEQ ID NO: 57)
TFISDYSIAMDKIX₁QQDFVNWLLAQX₂GKKNDWKHNITQ,
``` or a functional variant thereof, wherein $X_1$ and $X_2$ are individually any amino acid, such as a naturally occurring or a non-naturally occurring amino acid as defined herein.

In one embodiment $X_1$ and $X_2$ as defined herein for peptide variants are identical to the amino acid in the corresponding position in human GIP.

In one embodiment $X_1$ is His and/or $X_2$ is Lys.

In one embodiment $X_1$ and $X_2$ as defined herein for peptide variants are identical to the amino acid in the corresponding position in rat and/or mouse GIP.

In one embodiment $X_1$ is Arg and/or $X_2$ is Lys.

In one embodiment $X_1$ is Arg and/or $X_2$ is Arg.

In one embodiment $X_1$ (position 18) is any amino acid, such as a naturally occurring or a non-naturally occurring amino acid. In preferred embodiments, $X_1$ is selected from the group consisting of Ala, His, Arg and Lys. In these embodiments, the peptides of the invention consist of 21 to 39 contiguous amino acid residues and comprises or consists of at least a sequence selected from the group consisting of TFISDYSIAMDKIHQQDFVNW (SEQ ID NO: 59), TFISDYSIAMDKIRQQDFVNW (SEQ ID NO: 60), TFISDYSIAMDKIAQQDFVNW (SEQ ID NO: 61) and TFISDYSIAMDKIKQQDFVNW (SEQ ID NO: 72).

In one embodiment $X_2$ (position 30) is any amino acid, such as a naturally occurring or a non-naturally occurring amino acid. In preferred embodiments, $X_2$ is selected from the group consisting of Ala, Lys and Arg.

In one embodiment $X_1$ is His. In one embodiment $X_1$ is His and $X_2$ is Lys. In another embodiment $X_1$ is His and $X_2$ is Arg. In another embodiment $X_1$ is His and $X_2$ is Ala.

In one embodiment $X_1$ is Arg. In another embodiment $X_1$ is Arg and $X_2$ is Lys. In another embodiment $X_1$ is Arg and $X_2$ is Arg. In another embodiment $X_1$ is Arg and $X_2$ is Ala.

In another embodiment $X_1$ is Ala and $X_2$ is Lys. In another embodiment $X_1$ is Ala and $X_2$ is Arg. In another embodiment $X_1$ is Ala and $X_2$ is Ala.

In another embodiment $X_1$ is Lys and $X_2$ is Lys. In another embodiment $X_1$ is Lys and $X_2$ is Arg. In another embodiment $X_1$ is Lys and $X_2$ is Ala.

In one embodiment the peptide of the invention comprises the sequence TFISDYSIAM<u>DK</u>IX₁QQDFVNW (GIP5-25, SEQ ID NO: 5), or a variant thereof which is TFISDYSIAMX₀ₐX₀ᵦIX₁QQDFVNW, wherein D at position 15 ($X_{0a}$) and/or K at position 16 ($X_{0b}$) are individually any amino acid, such as a naturally occurring or a non-naturally occurring amino acid as defined herein.

In one embodiment $X_{0a}$ is selected from Asp and Ala. In one embodiment $X_{0b}$ is selected from Lys and Ala.

It is an aspect of the invention to provide a peptide consisting of 28 contiguous amino acid residues derived from gastric inhibitory peptide, wherein said peptide comprises or consists of a peptide selected from the group consisting of EGTFISDYSIAMDKIHQQDFVNWLLAQK (hGIP3-30, SEQ ID NO: 1), EGTFISDYSIAMDKIRQQDFVNWLLAQK (rGIP3-30, SEQ ID NO: 2), EGTFISDYSIAMDKIRQQDFVNWLLAQR (mGIP3-30, SEQ ID NO: 3), and functional variants thereof having at least 60% identity to said peptide.

'Identity' and 'sequence identity' is used interchangeably herein.

In one embodiment a functional variant according to the present invention is selected from the group consisting of:

```
                       (hGIP(3-30)H18A; SEQ ID NO: 79)
EGTFISDYSIAMDKIAQQDFVNWLLAQK, (hGIP(3-30)H18K; SEQ ID NO: 80)
EGTFISDYSIAMDKIKQQDFVNWLLAQ, (hGIP(3-30)D15EH18A; SEQ ID NO: 81)
EGTFISDYSIAMEKIAQQDFVNWLLAQK, (hGIP(3-30)K16AH18A; SEQ ID NO: 82)
EGTFISDYSIAMDAIAQQDFVNWLLAQK, (hGIP(3-30)D15E; SEQ ID NO: 83)
EGTFISDYSIAMEKIHQQDFVNWLLAQK, (hGIP(3-30)D15N; SEQ ID NO: 84)
EGTFISDYSIAMNKIHQQDFVNWLLAQK, (hGIP(3-30)K16A; SEQ ID NO: 85)
EGTFISDYSIAMDAIHQQDFVNWLLAQK, (hGIP(3-30)K16H; SEQ ID NO: 86)
EGTFISDYSIAMDHIHQQDFVNWLLAQK, (hGIP(3-30)K16R; SEQ ID NO: 87)
EGTFISDYSIAMDRIHQQDFVNWLLAQK, (hGIP(3-30)H18F; SEQ ID NO: 88)
EGTFISDYSIAMDKIFQQDFVNWLLAQK, (hGIP(3-30)H18W; SEQ ID NO: 89)
EGTFISDYSIAMDKIWQQDFVNWLLAQK, (hGIP(3-30)K30R SEQ ID NO: 90)
EGTFISDYSIAMDKIHQQDFVNWLLAQR,
and
                       (hGIP(3-30)K30H; SEQ ID NO: 91)
EGTFISDYSIAMDKIHQQDFVNWLLAQH.
```

In one embodiment, the peptide of the invention has at least 60% identity, such as at least 65% identity, such as at least 70% identity, such as at least 75% identity, such as at least 80% identity, such as at least 85% identity, such as at least 90% identity, such as at least 95% identity, such as at least 99% identity, such as 100% identity to the corresponding part of hGIP (SEQ ID NO: 65), rGIP (SEQ ID NO: 66) or mGIP (SEQ ID NO: 67).

In one embodiment, the peptide of the invention has 60 to 65% identity, such as 65 to 70% identity, such as 70 to 75% identity, such as 75 to 80% identity, such as 80 to 85% identity, such as 85 to 90% identity, such as 90 to 95% identity, such as 95 to 99% identity, such as 99 to 100% identity, such as 100% identity to the corresponding part of hGIP (SEQ ID NO: 65). In some embodiments, the peptide of the invention has 60 to 65% identity, such as 65 to 70% identity, such as 70 to 75% identity, such as 75 to 80% identity, such as 80 to 85% identity, such as 85 to 90% identity, such as 90 to 95% identity, such as 95 to 99% identity, such as 99 to 100% identity, such as 100% identity to hGIP3-30 (SEQ ID NO: 1), hGIP4-30 (SEQ ID NO:77), hGIP5-30 (SEQ ID NO:78), rGIP3-30 (SEQ ID NO: 2) or mGIP3-30 (SEQ ID NO: 3).

In one embodiment a variant of a peptide according to the present invention is a variant having 1 to 10 amino acid substitutions, such as 1 amino acid substitution, for example 2 amino acid substitutions, such as 3 amino acid substitutions, for example 4 amino acid substitutions, such as 5 amino acid substitutions, for example 6 amino acid substitutions, such as 7 amino acid substitutions, for example 8 amino acid substitutions, such as 9 amino acid substitutions, for example 10 amino acid substitutions as compared to the corresponding part of any one of SEQ ID NOs: 1 to 91/at a given position of any one of SEQ ID NOs: 1 to 91.

In one embodiment, one or more, or all, of said amino acid substitutions are conservative amino acid substitutions.

In one embodiment, the peptide according to the present invention does not comprise or consist of GIP1-42 (SEQ ID NO: 4). It follows that in one embodiment, the peptide according to the present invention does not comprise or consist of hGIP1-42 (SEQ ID NO: 65), rGIP1-42 (SEQ ID NO: 66) or mGIP1-42 (SEQ ID NO: 67).

In one embodiment, the peptide according to the present invention does not comprise or consist of the amino acid sequence GIP3-42 (SEQ ID NO: 58). It follows that in one embodiment, the peptide according to the present invention does not comprise or consist of hGIP3-42 (SEQ ID NO: 62), rGIP3-42 (SEQ ID NO: 63) or mGIP3-42 (SEQ ID NO: 64).

In one embodiment, the peptide according to the present invention does not comprise or consist of GIP1-30 (SEQ ID NO: 68). It follows that in one embodiment, the peptide according to the present invention does not comprise or consist of hGIP1-30 (SEQ ID NO: 69), rGIP1-30 (SEQ ID NO: 70) or mGIP1-30 (SEQ ID NO: 71).

In some embodiments, said one or more amino acid substitution(s) is a conservative amino acid substitution (or synonymous substitution). A conservative substitution is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

In one embodiment, a serine residue of a peptide of the invention is substituted with an amino acid selected from the group consisting of Gln, Asn and Thr (all amino acids with polar uncharged side chains); and independently thereof, a glycine residue (Gly) is substituted with an amino acid selected from the group consisting of Ala, Val, Leu, and Ile; and independently thereof, an arginine residue (Arg) is substituted with an amino acid selected from the group consisting of Lys and His (all have positively charged side chains); and independently thereof, a lysine residue (Lys) is substituted with an amino acid selected from the group consisting of Arg and His; and independently thereof, a methionine residue (Met) is substituted with an amino acid selected from the group consisting of Leu, Pro, Ile, Val, Phe, Tyr and Trp (all have hydrophobic side chains); and independently thereof, a glutamine residue (Gln) is substituted with an amino acid selected from the group consisting of Asp, Glu, and Asn; and independently thereof, an alanine residue (Ala) is substituted with an amino acid selected from the group consisting of Gly, Val, Leu, and Ile.

Particular amino acid substitutions of the present invention are K to R, E to D, L to M, Q to E, I to V, I to L, A to S, Y to W, K to Q, S to T, N to S and Q to R.

The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90, or by simple comparison of the specific amino acids present at corresponding positions in two peptide sequences to be compared.

Homology may be used as a synonym to identity/sequence identity.

In another embodiment, a variant according to the present invention includes sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, and/or wherein a dibasic monocarboxylic amino acid is substituted for a dibasic monocarboxylic amino acid.

Conservative substitutions may be introduced in any one or more positions of a peptide according to the invention, as long as the variant remains functional. It may however also be desirable to introduce non-conservative substitutions in one or more positions (non-synonymous substitutions).

A non-conservative substitution leading to the formation of a variant of the peptide according to the invention in one embodiment comprises substitution of amino acid residues that i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids can in one embodiment be made based upon their hydrophobicity and hydrophilicity values and the relative similarity of the amino acid side-chain substituents, including charge, size, and the like.

The peptides according to the present invention comprise proteinogenic or natural amino acids, i.e. the 22 amino acids naturally incorporated into polypeptides. Of these, 20 are encoded by the universal genetic code (cf. table X above) and the remaining 2; selenocysteine (Sec, U) and pyrrolysine (Pyl, O), are incorporated into proteins by unique synthetic mechanisms.

A peptide according to the invention in one embodiment comprises one or more non-naturally occurring amino acid residues (unnatural, non-proteinogenic or non-standard amino acids). Non-naturally occurring amino acids include e.g., without limitation, beta-2-naphthyl-alanine, trans-3-methylproline, 2,4-methanoproline, cis-4-hydroxyproline, ornithine, trans-4-hydroxyproline, N-methylglycine, allo-threonine, methylthreonine, hydroxyethylcysteine, hydroxyethylhomocysteine, nitroglutamnine, homoglutamine, pipecolic acid, thiazolidine carboxylic acid, dehydroproline, 3- and 4-methylproline, 3,3-dimethylproline, tert-leucine, norleucine, norvaline, 2-azaphenylalanine, 3-azaphenylalanine, 4-azaphenylalanine, and 4-fluorophenylalanine.

Any amino acids according to the present invention may be in the L- or D-configuration. If nothing is specified, reference to the L-isomeric form is preferably meant.

The standard and/or non-standard amino acids may be linked by peptide bonds (to form a linear peptide chain), or by non-peptide bonds (e.g. via the variable side-chains of the amino acids). Preferably, the amino acids of the present invention are linked by peptide bonds.

The term peptide also embraces post-translational modifications introduced by chemical or enzyme-catalyzed reactions, as are known in the art. These include acetylation, phosphorylation, methylation, glucosylation, glycation, amidation, hydroxylation, deimination, deamidation, carbamylation and sulfation of one or more amino acid residues, and also proteolytic modification by known proteinases including lysosomal kathepsins, and also calpains, secretases and matrix-metalloproteinases.

In one embodiment the peptide of the present invention is amidated, such as C-terminally amidated ($—NH_2$). In one exemplary embodiment thereof, the peptide is hGIP(3-30)-$NH_2$.

In one embodiment the peptide of the present invention is acetylated, such as N-terminally acetylated.

Also, functional equivalents of the peptides may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins (non-proteinogenic).

Sterically similar compounds may be formulated to mimic the key portions of the peptide structure. This may be achieved by techniques of modelling and chemical designing known to those of skill in the art. For example, esterification and other alkylations may be employed to modify the amino terminus of e.g. a di-arginine peptide backbone, to mimic a tetra peptide structure. It will be understood that all such sterically similar constructs fall within the scope of the present invention. Peptides with N-terminal and C-terminal alkylations and esterifications are also encompassed within the present invention.

A contiguous or consecutive peptide sequence is a sequence of consecutive amino acids being linked linearly by peptide bonds. Contiguous and consecutive amino acid sequence is used interchangeably herein.

A peptide of the present invention in one embodiment consists of 21 to 39 contiguous amino acids derived from GIP (SEQ ID NO: 4). In one embodiment, the peptide according to the present invention comprises or consists of a contiguous amino acid sequence of 39 amino acids, for example 38 amino acids, such as 37 amino acids, for example 36 amino acids, such as 35 amino acids, for example 34 amino acids, such as 33 amino acids, for example 32 amino acids, such as 31 amino acids, for example 30 amino acids, such as 29 amino acids, for example 28 amino acids, such as 27 amino acids, for example 26 amino acids, such as 25 amino acids, for example 24 amino acids, such as 23 amino acids, for example 22 amino acids, such as 21 amino acids derived from GIP (SEQ ID NO:4) which comprises at least the sequence TFISDYSIAMDKIX$_1$QQDFVNW (GIP5-25, SEQ ID NO: 5) or a variant thereof.

In a particular embodiment the peptide of the invention consists of 28 amino acids. In a particular embodiment the peptide of the invention consists of 28 amino acids corresponding to amino acids 3-30 of GIP (SEQ ID NO:4).

Compound of the Present Invention

It is an aspect of the present invention to provide a compound comprising or consisting of a peptide according to the present invention. In one embodiment, said peptide is formulated as a monomer (i.e. comprising 1 copy of the peptide), whereas in another embodiment, said peptide is formulated as a multimer.

Multimeric Compound

In one embodiment the peptide according to the present invention is formulated as a multimer. A multimer is a protein comprising or consisting of multiple monomers. A multimer is an aggregate of multiple molecules that is usually held together with non-covalent bonds. This definition distinguishes a multimer from a polymer, which is a series of monomers that are held together with covalent bonds.

A peptide sequence of the present invention is in one embodiment connected to another (identical or non-identical) peptide sequence of the present invention by a chemical bond or through a linker group. In some embodiments a peptide of the invention is formulated as an oligomer or multimer of monomers, wherein each monomer is as a peptide sequence as defined according to the present invention.

Thus, according to the invention a multimeric compound is in one embodiment a polymer comprising two or more peptide sequences of the invention, said peptide sequences being identical or non-identical, wherein at least one of the two or more peptide sequences is a peptide according to the present invention. Preferably, both peptide sequences are a peptide according to the present invention.

In one embodiment the multimeric compound is a dimer, comprising two peptides according to the present invention, said two peptides being identical or non-identical with respect to each other.

In another embodiment the multimeric compound is a trimer, comprising three peptides according to the present invention, said peptides being identical or non-identical with respect to each other.

In another embodiment the multimeric compound is a tetramer, comprising four peptides according to the present invention, said peptides being identical or non-identical with respect to each other.

In one embodiment the multimeric compound is a dendrimer, such as a tetrameric or octameric dendrimer. Dendrimers are repeatedly branched, roughly spherical large molecules, typically symmetric around the core, and often adopts a spherical three-dimensional morphology.

Dendrimers according to the present invention may comprise 4 peptides, 8 peptides, 16 peptides, or 32 peptides. In one particular embodiment said dendrimer comprises four peptides (i.e. a tetrameric dendrimer) or eight peptides (octameric dendrimer).

In some particular embodiments, the multimeric compound comprises two identical amino acid sequences of the present invention (dimer) or the compound comprises four identical copies of an amino acid sequence of the present invention (tetrameric dendrimer).

The multimers according to the invention is in one embodiment made by linking two or more peptide monomers via a peptide bond or a linker group. In one embodiment they are linked to a lysine backbone, such as a lysine residue (each peptide chain is linked to a single lysine residue), or coupled to a polymer carrier, for example a protein carrier. Said linker group in one embodiment comprises a plurality of lysine residues, such as a core moiety having a plurality of lysine residues, such as seen in a lysine-based dendromeric structure containing three, seven, fifteen and more lysine residues However, any other linking of peptide monomers known to the skilled person may be envisioned.

The linking in one embodiment occurs at the N-terminal and/or C-terminal end of the peptide monomers.

Antagonist Activity of the Peptides

In some embodiments, the peptides according to the invention are capable of binding to and antagonizing a GIPR. The GIPR can be any GIPR, including the human GIPR (Uniprot accession number P48546), the mouse GIPR (Uniprot accession number Q0P543) and the rat GIPR (Uniprot accession number P43219). In a preferred embodiment, the GIPR is the human GIPR (hGIPR).

Accordingly, the peptides of the invention will potentially reduce or prevent binding of full-length GIP1-42 and/or of GIP1-30 to the GIPR. In some embodiments, the peptide potentially reduces or prevents binding of full-length hGIP1-42 (SEQ ID NO: 65) and/or of hGIP1-30 (SEQ ID NO: 69) to the hGIPR (or the rGIPR or mGIPR). In other embodiments, the peptide potentially reduces or prevents binding of full-length rGIP1-42 (SEQ ID NO: 66) and/or of rGIP1-30 (SEQ ID NO: 70) to the rGIPR (or the hGIPR or mGIPR). In some embodiments, the peptide potentially reduces or prevents binding of full-length mGIP1-42 (SEQ ID NO: 67) and/or of mGIP1-30 (SEQ ID NO: 71) to the mGIPR (or hGIPR or rGIPR).

The peptides of the invention in one embodiment are selected from the group consisting of competitive antagonists, uncompetitive antagonists, non-competitive antagonists, silent antagonists, partial agonists or inverse agonists. In a particular embodiment, the peptide is a competitive antagonist of the GIPR.

Thus in some embodiments, the peptide is a competitive antagonist of the hGIPR. In other embodiments, the peptide is a competitive antagonist of the mGIPR. In other embodiments, the peptide is a competitive antagonist of the rGPIR. In other embodiments, the peptide is a competitive antagonist of two or more of the hGIPR, the rGIPR and the rGPIR.

Antagonists have a Ki value which reflects the affinity of antagonists for their receptor and consequently their ability to inhibit agonist binding. The peptide of the invention in one embodiment has a Ki of at least 1 nM, such as at least 5 nM, 10 nM, such at least 15 nM, such as at least 20 nM, such as at least 25 nM, such as 30 nM, such as at least 35 nM, such as 40 nM, such as at least 45 nM, such as at least 50 nM, such as at least 55 nM, such as at least 60 nM.

The peptide of the invention in one embodiment has a Ki of 1 to 200 nM, such as 1 to 5 nM, such as 5 to 10 nM, such as 10 to 15 nM, such as 15 to 20 nM, such as 20 to 25 nM, such as 25 to 30 nM, such as 30 to 35 nM, such as 35 to 40 nM, such as 40 to 45 nM, such as 45 to 50 nM, such as 50 to 55 nM, such as 55 to 60 nM, such as 60 to 65 nM, such as 65 to 70 nM, such as 70 to 75 nM, such as 75 to 80 nM, such as 80 to 85, such as 85 to 90 nM, such as 90 to 95 nM, such as 95 to 100 nM, such as 100 to 105 nM, such as 105 to 110 nM, such as 110 to 115 nM, such as 115 to 120 nM, such as 120 to 125 nM, such as 125 to 130 nM, such as 130 to 135 nM, such as 135 to 140 nM, such as 140 to 145 nM, such as 145 to 150 nM, such as 150 to 155 nM, such as 155 to 160 nM, such as 160 to 165 nM, such as 165 to 170 nM, such as 170 to 175 nM, such as 175 to 180 nM, such as 180 to 185 nM, such as 185 to 190 nM, such as 190 to 195 nM, such as 195 to 200 nM.

In some embodiments, the peptide has an affinity for a given GIPR which is higher than the affinity of hGIP1-42 (SEQ ID NO: 65) for the same GIPR. For example, the peptide in one embodiment has an affinity for the hGIPR, for the rGIPR and for the mGIPR which is higher than the affinity of hGIP1-42 (SEQ ID NO: 65) for the hGIPR, for the rGIPR and for the mGIPR, respectively.

In some embodiments, the peptide has an affinity for a given GIPR which is higher than the affinity of rGIP1-42

(SEQ ID NO: 59) for the same GIPR. For example, the peptide in one embodiment has an affinity for the hGIPR, for the rGIPR and for the mGIPR which is higher than the affinity of rGIP1-42 (SEQ ID NO: 59) for the hGIPR, for the rGIPR and for the mGIPR, respectively.

In some embodiments, the peptide has an affinity for a given GIPR which is higher than the affinity of mGIP1-42 (SEQ ID NO: 60) for the same GIPR. For example, the peptide in one embodiment has an affinity for the hGIPR, for the rGIPR and for the mGIPR which is higher than the affinity of mGIP1-42 (SEQ ID NO: 60) for the hGIPR, for the rGIPR and for the mGIPR, respectively.

In some embodiments the peptide of the invention is capable of displacing GIP1-42, GIP1-30 and/or GIP3-42 from a GIPR. In some embodiments the peptide of the invention is capable of displacing human, mouse or rat GIP1-42 and/or -GIP1-30 from the hGIPR, for the rGIPR and/or for the mGIPR. In one embodiment the peptide is capable of displacing hGIP1-42 (SEQ ID NO: 65) from the hGIPR. In one embodiment the peptide is capable of displacing rGIP1-42 (SEQ ID NO: 66) from the rGIPR. In one embodiment the peptide is capable of displacing mGIP1-42 (SEQ ID NO: 67) from the mGIPR.

In some embodiments, the peptide of the invention is capable of displacing hGIP1-42 (SEQ ID NO: 65) and/or hGIP1-30 (SEQ ID NO: 69) with an IC50 value of at least 0.5 nM, for example approx. 0.92 nM, such as at least 1 nM, such as at least 2 nM, such as at least 3 nM, such as at least 4 nM, such as at least 5 nM, such as at least 5.2 nM, such as at least 6 nM, such as at least 7 nM, such as at least 7.8 nM, such as at least 8 nM, such as at least 9 nM, such as at least 10 nM, such as at least 11 nM, such as at least 11.4 nM, such as at least 12 nM, such as at least 13 nM, such as at least 14 nM, such as at least 15 nM, such as at least 16 nM.

In some embodiments, the peptide of the invention is capable of displacing hGIP1-42 (SEQ ID NO: 65) and/or hGIP1-30 (SEQ ID NO: 69) with an IC50 value of 1 to 100 nM, such as 1 to 5 nM, such as 5 to 10 nM, such as 10 to 15 nM, such as 15 to 20 nM, such as 20 to 25 nM, such as 25 to 30 nM, such as 30 to 35 nM, such as 35 to 40 nM, such as 40 to 45 nM, such as 45 to 50 nM, such as 50 to 55 nM, such as 55 to 60 nM, such as 60 to 65 nM, such as 65 to 70 nM, such as 70 to 75 nM, such as 75 to 80 nM, such as 80 to 85 nM, such as 85 to 90 nM, such as 90 to 95 nM, such as 95 to 100 nM.

In some embodiments the peptide is capable of displacing hGIP1-42 (SEQ ID NO: 65) and/or hGIP1-30 (SEQ ID NO: 69) with an IC50 value of 1 to 100 nM. In other embodiments the peptide is capable of displacing rGIP1-42 (SEQ ID NO: 66) and/or rGIP1-30 (SEQ ID NO: 70) with an IC50 value of 1 to 100 nM. In other embodiments the peptide is capable of displacing mGIP1-42 (SEQ ID NO: 67) and/or mGIP1-30 (SEQ ID NO: 71) with an IC50 value of 1 to 100 nM.

In some embodiments, the peptides of the invention are capable of antagonizing somatostatin secretion induced by native GIP. In particular embodiments, the peptide is capable of antagonizing somatostatin secretion induced by hGIP1-42 (SEQ ID NO: 65).

In some embodiments, the peptides of the invention are capable of antagonizing insulin secretion induced by native GIP. In particular embodiments said peptide is capable of antagonising insulin secretion induced by hGIP1-42 (SEQ ID NO: 65).

In some embodiments, the peptides of the invention are capable of antagonizing glucagon secretion induced by native GIP. In particular embodiments said peptide is capable of antagonising glucagon secretion induced by hGIP1-42 (SEQ ID NO: 65).

Without being bound by theory, it is believed that antagonizing the GIPR results in reduced somatostatin levels and/or reduced insulin levels and/or lower free fatty acid levels.

Determining Antagonist Properties and Affinity

In order to determine whether a peptide is an antagonist of the GIPR, methods known in the art may be employed, for example by determining the IC50 of the peptide. This can be done by constructing a dose-response curve and examining the effect of different concentrations of the peptide on reversing agonist activity. The agonist can be GIP1-42, for example hGIP-1-42 (SEQ ID NO: 65), rGIP1-42 (SEQ ID NO: 66) or mGIP1-42 (SEQ ID NO: 67); or GIP1-30. The GIPR can be hGIPR, rGIPR or mGIPR. IC50 values can be calculated for a given antagonist by determining the concentration needed to inhibit half of the maximum biological response of the agonist. A method for determining whether a peptide is an antagonist is described in example 4, but other methods known in the art may also be used. For example, Schild plot analysis may be performed on hGIP1-42 (SEQ ID NO: 65) cAMP dose-response curves with increasing concentrations of GIP-derived peptides. In this way, the type of antagonist activity may also be determined.

Heterologous competition binding experiments may be performed in order to measure the affinity of the peptide for a GIPR, i.e. how efficiently the peptide is capable of displacing a given GIP1-42, for example hGIP1-42 (SEQ ID NO: 65), rGIP1-42 (SEQ ID NO: 66) or mGIP1-42 (SEQ ID NO: 67). These competition binding experiments may be performed as described in example 3 or by other methods known in the art. For example, GIP1-42 may be radioactively labelled, for example with $^{125}$I. Other suitable isotopes are known to the skilled person.

Nucleic Acid Construct Encoding GIP Peptide

There are a variety of metabolic disorders and diseases arising from genetic and non-genetic causes, or a combination of both. Beta-cells of the pancreas are a possible target of gene therapy.

In one embodiment of the present invention there is provided a nucleic acid construct encoding a peptide according to the present invention. Preferably said nucleic acid construct will be able to continuously express a peptide according to the present invention for a prolonged period of time, such as at least 1 month, for example at least 2 months, such as at least 3 months, for example at least 4 months, such as at least 5 months, for example at least 6 months, such as at least 7 months, for example at least 8 months, such as at least 9 months, for example at least 12 months.

It is an aspect of the present invention to provide a nucleic acid construct encoding a peptide according to the present invention.

In one embodiment there is provided a nucleic acid construct encoding a peptide selected from the group consisting of

```
                                  (GIP3-30; SEQ ID NO: 74)
     EGTFISDYSIAMX₀ₐX₀ᵦIX₁QQDFVNWLLAQX₂, (GIP4-30; SEQ ID NO: 75)
      GTFISDYSIAMX₀ₐX₀ᵦIX₁QQDFVNWLLAQX₂, (GIP5-30; SEQ ID NO: 76)
       TFISDYSIAMX₀ₐX₀ᵦIX₁QQDFVNWLLAQX₂,
``` wherein $X_{0a}$, $X_{0b}$, $X_1$ and $X_2$ are individually any amino acid, or a functional variant thereof having at least 75% sequence identity to said peptide, It is also an aspect of the present invention to provide a nucleic acid construct encoding a peptide according to the invention for use in a method of treating metabolic syndrome such as obesity, diabetes, insulin resistance or fatty acid metabolism disorder, or of atherosclerosis, or of treating a cancer such as colon cancer or adrenal adenoma, or of treating a bone density disorder such as a bone density disorder characterized by high bone density and/or increased bone volume.

In one embodiment, the encoded peptide of the nucleic acid construct is a peptide according to the invention as defined herein elsewhere.

By nucleic acid construct is understood a genetically engineered nucleic acid. The nucleic acid construct may be a non-replicating and linear nucleic acid, a circular expression vector or an autonomously replicating plasmid. A nucleic acid construct may comprise several elements such as, but not limited to genes or fragments of same, promoters, enhancers, terminators, poly-A tails, linkers, polylinkers, operative linkers, multiple cloning sites (MCS), markers, STOP codons, internal ribosomal entry sites (IRES) and host homologous sequences for integration or other defined elements. It is to be understood that the nucleic acid construct according to the present invention may comprise all or a subset of any combination of the above-mentioned elements.

Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). Further, nucleic acid constructs according to the present invention may be synthesized without template, and may be obtained from various commercial suppliers (e.g. Genscript Corporation). In one embodiment, the nucleic acid construct are naked DNA constructs comprising sequences encoding the peptide of the invention.

Delivery Vehicles

It is also an aspect of the present invention to provide the nucleic acid construct as described herein above comprised within a delivery vehicle. A delivery vehicle is an entity whereby a nucleotide sequence or polypeptide or both can be transported from at least one media to another. Delivery vehicles are generally used for expression of the sequences encoded within the nucleic acid construct and/or for the intracellular delivery of the construct or the polypeptide encoded therein.

In one embodiment, there is provided a delivery vehicle comprising the nucleic acid construct according to the present invention. A delivery vehicle may be selected from the group consisting of: RNA based vehicles, DNA based vehicles/vectors, lipid based vehicles (such as a liposome), polymer based vehicles (such as a cationic polymer DNA carrier), colloidal gold particles (coating) and virally derived DNA or RNA vehicles or vectors.

Methods of non-viral delivery include physical (carrier-free delivery) and chemical approaches (synthetic vector-based delivery).

Physical approaches, including needle injection, gene gun, jet injection, electroporation, ultrasound, and hydrodynamic delivery, employ a physical force that permeates the cell membrane and facilitates intracellular gene transfer. Said physical force may be electrical or mechanical.

Examples of chemical delivery vehicles include, but are not limited to: biodegradable polymer microspheres, lipid based formulations such as liposome carriers, cationically charged molecules such as liposomes, calcium salts or dendrimers, lipopolysaccharides, polypeptides and polysaccharides.

Another embodiment of the present invention comprises a vector which herein is denoted a viral vector (i.e. not a virus) as a delivery vehicle. Viral vectors according to the present invention are made from a modified viral genome, i.e. the actual DNA or RNA forming the viral genome, and introduced in naked form. Thus, any coat structures surrounding the viral genome made from viral or non-viral proteins are not part of the viral vector according to the present invention.

The virus from which the viral vector is derived may be selected from the non-exhaustive group of: adenoviruses, retroviruses, lentiviruses, adeno-associated viruses, herpes-viruses, vaccinia viruses, foamy viruses, cytomegaloviruses, Semliki forest virus, poxviruses, RNA virus vector and DNA virus vector. Such viral vectors are well known in the art.

In one embodiment, said viral vectors may be selected from the group consisting of adenoviruses, lentiviruses, adeno-associated viruses (AAV) and recombinant adeno-associated viruses (rAAV). In one preferred embodiment, said viral vector is a therapeutic rAAV vector such as a therapeutic rAAV vector.

An adenovirus is a group of double-stranded DNA containing viruses. Adenoviruses can be genetically modified making them replication incompetent or conditionally replication incompetent. In this form, as adenoviral constructs or adenovectors, they can be used as gene delivery vehicles for vaccination or gene therapy.

Gene therapy vectors using AAV can infect both dividing and quiescent cells and persist in an extrachromosomal state without integrating into the genome of the host cell. These features make AAV a very attractive candidate for creating viral vectors for gene therapy. To date, AAV vectors have been used in over 80 clinical trials worldwide.

Recombinant Cell

Another aspect of the present invention relates to a cell comprising the nucleic acid construct according to the present invention. Such a recombinant cell can be used a tool for in vitro research, as a delivery vehicle for the nucleic acid construct or as part of a gene-therapy regime. The nucleic acid construct according to the invention can be introduced into cells by techniques well known in the art which include microinjection of DNA into the nucleus of a cell, transfection, electroporation, lipofection/liposome fusion and particle bombardment. Suitable cells include autologous and non-autologous cells, and may include xenogenic cells.

Method of Treatment

It is an aspect of the present invention to provide a peptide, a nucleic acid construct encoding a peptide according to the present invention, a delivery vehicle comprising a nucleic acid construct encoding a peptide according to the present invention, as well a composition comprising the peptide according to the invention, for use as a medicament.

It is a further aspect of the present invention to provide:
a. a peptide as defined herein,
b. a peptide consisting of 21 to 39 contiguous amino acid residues derived from GIP (SEQ ID NO: 4), wherein said peptide comprises at least the sequence TFISDYSIAMDKIX$_1$QQDFVNW (GIP5-25, SEQ ID NO: 5), wherein $X_1$ is any amino acid, wherein said peptide does not comprise the Tyr amino acid of position 1 of SEQ ID NO: 4, and wherein said peptide does not comprise the Ala amino acid of position 2 of SEQ ID NO: 4, or a functional variant thereof having at least 60% identity to said peptide, or c. a peptide selected from the group consisting of
EGTFISDYSIAMX$_{0a}$X$_{0b}$IX$_1$QQDFVNWLLAQX$_2$ (GIP3-30; SEQ ID NO: 74), GTFISDYSIAMX$_{0a}$X$_{0b}$IX$_1$QQDFVNWLLAQX$_2$ (GIP4-30; SEQ ID NO: 75), TFISDYSIAMX$_{0a}$X$_{0b}$IX$_1$QQDFVNWLLAQX$_2$ (GIP5-30; SEQ ID NO: 76), wherein X$_{0a}$, X$_{0b}$, X$_1$ and X$_2$ are individually any amino acid, or a functional variant thereof having at least 75% sequence identity to said peptide, for use in a method of inhibiting or reducing one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides, and ix) ix) GIP-induced reduction in bone resorption.

It is a further aspect of the present invention to provide:
a. a peptide as defined herein,
b. a peptide consisting of 21 to 39 contiguous amino acid residues derived from GIP (SEQ ID NO: 4), wherein said peptide comprises at least the sequence TFISDYSIAMDKIX$_1$QQDFVNW (GIP5-25, SEQ ID NO: 5), wherein X$_1$ is any amino acid, wherein said peptide does not comprise the Tyr amino acid of position 1 of SEQ ID NO: 4, and wherein said peptide does not comprise the Ala amino acid of position 2 of SEQ ID NO: 4, or a functional variant thereof having at least 60% identity to said peptide, or
c. a peptide selected from the group consisting of
EGTFISDYSIAMX$_{0a}$X$_{0b}$IX$_1$QQDFVNWLLAQX$_2$ (GIP3-30; SEQ ID NO: 74), GTFISDYSIAMX$_{0a}$X$_{0b}$IX$_1$QQDFVNWLLAQX$_2$ (GIP4-30; SEQ ID NO: 75), TFISDYSIAMX$_{0a}$X$_{0b}$IX$_1$QQDFVNWLLAQX$_2$ (GIP5-30; SEQ ID NO: 76), wherein X$_{0a}$, X$_{0b}$, X$_1$ and X$_2$ are individually any amino acid, or a functional variant thereof having at least 75% sequence identity to said peptide, for use in a method of treating metabolic syndrome.

In one embodiment the metabolic syndrome is selected from the group consisting of obesity, obesity-related disorders, pre-diabetes (impaired fasting glucose), diabetes mellitus, diabetes-related disorders, insulin resistance, elevated fasting glucose (hyperglycemia), elevated fasting serum triglyceride level (VLDL triglyceride), low high-density lipoprotein (HDL) levels, fatty acid metabolism disorder, cardiovascular disease, elevated blood pressure and atherosclerosis.

In one embodiment the metabolic syndrome is obesity.

In one embodiment the metabolic syndrome is diabetes mellitus, including diabetes mellitus type I and type II.

In one embodiment the metabolic syndrome is insulin resistance.

In one embodiment the metabolic syndrome is a fatty acid metabolism disorder.

It is a further aspect of the present invention to provide a peptide as defined herein for use in a method of treating cancer.

In one embodiment the cancer is selected from the group consisting of colon cancer, a neuroendocrine cancer and adrenal adenoma.

It is a further aspect of the present invention to provide a peptide as defined herein for use in a method of treating a bone density disorder.

In one embodiment there is provided a peptide as defined herein for use in a method of inhibiting activity of bone cells. In one embodiment there is provided a peptide as defined herein for use in a method of inhibiting (or antagonizing) GIP-induced postprandial reduction in bone resorption. In one embodiment there is provided a peptide as defined herein for use in a method of treating bone cancer.

In one embodiment, the bone density disorder is selected from the group consisting of atherosclerosis, disorders characterized by low bone density and/or reduced bone volume, disorders characterized by high bone density and/or increased bone volume and osteoporosis.

In yet another aspect, the invention relates to the use of such peptides in a method of characterizing or examining aspects of a disorder, and/or characterizing or examining aspects of the human physiology associated with a disorder, wherein said disorder in one embodiment is selected from metabolic disorder or syndrome, such as obesity, diabetes mellitus, insulin resistance or fatty acid metabolism disorder. In other aspects the invention relates to methods of treating cancer, such as colon cancer or adrenal adenoma. In other aspects the invention relates to methods of treating a bone density disorder characterized by high bone density and/or increased bone volume or osteoporosis. In other aspects the invention relates to methods of treating atherosclerosis.

It is another aspect to provide a peptide according to the invention for the manufacture of a medicament.

In one embodiment there is provided the use of a peptide according to the invention in the manufacture of a medicament for inhibiting or reducing one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides and ix) ix) GIP-induced reduction of bone resorption.

Also provided is a method for treating metabolic syndrome such as obesity, diabetes mellitus, insulin resistance or fatty acid metabolism disorder; a cancer such as colon cancer or adrenal adenoma; a bone density disorder, such as bone density disorders characterized by high bone density and/or increased bone volume; or atherosclerosis; said method comprising the step of administering to an individual in need thereof an effective amount of a peptide as defined herein.

An individual in need as referred to herein, is an individual that may benefit from the administration of a peptide or pharmaceutical composition according to the present invention. Such an individual may suffer from a metabolic disorder such as obesity, diabetes, insulin resistance or fatty acid metabolism disorder, a cancer such as colon cancer or adrenal adenoma, a bone density disorder, or be in risk of suffering therefrom. The individual may be any human being, male or female, infant, middle-aged or old. The disorder to be treated or prevented in the individual may relate to the age of the individual, the general health of the individual, the medications used for treating the individual and whether or not the individual has a prior history of suffering from diseases or disorders that may have or have induced a metabolic disorder such as obesity, diabetes, insulin resistance or fatty acid metabolism disorder, a cancer such as colon cancer or adrenal adenoma, atherosclerosis, a bone density disorder. In some embodiments, the disorder to be treated is linked to GIP-induced glucagon secretion, GIP-induced insulin secretion, to GIP-induced somatostatin secretion, to GIP-induced glucose uptake, to GIP-induced fatty acid synthesis and/or fatty acid incorporation, to high expression and/or activity of a GIPR, to release of GIP following a meal; wherein the term "high" is to be construed as referring to levels greater than the corresponding levels observed in individuals not in need of treatment.

Method of Preparation (Peptide)

The peptides according to the present invention may be prepared by any methods known in the art. Thus, the GIP-derived peptides may be prepared by standard peptide-preparation techniques such as solution synthesis or Merrifield-type solid phase synthesis.

In one embodiment, a peptide according to the invention is a non-naturally occurring peptide; being derived from a naturally occurring protein native GIP.

In another embodiment, the peptide according to the invention is a naturally occurring peptide being derived from a naturally occurring protein GIP1-42.

In one embodiment a peptide according to the present invention is purified from a naturally occurring source thereof, such as serum. Protein purification is a series of processes intended to isolate a single type of protein from a complex mixture. The starting material is usually a biological tissue. The various steps in the purification process may free the protein from a matrix that confines it, separate the protein and non-protein parts of the mixture, and finally separate the desired protein from all other proteins. Separation steps may exploit differences in (for example) protein size, physico-chemical properties, binding affinity and biological activity.

In one embodiment a peptide according to the invention is synthetically made or produced.

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

In one embodiment the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Peptides may be synthesised either batch-wise on a fully automated peptide synthesiser using 9-fluorenylmethyloxycarbonyl (Fmoc) or tert-Butyloxycarbonyl (Boc) as N-a-amino protecting group and suitable common protection groups for side-chain functionalities.

After purification such as by reversed phase HPLC, peptides may be further processed to obtain for example cyclic or C- or N-terminal modified isoforms. The methods for cyclization and terminal modification are well-known in the art.

Peptides according to the invention may be synthesized as monomers or multimers such as dimers or tetramers.

Pharmaceutical Composition and Formulation

Whilst it is possible for the bioactive agent of the present invention (a peptide, a nucleic acid construct encoding said peptide, and a composition comprising a peptide) to be administered as the raw chemical (peptide), it is sometimes preferred to present them in the form of a pharmaceutical formulation. Such a pharmaceutical formulation may be referred to as a pharmaceutical composition, pharmaceutically acceptable composition or pharmaceutically safe composition.

Accordingly, the present invention further provides a pharmaceutical formulation, which comprises a bioactive agent of the present invention, or a pharmaceutically acceptable salt or ester thereof, and a pharmaceutically acceptable carrier, excipient and/or diluent. The pharmaceutical formulations may be prepared by conventional techniques, e.g. as described in Remington: The Science and Practice of Pharmacy 2005, Lippincott, Williams & Wilkins.

Pharmaceutically acceptable salts of the instant peptide compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The peptide compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In a preferred embodiment, the peptide according to the invention is formulated as an acetate salt.

The pharmaceutically acceptable salt of the peptide of the invention is preferably in solution with a physiologically acceptable pH, i.e. the solution comprising the peptide salt preferably has a pH acceptable for clinical use. For example, the salt may be diluted in 1 mM HCl and 0.1% human serum albumin (HSA) at pH 3.4 to a final concentration of 1.9 mg/mL. This solution may be further diluted with 0.2% HSA saline to 0.0162 mg/mL and the resulting solution preferably has physiologically acceptable pH. The final concentration of the peptide is preferably 0.2 mM.

In one embodiment, the peptide composition according to the invention may be diluted in a solution with a final concentration of peptide at least 0.05 mM, such as at least 0.1 mM, such as at least 0.2 mM, such as at least 0.3 mM, such as at least 0.4 mM, such as at least 0.5 mM. In a preferred embodiment, the final concentration of the peptide is 0.2 mM.

In another embodiment, the peptide composition according to the invention may be diluted in a solution with a final concentration of peptide of 0.05 to 10 mM, such as 0.05 to 0.1 mM, such as 0.1 to 0.2 mM, such as 0.2 to 0.3 mM, such as 0.3 to 0.4 mM, such as 0.4 to 0.5 mM, such as 0.5 to 0.6 mM, such as 0.6 to 0.7 mM, such as 0.7 to 0.8 mM, such as 0.8 to 0.9 mM, such as 0.9 to 1 mM, such as 1 to 2 mM, such as 2 to 3 mM, such as 3 to 4 mM, such as 4 to 5 mM, such as 5 to 6 mM, such as 6 to 7 mM, such as 7 to 8 mM, such as 8 to 9 mM, such as 9 to 10 mM.

In a preferred embodiment, the peptide is diluted in HSA saline at a final concentration of 0.2 mM, the resulting solution having a physiologically acceptable pH such as pH 6.7.

In one embodiment the pharmaceutical formulation of the present invention has a pH in the range of 5.5 to 8, such as 5.5 to 6, such as 6 to 6.5, for example 6.5 to 7, such as 7 to 7.5, for example 7.5 to 8.

Administration and Dosage

According to the present invention, a peptide or a nucleic acid construct encoding said peptide, or a composition comprising a peptide as defined herein is administered to individuals in need of treatment in pharmaceutically effective doses or a therapeutically effective amount. The dosage requirements will vary with the particular drug composition employed, the route of administration and the particular subject being treated, which depend on the severity and the sort of the disorder as well as on the weight and general state of the subject. It will also be recognized by one skilled in the art that the optimal quantity and spacing of individual dosages of a peptide compound will be determined by the nature and extent of the condition being treated, the form, route and site of administration, and the particular patient being treated, and that such optima can be determined by conventional techniques. It will also be appreciated by one of skill in the art that the optimal course of treatment, i.e., the number of doses of a compound given per day for a defined number of days, can be ascertained using conventional course of treatment determination tests.

In one embodiment of the present invention, the bioactive agent is administered at least once daily, such as once daily, such as twice daily, such as thrice daily, such as four times daily, such as five times daily.

A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

In one embodiment of the present invention, the bioactive agent is administered in doses of at least 30000 pmol/kg/day, such as at least 60000 pmol/kg/day, such as at least 72000 pmol/kg/day, such as at least 90000 pmol/kg/day, such as at least 120000 pmol/kg/day, such as at least 150000 pmol/kg/day, such as at least 30000 pmol/kg/day, preferably such as at least 60000 pmol/kg/day. In a particular embodiment, the bioactive agent is administered at a dosage of 72000 pmol/kg/day.

In one embodiment, the bioactive agent is administered at a daily dosage of 30000 pmol/kg to 40000 pmol/kg, such as 40000 pmol/kg to 50000 pmol/kg, such as 50000 pmol/kg to 60000 pmol/kg, such as 60000 pmol/kg to 70000 pmol/kg, such as 70000 pmol/kg to 80000 pmol/kg, such as 80000 pmol/kg to 90000 pmol/kg, such as 90000 pmol/kg to 100000 pmol/kg, such as 100000 pmol/kg to 110000 pmol/kg, such as 110000 pmol/kg to 120000 pmol/kg. In a particular embodiment, the bioactive agent is a peptide and is administered at a daily dose of 60000 pmol/kg or 72000 pmol/kg.

In one embodiment of the present invention, the bioactive agent is administered by infusion. In one embodiment, the bioactive agent is a peptide, and the infusion takes place over a duration of at least 15 min, such as at least 20 min, such as at least 30 min, such as at least 40 min, such as at least 50 min, such as at least 60 min, such as at least 90 min, such as at least 120 min, preferably such as 60 min.

In one embodiment of the present invention, the bioactive agent is administered over a duration between 15 and 120 min, such as between 15 and 20 min, such as between 20 and 30 min, such as between 30 and 40 min, such as between 40 and 50 min, such as between 50 and 60 min, such as between 60 and 90 min, such as between 90 and 120 min.

In one embodiment, the bioactive agent is administered once daily over a duration of 60 min, or twice daily over a duration of 30 min, or thrice daily over a duration of 20 min, or four times daily over a duration of 15 min, or five times daily over a duration of 12 min, where the duration is the duration of each individual administration.

In one embodiment, the bioactive agent is administered at a dosage of at least 500 pmol/kg/min, such as at least 1000 pmol/kg/min, such as at least 1200 pmol/kg/min, such as at least 1500 pmol/kg/min, such as at least 2000 pmol/kg/min, such as at least 2500 pmol/kg/min, such as at least 5000 pmol/kg/min.

The skilled person knows that if the number of daily administrations is increased, the dose to be administered in each administration may be decreased accordingly. Likewise, if the duration of each administration is decreased, the dosage may be increased accordingly.

The bioactive agent to be administered is a peptide according to the present invention. In preferred embodiments, the peptide is hGIP3-30 (SEQ ID NO: 1), rGIP3-30 (SEQ ID NO: 2) or mGIP3-30 (SEQ ID NO: 3), or a functional variant thereof.

In one embodiment the bioactive agent is administered with one or more additional active ingredients. These other ingredients may be pharmaceutically active. In some embodiments, the bioactive agent is a peptide as defined above and the other ingredient is hGIP1-42 (SEQ ID NO: 66) or a variant thereof. In some embodiments, hGIP1-42 is administered at a dosage of at least 120 pmol/kg/day, such as at least 130 pmol/kg/day, such as at least 140 pmol/kg/day, such as at least 150 pmol/kg/day, such as at least 160 pmol/kg/day, such as at least 170 pmol/kg/day, such as at least 180 pmol/kg/day, such as at least 190 pmol/kg/day, such as at least 200 pmol/kg/day. In a preferred embodiment, hGIP1-42 is administered at a dosage of 120 pmol/kg/day. In another preferred embodiment, the bioactive agent is hGIP3-30 (SEQ ID NO: 1), rGIP3-30 (SEQ ID NO: 2) or mGIP3-30 (SEQ ID NO: 3), or a functional variant thereof and the other ingredient is hGIP1-42 (SEQ ID NO: 65). In a preferred embodiment, the bioactive agent is hGIP3-30 (SEQ ID NO: 1), or a functional variant thereof and the other ingredient is hGIP1-42 (SEQ ID NO: 65) administered at a dosage of at least 120 pmol/kg/day.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

For systemic treatment according to the present invention the route of administration is capable of introducing the bioactive agent (a peptide, a nucleic acid construct encoding said peptide, and a composition comprising a peptide according to the present invention) into the blood stream to ultimately target the sites of desired action.

Such routes of administration are any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intracerebral, intravenous and intradermal administration).

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the bioactive agent may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

Local Treatment

The bioactive agent according to the invention may in one embodiment be used as a local treatment, i.e. be introduced directly to the site(s) of action. Accordingly, the bioactive agent may be applied to the skin or mucosa directly, or the bioactive agent may be injected into the site of action, for example into the diseased tissue or to an end artery leading directly to the diseased tissue.

These administration forms preferably avoid the blood brain barrier.

Kit-of-Parts

The present invention also relates to a kit-of-parts comprising one or more of the bioactive agents described above (a peptide, a nucleic acid construct or a composition), and at least one additional or further component.

A kit of parts according to the present invention comprises one or more of the bioactive agents as defined herein for treatment, prevention or alleviation of a metabolic disorder such as obesity or diabetes mellitus, a bone density disorder or cancer. Kits according to the present invention allows for simultaneous, sequential or separate administration of the bioactive agent according to the present invention and/or one or more second active ingredients as described herein elsewhere.

Items

1. A peptide consisting of 21 to 39 contiguous amino acid residues derived from gastric inhibitory peptide (GIP) (SEQ ID NO: 4),
   wherein said peptide comprises at least the sequence TFISDYSIAMDKIX$_1$QQDFVNW (GIP5-25, SEQ ID NO: 5),
   wherein X$_1$ is any amino acid,
   wherein said peptide does not comprise the Tyr amino acid of position 1 of SEQ ID NO: 4, and wherein said peptide does not comprise the Ala amino acid of position 2 of SEQ ID NO: 4,
   or a functional variant thereof having at least 60% identity to said peptide.
2. The peptide according to claim 1, wherein said peptide is non-naturally occurring.
3. The peptide according to any one of the preceding items, wherein said peptide is synthetic.

4. The peptide according to any one of the preceding items, wherein said peptide is selected from the group consisting of:

```
                                    (GIP3-25, SEQ ID NO: 6)
EGTFISDYSIAMDKIX₁QQDFVNW, (GIP3-26, SEQ ID NO: 7)
EGTFISDYSIAMDKIX₁QQDFVNWL, (GIP3-27, SEQ ID NO: 8)
EGTFISDYSIAMDKIX₁QQDFVNWLL, (GIP3-28, SEQ ID NO: 9)
EGTFISDYSIAMDKIX₁QQDFVNWLLA, (GIP3-29, SEQ ID NO: 10)
EGTFISDYSIAMDKIX₁QQDFVNWLLAQ, (GIP3-30, SEQ ID NO: 11)
EGTFISDYSIAMDKIX₁QQDFVNWLLAQX₂, (GIP3-31, SEQ ID NO: 12)
EGTFISDYSIAMDKIX₁QQDFVNWLLAQX₂G, (GIP3-32, SEQ ID NO: 13)
EGTFISDYSIAMDKIX₁QQDFVNWLLAQX₂GK, (GIP3-33, SEQ ID NO: 14)
EGTFISDYSIAMDKIX₁QQDFVNWLLAQX₂GKK, (GIP3-34, SEQ ID NO: 15)
EGTFISDYSIAMDKIX₁QQDFVNWLLAQX₂GKKN, (GIP3-35, SEQ ID NO: 16)
EGTFISDYSIAMDKIX₁QQDFVNWLLAQX2GKKND, (GIP3-36, SEQ ID NO: 17)
EGTFISDYSIAMDKIX₁QQDFVNWLLAQX₂GKKNDW, (GIP3-37, SEQ ID NO: 18)
EGTFISDYSIAMDKIX₁QQDFVNWLLAQX₂GKKNDWK, (GIP3-38, SEQ ID NO: 19)
EGTFISDYSIAMDKIX₁QQDFVNWLLAQX₂GKKNDWKH, (GIP3-39, SEQ ID NO: 20)
EGTFISDYSIAMDKIX₁QQDFVNWLLAQX₂GKKNDWKHN, (GIP3-40, SEQ ID NO: 21)
EGTFISDYSIAMDKIX₁QQDFVNWLLAQX₂GKKNDWKHNI, (GIP3-41, SEQ ID NO: 22)
EGTFISDYSIAMDKIX₁QQDFVNWLLAQX₂GKKNDWKHNIT,
``` or a functional variant thereof, wherein X$_1$ and X$_2$ are individually any amino acid.

5. The peptide according to any one of the preceding items, wherein said peptide is EGTFISDYSIAMDKIX$_1$QQDFVNWLLAQX$_2$ (GIP3-30, SEQ ID NO: 11), or variants thereof.

6. The peptide according to any one of the preceding items, wherein said peptide is selected from the group consisting of:

```
                                    (GIP4-25, SEQ ID NO: 23)
GTFISDYSIAMDKIX₁QQDFVNW, (GIP4-26, SEQ ID NO: 24)
GTFISDYSIAMDKIX₁QQDFVNWL, (GIP4-27, SEQ ID NO: 25)
GTFISDYSIAMDKIX₁QQDFVNWLL, (GIP4-28, SEQ ID NO: 26)
GTFISDYSIAMDKIX₁QQDFVNWLLA,
```

-continued

```
                         (GIP4-29, SEQ ID NO: 27)
GTFISDYSIAMDKIX₁QQDFVNWLLAQ, (GIP4-30, SEQ ID NO: 28)
GTFISDYSIAMDKIX₁QQDFVNWLLAQX₂, (GIP4-31, SEQ ID NO: 29)
GTFISDYSIAMDKIX₁QQDFVNWLLAQX₂G, (GIP4-32, SEQ ID NO: 30)
GTFISDYSIAMDKIXVQQDFVNWLLAQX₂GK, (GIP4-33, SEQ ID NO: 31)
GTFISDYSIAMDKIX₁QQDFVNWLLAQX₂GKK, (GIP4-34, SEQ ID NO: 32)
GTFISDYSIAMDKIX₁QQDFVNWLLAQX₂GKKN, (GIP4-35, SEQ ID NO: 33)
GTFISDYSIAMDKIX₁QQDFVNWLLAQX₂GKKND, (GIP4-36, SEQ ID NO: 34)
GTFISDYSIAMDKIX₁QQDFVNWLLAQX₂GKKNDW, (GIP4-37, SEQ ID NO: 35)
GTFISDYSIAMDKIX₁QQDFVNWLLAQX₂GKKNDWK, (GIP4-38, SEQ ID NO: 36)
GTFISDYSIAMDKIX₁QQDFVNWLLAQX₂GKKNDWKH, (GIP4-39, SEQ ID NO: 37)
GTFISDYSIAMDKIX₁QQDFVNWLLAQX₂GKKNDWKHN, (GIP4-40, SEQ ID NO: 38)
GTFISDYSIAMDKIX₁QQDFVNWLLAQX₂GKKNDWKHNI, (GIP4-41, SEQ ID NO: 39)
GTFISDYSIAMDKIX₁QQDFVNWLLAQX₂GKKNDWKHNIT, (GIP4-42, SEQ ID NO: 40)
GTFISDYSIAMDKIX₁QQDFVNWLLAQX₂GKKNDWKHNITQ,
``` or a functional variant thereof, wherein $X_1$ and $X_2$ are individually any amino acid.

7. The peptide according to any one of the preceding items, wherein said peptide is selected from the group consisting of:

```
                         (GIP5-25, SEQ ID NO: 5)
TFISDYSIAMDKIX₁QQDFVNW, (GIP5-26, SEQ ID NO: 41)
TFISDYSIAMDKIX₁QQDFVNWL, (GIP5-27, SEQ ID NO: 42)
TFISDYSIAMDKIX₁QQDFVNWLL, (GIP5-28, SEQ ID NO: 43)
TFISDYSIAMDKIX₁QQDFVNWLLA, (GIP5-29, SEQ ID NO: 44)
TFISDYSIAMDKIX₁QQDFVNWLLAQ, (GIP5-30, SEQ ID NO: 45)
TFISDYSIAMDKIX₁QQDFVNWLLAQX₂, (GIP5-31, SEQ ID NO: 46)
TFISDYSIAMDKIX₁QQDFVNWLLAQX₂G, (GIP5-32, SEQ ID NO: 47)
TFISDYSIAMDKIX₁QQDFVNWLLAQX₂GK, (GIP5-33, SEQ ID NO: 48)
TFISDYSIAMDKIX₁QQDFVNWLLAQX₂GKK, (GIP5-34, SEQ ID NO: 49)
TFISDYSIAMDKIX₁QQDFVNWLLAQX₂GKKN, (GIP5-35, SEQ ID NO: 50)
TFISDYSIAMDKIX₁QQDFVNWLLAQX₂GKKND, (GIP5-36, SEQ ID NO: 51)
TFISDYSIAMDKIX₁QQDFVNWLLAQX₂GKKNDW, (GIP5-37, SEQ ID NO: 52)
TFISDYSIAMDKIX₁QQDFVNWLLAQX₂GKKNDWK, (GIP5-38, SEQ ID NO: 53)
TFISDYSIAMDKIX₁QQDFVNWLLAQX₂GKKNDWKH (GIP5-39, SEQ ID NO: 54)
TFISDYSIAMDKIX₁QQDFVNWLLAQX₂GKKNDWKHN, (GIP5-40, SEQ ID NO: 55)
TFISDYSIAMDKIX₁QQDFVNWLLAQX₂GKKNDWKHNI, (GIP5-41, SEQ ID NO: 56)
TFISDYSIAMDKIX₁QQDFVNWLLAQX₂GKKNDWKHNIT, (GIP5-42, SEQ ID NO: 57)
TFISDYSIAMDKIX₁QQDFVNWLLAQX₂GKKNDWKHNITQ,
``` or a functional variant thereof, wherein $X_1$ and $X_2$ are individually any amino acid.

8. The peptide according to any one of the preceding items, wherein $X_1$ is selected from the group consisting of Ala, His, Arg and Lys.

9. The peptide according to any one of the preceding items, wherein $X_2$ is selected from the group consisting of Ala, Lys and Arg.

10. The peptide according to any one of the preceding items, wherein $X_1$ is selected from the group consisting of His and Arg and $X_2$ is Arg.

11. The peptide according to any one of the preceding items, wherein $X_1$ is His and $X_2$ is Lys.

12. The peptide according to any one of the preceding items, wherein $X_1$ is Arg and $X_2$ is Lys or Arg.

13. The peptide according to any one of the preceding items, wherein said peptide is selected from the group consisting of EGTFISDYSIAMDKIHQQDFVNWLLAQK (hGIP3-30, SEQ ID NO: 1), EGTFISDYSIAMD-KIRQQDFVNWLLAQK (rGIP3-30, SEQ ID NO: 2), EGTFISDYSIAMDKIRQQDFVNWLLAQR (mGIP3-30, SEQ ID NO: 3), and variants thereof.

14. The peptide according to any one of the preceding items, wherein said peptide is hGIP3-30 (SEQ ID NO: 1) or a variant thereof.

15. The peptide according to any one of the preceding items, wherein said peptide is rGIP3-30/hGIP(3-30)H18R (SEQ ID NO: 2) or a variant thereof.

16. The peptide according to any one of the preceding items, wherein said peptide is mGIP3-30/hGIP(3-30)H18R/K30R (SEQ ID NO: 3) or a variant thereof.

17. The peptide according to any one of the preceding items, wherein said peptide is amidated.

18. The peptide according to any one of the preceding items, wherein said peptide has at least 60% identity, such as at least 65% identity, such as at least 70% identity, such as at least 75% identity, such as at least 80% identity, such as at least 85% identity, such as at least 90% identity, such as at least 95% identity, such as at least 99% identity, such as 100% identity to hGIP3-30 (SEQ ID NO: 1) and/or the corresponding part of hGIP (SEQ ID NO:65).

19. The peptide according to any one of the preceding items, wherein said peptide comprises the sequence TFISDYSIAMX$_{0a}$X$_{0b}$IX$_1$QQDFVNW, wherein X$_{0a}$ and/or X$_{0b}$ are individually any amino acid.

20. The peptide according to any one of the preceding items, wherein wherein D at position 15 ($X_{0a}$) and/or K at position 16 ($X_{0b}$) is substituted with a different amino acid, such as A (Ala).
21. The peptide according to any one of the preceding items, wherein said peptide consists of 21 to 22 amino acids, for example 22 to 23, such as 23 to 24, for example 24 to 25, such as 25 to 26, for example 26 to 27, such as 27 to 28, for example 28 to 29, such as 29 to 30, for example 30 to 31, such as 31 to 32, for example 32 to 33, such as 33 to 34, for example 34 to 35, such as 35 to 36, for example 36 to 37, such as 37 to 38, for example 38 to 39 contiguous amino acids.
22. The peptide according to any one of the preceding items, wherein said peptide binds to and/or is an antagonist of one or more GIP-receptors (GIPRs), such as one or more of the human GIPR (Uniprot accession number P48546), the rat GIPR (Uniprot accession number P43219) and the murine GIPR (Uniprot accession number Q0P543).
23. The peptide according to any one of the preceding items, wherein said peptide is a competitive antagonist, an uncompetitive antagonist, a non-competitive antagonist, a silent antagonist, a partial agonist or an inverse agonist of one or more GIP-receptors (GIPRs), such as one or more of the human GIPR (Uniprot accession number P48546), the rat GIPR (Uniprot accession number P43219) and the murine GIPR (Uniprot accession number Q0P543).
24. The peptide according to item 23, wherein said peptide is a competitive antagonist of one or more GIP-receptors (GIPRs).
25. The peptide according to any one of the preceding items, wherein said peptide has a Ki of at least 1 nM, such as at least 5 nM, such as at least 10 nM, such at least 15 nM, such as 20 nM, such as at least 25 nM, such as 30 nM, such as at least 35 nM, such as 40 nM, such as at least 45 nM, such as at least 50 nM, such as at least 55 nM.
26. The peptide according to any one of the preceding items, wherein said peptide has an affinity for a GIPR which is higher than the affinity of GIP3-42 (SEQ ID NO: 58) for the same GIPR, such as wherein said peptide has an affinity for the hGIPR which is higher than the affinity of hGIP3-42 (SEQ ID NO: 62) for the hGIPR.
27. The peptide according to any one of the preceding items, wherein said peptide is capable of displacing hGIP1-42 (SEQ ID NO: 65) from the hGIPR, such as displacing hGIP1-42 with an IC50 value of at least 0.5 nM, such as at least 1 nM, such as at least 2 nM, such as at least 3 nM, such as at least 4 nM, such as at least 5 nM, such as at least 5.2 nM, such as at least 6 nM, such as at least 7 nM, such as at least 7.8 nM, such as at least 8 nM, such as at least 9 nM, such as at least 10 nM, such as at least 11 nM, such as at least 11.4 nM, such as at least 12 nM, such as at least 13 nM, such as at least 14 nM, such as at least 15 nM, such as at least 16 nM.
28. The peptide according to any one of the preceding items, wherein said peptide is capable of inhibiting and/or antagonising somatostatin secretion induced by hGIP1-42 (SEQ ID NO: 65).
29. The peptide according to any one of the preceding items, wherein said peptide is capable of inhibiting and/or antagonising insulin secretion induced by hGIP1-42 (SEQ ID NO: 65).
30. The peptide according to any one of the preceding items, wherein said peptide is capable of inhibiting and/or antagonising glucagon secretion induced by hGIP1-42 (SEQ ID NO: 65).
31. A nucleic acid construct encoding a peptide according to any one of items 1 to 31.
32. A delivery vehicle comprising the nucleic acid construct according to item 32.
33. A cell comprising the nucleic acid construct according to item 32.
34. A pharmaceutically acceptable composition comprising a peptide according to any one of items 1 to 31.
35. The composition according to item 35, said composition comprising said peptide formulated as an acetate salt.
36. The composition according to any one of items 35 to 38, wherein said peptide is diluted in human serum albumin saline.
37. The composition according to any one of items 35 to 39, wherein the pH of the composition is acceptable for clinical use.
38. The composition according to any one of items 35 to 40, wherein said peptide is diluted in HSA saline at a final concentration of 0.2 mM, the resulting solution having a pH of about 6.7.
39. A method of inhibiting one or more of o) GIP-induced glucagon secretion, i) GIP-induced insulin secretion, ii) GIP-induced somatostatin secretion, iii) GIP-induced glucose uptake, iv) GIP-induced fatty acid synthesis and/or fatty acid incorporation, v) high or increased expression or activity of a GIPR and vi) release of GIP following a meal (post-prandial GIP release), said method comprising administering to an individual in need thereof an effective amount of a peptide, a nucleic acid construct, or a composition according to any one of the preceding items.
40. The peptide, the nucleic acid construct, or the composition according to any one of the preceding items for use as a medicament.
41. The peptide, the nucleic acid construct, or the composition according to any one of the preceding items for use in a method of treating metabolic disorders.
42. The peptide, the nucleic acid construct, or the composition according to any one of the preceding items, wherein the metabolic disorder is selected from the group consisting of obesity, diabetes mellitus, insulin resistance, atherosclerosis, and fatty acid metabolism disorder.
43. The peptide, the nucleic acid construct, or the composition according to any one of the preceding items for use in a method of reducing serum levels of free fatty acids and/or serum levels of triglycerides.
44. The peptide, the nucleic acid construct, or the composition according to any one of the preceding items for use in a method of treating cancer, such as a cancer selected from the group consisting of colon cancer, a neuroendocrine cancer and adrenal adenoma.
45. The peptide, the nucleic acid construct, or the composition according to any one of the preceding items for use in a method of treating a bone density disorder.
46. The peptide, the nucleic acid construct, or the composition according to any one of the preceding items, wherein the bone density disorder is selected from the group consisting of disorders characterized by low bone density and/or reduced bone volume, disorders characterized by high bone density and/or increased bone volume, and osteoporosis.
47. The peptide, the nucleic acid construct, or the composition for use according to any one of the preceding items, wherein said peptide, nucleic acid construct or composition is to be administered at least once daily, such as once daily.
48. The peptide for use according to any of the preceding items, wherein said peptide is to be administered at a dosage of at least 500 pmol/kg/min, such as at least 1000 pmol/kg/min, such as at least 1200 pmol/kg/min, such as at least 1500 pmol/kg/min, such as at least 2000 pmol/kg/min, such as at least 2500 pmol/kg/min, such as at least 5000 pmol/kg/min.
49. The peptide for use according to any of the preceding items, wherein said peptide is to be administered at a dosage of 500 to 5000 pmol/kg/min, such as 500 to 1000 pmol/kg/min, such as 1000 to 1500 pmol/kg/min, such as 1500 to 2000 pmol/kg/min, such as 2000 to 2500 pmol/kg/min, such as 2500 to 3000 pmol/kg/min, such as 3000 to 4000 pmol/kg/min, such as 4000 to 5000 pmol/kg/min.
50. The peptide for use according to any of the preceding items, wherein said peptide is to be administered at a daily dosage of at least 30000 pmol/kg, such as at least 60000 pmol/kg, such as at least 72000 pmol/kg, such as at least 90000 pmol/kg, such as at least 120000 pmol/kg, such as at least 150000 pmol/kg.
51. The peptide for use according to any of the preceding items, wherein said peptide is to be administered by infusion.
52. A kit of parts comprising a peptide, a nucleic acid construct or a composition according to any of the preceding items, and at least one additional component.

EXAMPLES

Example 1—Materials and Methods

Materials

Human GIP was purchased from Bachem (H5645) Rat-GIP (027-12), while the remaining ligands were synthesized by Caslo™, Lyngby, Denmark. cDNA of the human GIP receptor was purchased from Origene (SC110906) and cloned into the pCMV-Script vector. Iodinated human GIP was purchased from PerkinElmer Life Sciences (NEX402025UC).

Animals

Male Wistar rats (220-250 g) were purchased from Charles River Laboratories more than 1 week before the experiments were performed, and given free access to standard rodent chow and water. Animals were housed two per cage and were subjected to a 12:12 h light-dark cycle.

Transfections and Tissue Culture

COS-7 cells were cultured at 10% CO2 and 37° C. in Dulbecco's modified Eagle's medium 1885 supplemented with 10% fetal bovine serum, 2 mM glutamine, 180 units/ml penicillin, and 45 g/ml streptomycin. Transient transfection of the COS-7 cells for cAMP accumulation and competition binding was performed using the calcium phosphate precipitation method with the addition of chloroquin[46, 47].

cAMP Assay

In white 96-well plates transient transfected COS-7 cells were seeded out in a density of $3*10^4$/well. The day after, the cells were washed twice with Hepes buffered saline (HBS) buffer and incubated with HBS and 1 mM 3-isobutyl-1-methylxanthine (IBMX) for 30 min at 37° C. To test agonists, ligands were added and incubated for 30 min at 37° C. In order to test for antagonistic properties, the antagonist was preincubated for 10 min and then the agonist was added and incubated for 20 additional min. The HitHunter™ cAMP XS assay (DiscoveRx) was carried out according to the manufacturer's instructions.

125I-human GIP Competition Binding Assay

COS-7 cells were seeded in clear 96-well plates the day after transfection using a number of cells/well that obtained 5-10% specific binding of the added radioactive ligand. The following day, cells were assayed by competition binding for 4 h at 4° C. using 15-40 pM 125 I-human GIP as well as unlabeled ligand in 50 mM Hepes buffer (pH 7.2) with 0.5% bovine serum albumin (BSA). After incubation, the cells were washed twice in ice-cold binding buffer and lysed using 200 mM NaOH with 1% SDS for 30 min. Nonspecific binding was determined as the binding of tracer to untransfected cells.

Isolated Perfused Rat or Mouse Pancreas

Non-fasted rats were anaesthetized with an IP injection of Hypnorm/Dormicum and the pancreas was dissected and perfused in situ. Briefly, the rat was killed by removal of the heart, and the pancreas perfused in a single-pass system through both the coeliac and the superior mesenteric artery via a catheter inserted into the adjacent abdominal aorta. All other aortic branches were ligated. The venous effluent was collected for 1 min intervals via an obstructing cannula inserted into the portal vein, and stored at −20° C. until analysis. The flow rate was kept constant at 4 ml/min. The perfusion medium was continuously gassed with a 95% $O_2$/5% $CO_2$ mixture to achieve pH 7.4, and maintained at 37° C. during the entire experiment.

Hormone Analysis

Pancreatic somatostatin concentrations in venous effluent were analysed by RIA. Somatostatin immunoreactivity was determined using antiserum 1758, which was raised in rabbits against synthetic cyclic somatostatin and recognizes both somatostatin-14 and somatostatin-28 [37, 38].

Example 2—GIP(1-30) is Found in T2DM Plasma Following a Meal

Figure 2:
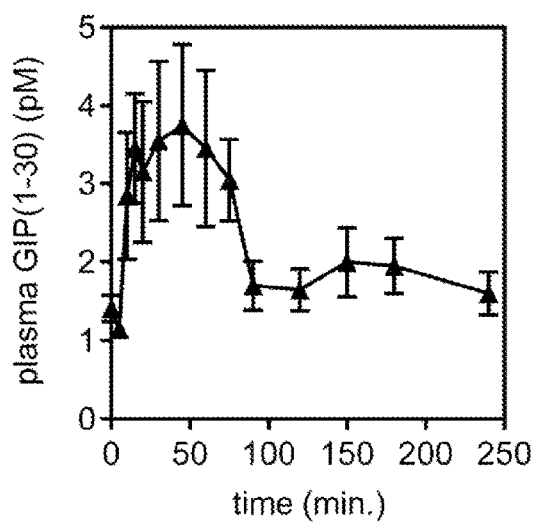
FIG. 2. Meal induced hGIP(1-30) response in T2DM patients. Plasma GIP(1-30) (SEQ ID NO:69) levels were measured from T2DM patients following indigestion of a mixed-meal. Measurements of GIP(1-30) were conducted using a radioimmunoassay with no cross-reactivity with GIP(1-42) (SEQ ID NO: 65). Data are mean±SEM, n=10.

To verify if hGIP1-30 is indeed in human plasma, patients with T2DM were given a meal and hGIP1-30 was measured (FIG. 2). Compared to the meal induced GIP1-42 response in T2DM patients[48] the hGIP(1-30) response displays accelerated kinetics, however at a much lower concentration. Nevertheless, there is a clear hGIP1-30 response to a meal.

Example 3—Discovery of High Affinity Ligands of the hGIPR

Figure 3:
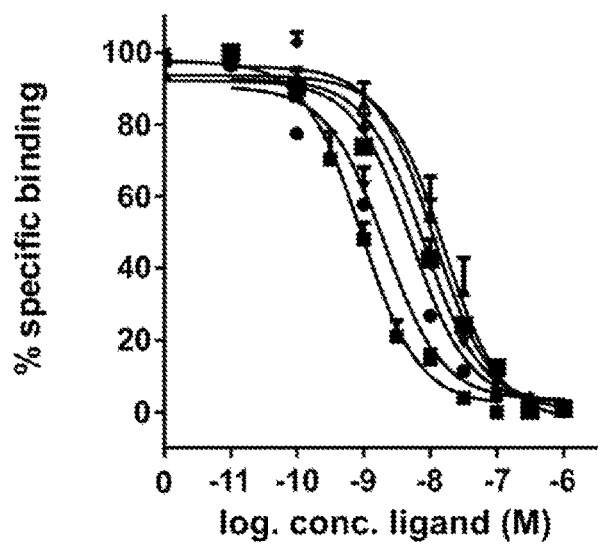
FIG. 3. Competition binding with $^{125}$I-labeled hGIP. The binding of $^{125}$I-labeled hGIP to the transiently transfected COS-7 cells with hGIPR cDNA, was tested in a binding assays vs hGIP(1-42) (SEQ ID NO: 65) (■), GIP(3-30) H18A (SEQ ID NO:79) (•), GIP(3-30)H18R (SEQ ID NO: 2) (▼), GIP(3-30)H18K (SEQ ID NO:80) (■), GIP(3-30) H18R+K30R (SEQ ID NO:3) (♦), hGIP(3-30) (SEQ ID NO: 1) (▲). The data was normalized to maximal specific binding and shown as mean±SEM, n≥3.

In order to investigate the binding properties of variations of the hGIP3-30, heterologous competition binding experiments were conducted and compared to that of hGIP1-42. As seen in FIG. 3, the tested variations of hGIP3-30 were able to displace $^{125}$I-labeled hGIP with IC50 values of 2 nM, 5.2 nM, 7.8 nM, 11.4 nM, and 16 nM (hGIP3-30-H18A, hGIP3-30-H18R, hGIP3-30-H18K, hGIP3-30-H18R+K30R, hGIP3-30, respectively). When compared with the IC50 value of 0.92 for homologues competition binding of hGIP, it is apparent that these are high affinity ligands of the hGIPR.

Example 4—Variants of GIP(3-30) are High Affinity Competitive Antagonists

Figure 4:
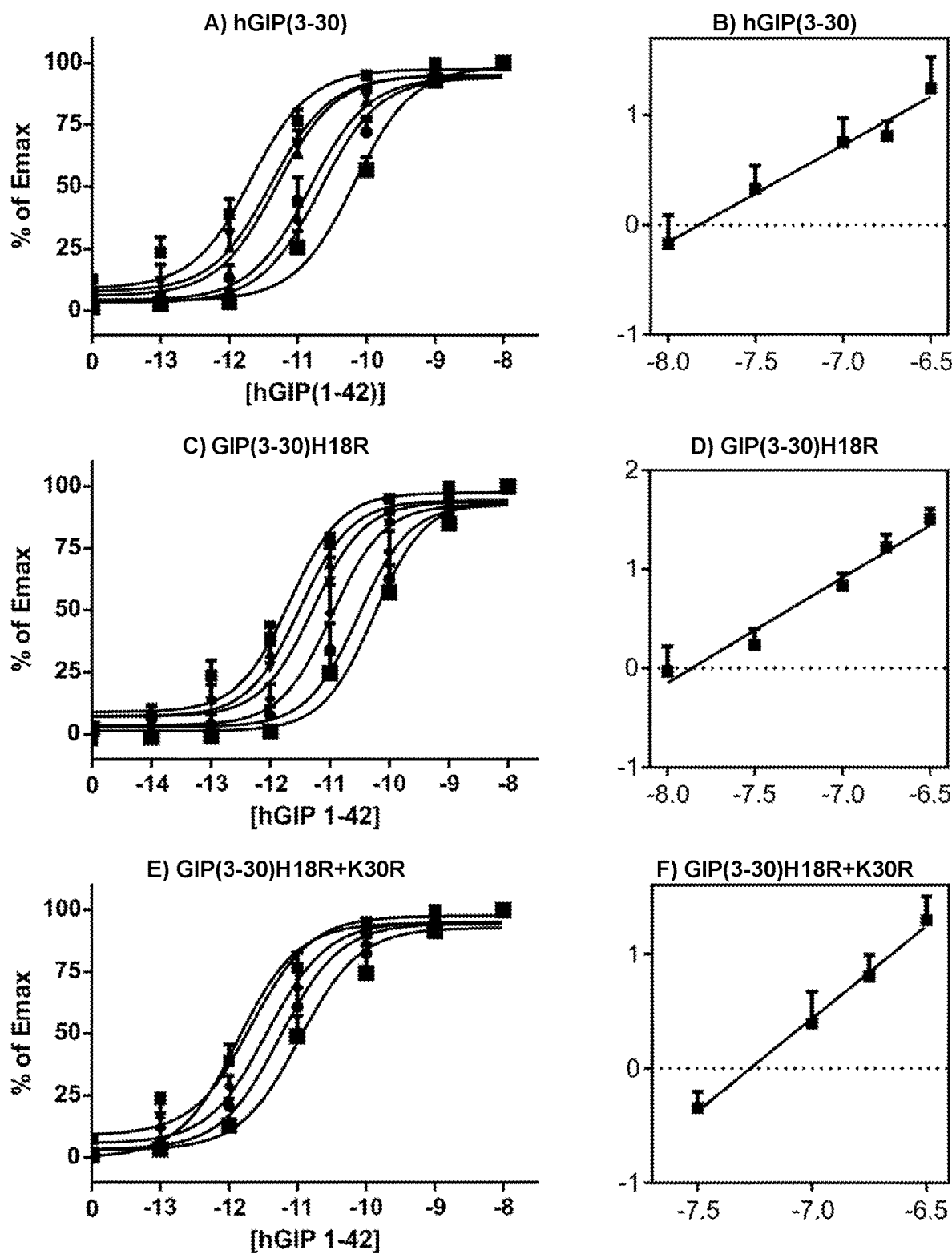
FIG. 4. Schild plot analysis of GIP(3-30) variants on the hGIPR. hGIP(1-42) (SEQ ID NO: 65) induced cAMP accumulation dose-response curves with increasing concentrations of hGIP(3-30) (SEQ ID NO: 1) (A), GIP(3-30)H18R (SEQ ID NO: 2) (C), and GIP(3-30)H18R+K30R (SEQ ID NO: 3) (E). 0 nM (○), 17.8 nM (*), 31.6 nM (▼), 56.2 nM (♦), 100 nM (•), 178 nM (■), and 316 nM (▲). The data was normalized to Emax of each curve and shown as mean±SEM, n≥3. Nonlinear regression was used to calculate EC50 values. Schild plot analysis of the dose-response curves for hGIP(3-30) (SEQ ID NO: 1) (B), GIP(3-30)H18R (SEQ ID NO: 2) (D), and GIP(3-30)H18R+K30R (SEQ ID NO: 3) (F). The x-axis intersect demonstrates a Ki of 15 nM, 14 nM, and 54 nM, respectively.

In order to evaluate potential antagonistic properties, hGIP1-42 induced cAMP dose-response curves were made with increasing concentrations of the GIP3-30 variants and the corresponding Schild plot analysis was made. As seen in FIG. 4A/C/E, there are rightward shifts of hGIP1-42-mediated cAMP response clearly displaying antagonistic characteristics. The linearity of the Schild plot analyses in FIG. 4B/D/F, demonstrate a competitive nature of the GIP3-30 variants with corresponding Ki values of 15 nM, 14 nM, and 54 nM for hGIP3-30, GIP3-30-H18R, and GIP3-30-H18R+K30R, respectively.

Figure 5:
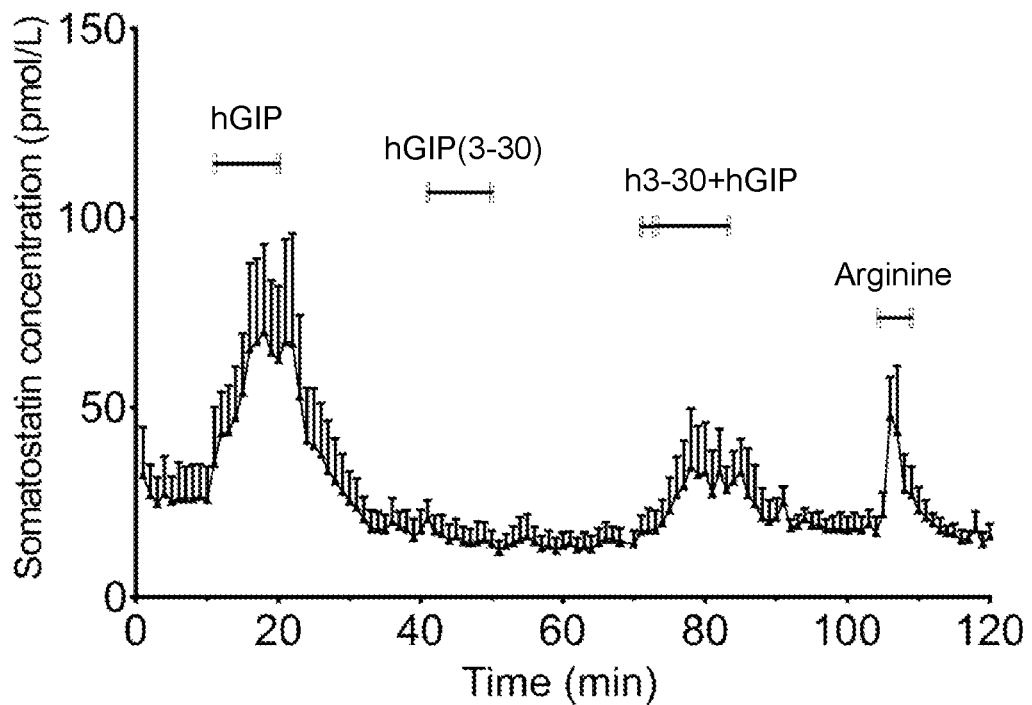
FIG. 5. Antagonism of hGIP induced somatostatin secretion by hGIP(3-30). Somatostatin secretion following stimulation of perfused rat pancreata by either, 1 nM hGIP (SEQ ID NO: 65), 100 nM h0GIP(3-30) (SEQ ID NO: 1), a preincubation with 100 nM hGIP(3-30) (SEQ ID NO: 1) followed by 1 nM hGIP (SEQ ID NO: 65), or arginine (n=3). The glucose concentration was 7 mM and data are mean±SEM.

Example 5—hGIP(3-30) Antagonizes hGIP Induced Somatostatin Secretion in Perfused Rat Pancreata Using perfused rat pancreata, it was demonstrated that hGIP3-30 was capable of antagonizing somatostatin secretion induced by hGIP1-42 (FIG. 5). hGIP1-42 alone induced a robust somatostatin secretion while rGIP3-30 displayed a negligible response. Preincubation with hGIP3-30 before the addition of hGIP1-42 led to a significantly reduced somatostatin release, displaying in vivo efficacy.

Here we show that GIP1-30 is found under physiological conditions following a mixed meal in T2DM patients, underlining the potential of the naturally occurring antagonist, GIP3-30 in humans. Our binding experiments demonstrate that the tested variations of hGIP3-30 have a high affinity for the hGIPR. Of the functionally tested variations, hGIP3-30 and hGIP3-30-H18R are the most promising antagonist candidates. In perfused rat pancreata both antagonists displayed attenuation of GIP induced somatostatin release.

Example 6—Formulation of hGIP3-30 (Acetate Salt) for Clinical Use

The peptide was ordered from Polypeptide laboratories and was formulated as an acetate salt. For clinical use it is needed in solution with a physiological pH. To achieve this 1 mM HCl, 0.1% human serum albumin (HSA) (3.4 pH) was added to the final concentration 1.9 mg/ml of hGIP3-30. A further dilution with 0.2% HSA saline to 0,0162 mg/ml, was done to approximate the concentrations needed in the clinic. This resulted in a pH of 6.67, which is acceptable for clinical use. In order to verify that no hGIP3-30 is lost following filtering and/or freezing-cycles, hGIP3-30 concentrations were measured using a radio immunoassay following various setups of filtering and/or freezing. Following solubility optimization, the hGIP3-30 is sent to the hospital pharmacy formulation. hGIP3-30 in solution are aliquoted into 3 ml vials with the final concentration of 0.2 mM. Finally, the patients receive 1000 pmol/kg/min over an hour's duration.

Example 7—Characterization of hGIP Truncations

GIP(1-30)NH$_2$ is a naturally occurring truncation of GIP (1-42). Here we characterize eight N-terminal truncations of human GIP(1-30)NH$_2$: GIP(2- to 9-30)NH$_2$.

GIP(1-30)NH$_2$ is a naturally occurring truncation of GIP (1-42). Here we characterize eight N-terminal truncations of human GIP(1-30)NH$_2$: GIP(2- to 9-30)NH$_2$. Key results: GIP(1-30)NH$_2$ displaced $^{125}$I-GIP(1-42) equally to GIP(1-42) (Ki 0.75 nM), whereas the eight variants displayed lower affinities (Ki 2.3-347 nM) with highest affinities of GIP(3-30)NH$_2$ and (5-30)NH$_2$. Agonism was only observed for GIP(1-30)NH$_2$ with an $E_{max}$ on 100% of GIP(1-42) and GIP(2-30)NH$_2$ ($E_{max}$ 20%). GIP(2- to 9-30)NH$_2$ displayed antagonism (IC$_{50}$ 12-450 nM) and right-shifts of the GIP(1-42)-response curve. Schild plot analyses identified GIP(3-30)NH$_2$ and GIP(5-30)NH$_2$ as competitive antagonists (Ki 15 nM). Importantly, GIP(3-30) antagonized with a 26-fold higher potency than GIP(3-42). Binding studies with agonist ($^{125}$I-GIP(1-30)NH$_2$), partial agonist ($^{125}$I-GIP(2-30)NH$_2$) and competitive antagonist ($^{125}$I-GIP(3-30)NH$_2$) revealed distinct receptor conformations for these three ligand classes. The N-terminus is crucial for GIP functionality as agonist. Removal of the C-terminus of the naturally occurring DPP4-product GIP(3-42) creates another naturally occurring, but superior antagonist GIP(3-30)NH$_2$, that together with GIP(5-30)NH$_2$ were high-affinity competitive antagonists.

Methods

Wild type human GIP receptor cDNA was purchased from Origene™, Rockville, Md., USA (SC110906) and cloned into the pCMV Script-vector. Human native GIP(1-42) was purchased from Bachem™, Bubendorf, Switzerland (H5645). All truncated GIP peptides were synthesized by Caslo™, Lyngby, Denmark and based on the human GIP sequence. Porcine GIP(3-42) was custom synthesized by PolyPeptide Laboratories (WolfenBüttel, Germany). $^{125}$I-labelled native GIP (1-42) was purchased from PerkinElmer Life Sciences, Skovlunde, Denmark (NEX402025UC). Human GIP(1-30)NH$_2$, GIP(2-30)NH$_2$ and GIP(3-30)NH$_2$ were $^{125}$I-labeled using the standard stoichiometric chloramine T method as described previously (Holst and Bersani, 1991). The labeled peptides were purified by high-pressure liquid chromatography.

Cell Line and Transfection

COS-7 cells were grown in 10% CO$_2$ and at 37° C. in Dulbecco's modified Eagle's medium 1885 supplemented with 10% fetal bovine serum, 2 mM glutamine, 180 units/ml penicillin, and 45 g/ml streptomycin. Transfection of COS-7 cells was performed using the calcium phosphate precipitation method with chloroquine addition as previously described (Kissow et al., 2012).

cAMP-Assay

COS-7 cells (30.000 cells/well) were seeded in 96-well plates one day before transfection with human GIP receptor cDNA. Two days after transfection the cells were washed once with HEPES buffered saline (HBS) and incubated with HBS and 0.5 mM 3-isobutyl-1-methylxanthine (IBMX) for 30 minutes at 37° C. The various truncated GIP variants were added to the cells and incubated for 30 minutes at 37° C. in order to test for intrinsic activity. To test for antagonism of a given GIP variant, the cells were preincubated for 10 minutes at 37° C. with the GIP analogue followed by 20 minutes of incubation with GIP(1-42). The potency of the antagonists was determined from dose-response curves of the antagonist in the presence of a constant concentration of the GIP(1-42) corresponding to 50-80% of the maximal cAMP accumulation response ($E_{max}$) of GIP(1-42). For Schild analysis, various antagonist concentrations were added 10 minutes prior to GIP(1-42) dose-response curves. After ligand incubation, the HitHunter™ cAMP XS assay (an enzyme fragment complementation-based assay, DiscoveRx, Birmingham, United Kingdom) was carried out according to the manufacturer's instructions. All experiments were made in duplicates, and repeated at least three times. Luminescence was measured by Perkin Elmer™ EnVision 2104 Multilabled reader (Skovlunde, Danmark). In brief, the cells were lysed in the wells, the enzyme fragment-cAMP-antibody, an enzyme fragment and the enzyme substrates were added followed by 1 hour incubation at room temperature on shaker tray. The other enzyme fragment was added to the wells and incubated for 4 hours on shaker tray followed by measurements of luminescence. The ligand-induced cAMP competed with the binding of antibody to the first enzyme fragment and left the two fragments to fuse. The enzyme complex hydrolyzed the substrates and yielded luminescence. The number "n" refers to individual experiments with separate transfections although from same cell line.

Competitive Binding-Assay

COS-7 cells were seeded in 96-well plates 1 day after transfection with human GIP receptor cDNA. The number of cells seeded per well was selected to result in 5-10% specific binding of the added radioactive ligand (1000-5000 cells/well). Two days after transfection, cells were used for competition binding for 3 h at 4° C. to inhibit receptor internalization using 6-10 pM/well of $^{125}$I-GIP(1-42), $^{125}$I-GIP(1-30)NH$_2$, $^{125}$I-GIP(2-30)NH$_2$, or $^{125}$I-GIP(3-30)NH$_2$ as well as relevant amounts of unlabeled ligands in 50 mM Hepes buffer, pH 7.4, supplemented with 0.5% (w/v) bovine serum albumin. After incubation for 3 hours at 4° C., the cells were washed twice in ice-cold binding buffer and lysed using 200 mM NaOH with 1% SDS for 30 minutes. Non-specific binding was determined as the binding of radioligand to untransfected cells. All determinations were made in duplicates, and all experiments repeated at least three times. The samples were analyzed for radioactivity using a Wallac Wizard 1470 Gamma Counter (GMI Inc., Minnesota, USA). The number "n" refers to individual experiments with separate transfections although from same cell line.

Data Analysis

IC$_{50}$, EC$_{50}$, and K$_d$/K$_i$ values were determined by non-linear regression. These, as well as maximal binding capacity (B$_{max}$) values and Schild plot analysis were carried out with the GraphPad Prism 6.0 software (GraphPad, San Diego, Calif., USA) and Microsoft Excel™. Statistical analyses (unpaired t-tests) of two parameters were also performed with GraphPad Prism 6.0. The calculations of B$_{max}$ and K$_i$ values were based on the formula for one class of binding sites in homologous competition binding studies and the Cheng Prussoffs formula, respectively (DeBlasi et al., 1989). K$_d$ is the dissociation constant determined by homologous receptor binding. Dose ratios (DR) for the Schild analyses were based on the potency shift of the GIP(1-42) dose-response curve in absence or presence of a fixed antagonist concentration (DR=EC$_{50}$ in presence of antagonist/EC$_{50}$ in absence of antagonist). Schild plots were performed with log (DR-1) (ordinate) and log(antagonist concentration) (abscissa) to estimate the slopes and K$_i$ values (Lazareno and Birdsall, 1993).

Results

GIP(1-30)NH$_2$ is a Full GIP Receptor Agonist with High Affinity Equal to Native GIP(1-42)

Figure 6:
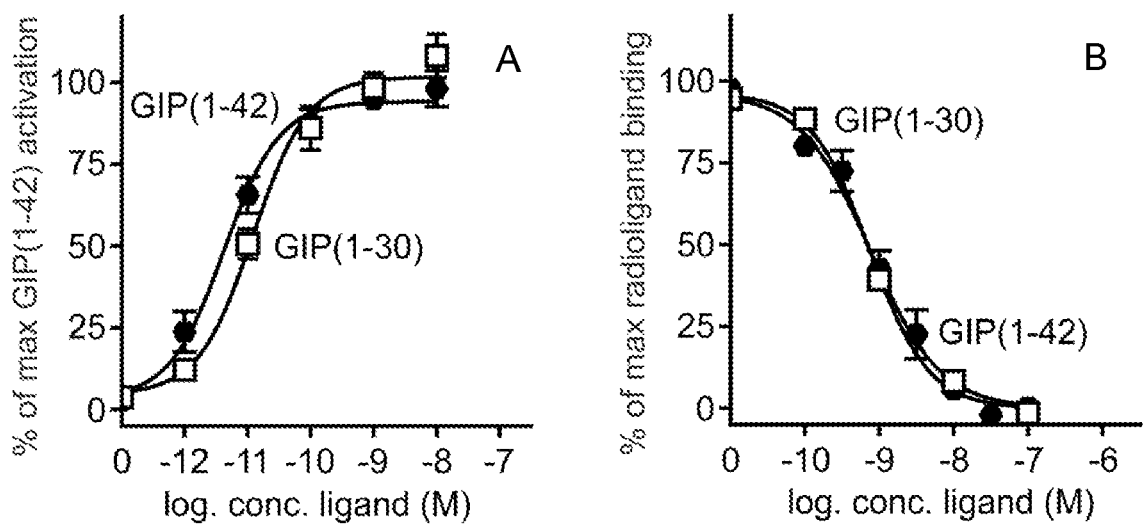
FIG. 6. GIP(1-30) is a high affinity full agonist of the GIP receptor. Human native GIP(1-42) sequence was acquired from NCBI Protein Database. The GIP receptor was transiently transfected in COS-7 cells and used for functional (A) and binding studies (B). A) cAMP accumulation assay with increased concentrations of native GIP(1-42) (SEQ ID NO: 65) (•) and GIP(1-30)NH$_2$ (SEQ ID NO:69) (□), mean±SEM, n=8. B) Competitive binding with the $^{125}$I-GIP (1-42) (SEQ ID NO: 65) radioligand displaced by GIP(1-42) (SEQ ID NO: 65) (•) and GIP(1-30) (SEQ ID NO:69) (□), mean±SEM, n=13.

To establish the role of the C-terminus for agonism in the human GIP system, we first measured cAMP responses to human GIP(1-42) and human GIP(1-30)NH$_2$ in transiently transfected COS-7 cells expressing the human GIP receptor (FIG. 6A). GIP(1-30)NH$_2$ was a full agonist on the GIP receptor with a high potency (EC$_{50}$) of 11.2 pM [log EC$_{50}$−10.95±0.11], compared to the 6.0 pM [log EC$_{50}$−11.21±0.16] of GIP(1-42) and with the same efficacy as GIP (1-42), consistent with earlier studies. Binding studies were performed with $^{125}$I-GIP(1-42) as the radioligand in the same cellular background. Truncation of the full length GIP(1-42) peptide at the 30-position did not change the affinity to the GIP receptor, and thus, resulted in affinities (IC$_{50}$) of 0.89 nM and 0.67 nM for GIP(1-30)NH$_2$ and GIP(1-42), respectively (FIG. 6B). Thus, GIP(1-30)NH$_2$ displayed the same potency, efficacy and affinity for the human GIP receptor as GIP(1-42).

The N-Terminus is Essential for High Affinity Binding

Figure 7:
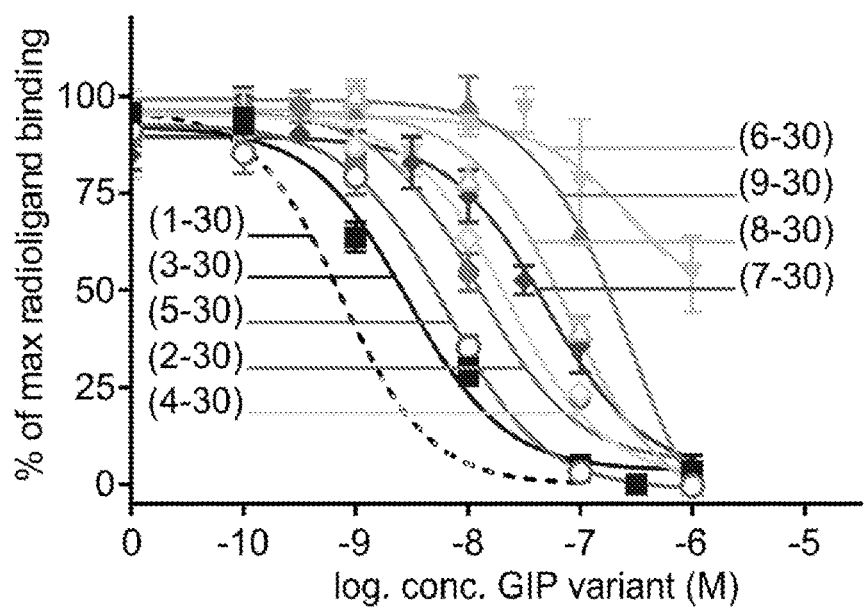
FIG. 7. GIP(3-30)NH$_2$ and GIP(5-30)NH$_2$ display highest affinity among the eight truncated GIP variants. The binding of $^{125}$I-GIP(1-42) (SEQ ID NO: 65) to transiently transfected COS-7 cells with the GIP receptor was tested in the presence of increasing amounts of GIP(1-30)NH$_2$ (SEQ ID NO:69) ( - - - ), GIP(3-30)NH$_2$ (SEQ ID NO: 1) (■), GIP(5-30)NH$_2$ (SEQ ID NO:78) (○), GIP(2-30)NH$_2$ (•), GIP(4-30)NH$_2$ (SEQ ID NO:77) (◇), GIP(7-30)NH$_2$ (♦), GIP(8-30)NH$_2$ (▲), GIP(9-30)NH$_2$ (α), or GIP(6-30)NH$_2$ (▼), mean±SEM, n=3-13.

To study the role of the N-terminus of human GIP(1-30) NH$_2$, the affinity of the eight N-terminally truncated peptides were compared to that of GIP(1-30)NH$_2$ in transiently transfected COS-7 cells using $^{125}$I-GIP(1-42) as radioligand (FIG. 7). Truncation resulted in decreased affinity with a tendency towards length-dependency, with a span from 2.3 fold to 347 fold decrease in affinity compared to GIP(1-30) NH$_2$. GIP(3-30)NH$_2$ followed by GIP(5-30)NH$_2$ displayed the highest affinities, while GIP(9-30)NH$_2$ and GIP(6-30) NH$_2$ had more than 300 fold lower affinities compared to GIP(1-30)NH$_2$. Taken together, this emphasizes the importance of the N-terminus for receptor binding.

GIP(2-30)NH$_2$ is a Partial Agonist and GIP(3- to 9-30)NH$_2$ are Antagonists of the GIP Receptor We measured cAMP accumulation in COS-7 cells, transiently transfected with the human GIP receptor, after incubation with each of the GIP variants (FIGS. 8A and 8B). Removal of the first amino acid from GIP(1-30)NH$_2$, created GIP(2-30)NH$_2$, which is a weak partial agonist with an efficacy of 20% compared to GIP(1-30)NH$_2$ and a potency of 3.7 nM [log EC$_{50}$−8.43±0.33, n=8] which is >3000 fold lower than GIP(1-30)NH$_2$. Removal of the second amino acid completely eliminated intrinsic activity (FIG. 8A); a pattern that was also seen for the remaining truncations (FIG. 8B). To determine whether the inactive forms had antagonistic properties, increasing concentrations of the GIP variants were added to a submaximal (50-80%) activation by GIP(1-42). All were able to inhibit the cAMP response induced by GIP(1-42) (FIGS. 8C and 8D). The most potent antagonists were GIP(3-30)NH$_2$ and GIP(5-30)NH$_2$ with IC$_{50}$ of 11.8 nM and 11.9 nM respectively (Table 1) in agreement with their high binding affinities. Similar to the binding studies, the shortest GIP variant, GIP(9-30)NH$_2$, had the lowest antagonistic potency with a 38-fold right-shift compared to GIP(3-30)NH$_2$.

TABLE 1

| | Competitive binding | | | | cAMP accumulation | | |
|---|---|---|---|---|---|---|---|
| | logIC$_{50}$ ± SEM | Ki (nM) | fold | n | logIC$_{50}$ ± SEM | IC$_{50}$ (nM) | n |
| GIP(1-30)NH$_2$ | −9.05 ± 0.02 | 0.89 | 1.0 | 13 | — | — | — |
| GIP(2-30)NH$_2$ | −7.85 ± 0.04 | 14.3 | 16 | 10 | −7.66 ± 0.1 | 21.7 | 4 |
| GIP(3-30)NH$_2$ | −8.63 ± 0.04 | 2.3 | 2.6 | 12 | −7.93 ± 0.04 | 11.8 | 6 |
| GIP(4-30)NH$_2$ | −7.67 ± 0.02 | 21.5 | 24 | 3 | −6.97 ± 0.4 | 108 | 4 |
| GIP(5-30)NH$_2$ | −8.23 ± 0.05 | 5.9 | 6.6 | 3 | −7.92 ± 0.4 | 11.9 | 4 |
| GIP(6-30)NH$_2$ | −6.46 ± 0.09 | 347 | 391 | 10 | −6.47 ± 0.6 | 342 | 4 |
| GIP(7-30)NH$_2$ | −7.58 ± 0.08 | 26 | 30 | 9 | −6.86 ± 0.4 | 137 | 7 |
| GIP(8-30)NH$_2$ | −7.10 ± 0.04 | 79 | 89 | 3 | −6.88 ± 0.5 | 133 | 5 |
| GIP(9-30)NH$_2$ | −6.51 ± 0.08 | 307 | 345 | 3 | −6.35 ± 0.6 | 450 | 4 |

Table 1.

The table displays the IC$_{50}$-values from the binding studies (FIG. 7) with the fold change of GIP(1-30)NH$_2$ affinity, and the cAMP accumulation studies (FIG. 8) with antagonist properties.

GIP(3-30)NH$_2$ and GIP(5-30)NH$_2$ are Competitive Antagonists

Figure 9:
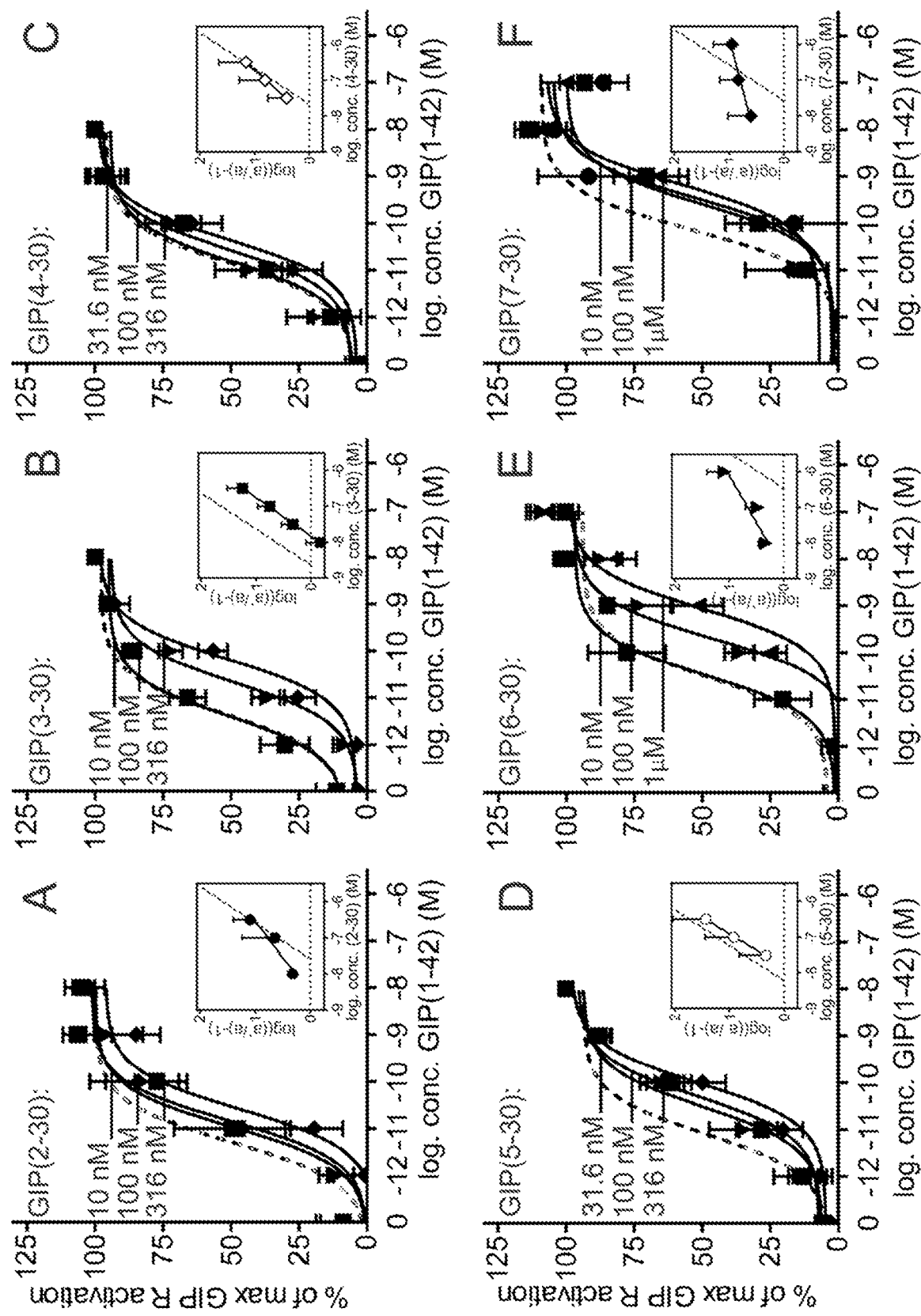
FIG. 9. Of the six antagonists only GIP(3-30)NH$_2$ and GIP(5-30)NH$_2$ are competitive antagonists. GIP(1-42) mediated cAMP accumulation assayed for transiently transfected COS-7 cells with the GIP receptor in the absence of and with increasing concentrations of either GIP(2-30)NH$_2$, GIP(3-30)NH$_2$ (SEQ ID NO: 1), GIP(4-30)NH$_2$ (SEQ ID NO:77), GIP(5-30)NH$_2$(SEQ ID NO:78), GIP(6-30)NH$_2$, or GIP(7-30)NH$_2$. The corresponding Schild plot is presented with a comparison to a linear regression with a slope of 1.0 and the X-intercept of K$_i$ for the antagonist. GIP(2-30)NH$_2$ (A), GIP(3-30)NH$_2$ (B), GIP(4-30)NH$_2$ (C), GIP(5-30)NH$_2$ (D), GIP(6-30)NH$_2$ (E), and GIP(7-30)NH$_2$ (F), mean±SEM, n=3-6. Antagonist concentrations: 10 nM (■), 31.6 nM (•), 100 nM (▼), 316 nM (♦), 1 µM (▲).

A Schild analysis was performed for the four most potent antagonists, in addition to the previously described antagonists GIP(6-30)NH$_2$ and GIP(7-30)NH$_2$. This analysis determines whether an antagonist acts competitively and is illustrated by the Schild Plot. A straight line with a Hill slope of 1.0 indicates competitive antagonism. The antagonists were added in various constant concentrations to the dose-response curves of GIP(1-42) (FIG. 9). All six antagonists were able to right-shift the GIP(1-42) dose-response curve with no changes in efficacy. However, only GIP(3-30)NH$_2$ and GIP(5-30)NH$_2$ act as pure competitive antagonists judged by a straight line with a slope of 1 (inserts in FIGS. 9B and 9D). These two ligands displayed slopes of 0.93±0.02 and 1.1±0.04, respectively, while the slopes for GIP(2-30)NH$_2$, GIP(4-30)NH$_2$, GIP(6-30)NH$_2$, and GIP(7-30)NH$_2$ were 0.49±0.14, 0.75±0.02, 0.38±0.13, and 0.17±0.03, respectively (FIG. 9B-F). The lack of ability to compete equally with the agonist could indicate an allosteric component in the antagonistic properties of these ligands. The X-intercept or pA$_2$-value of the Schild plot corresponds to the affinity constant of the antagonist if the Hill slope equals 1. For the two competitive antagonists GIP(3-30)NH$_2$ and GIP(5-30)NH$_2$, the pA$_2$-values were 14.9 nM and 15.2 nM, respectively, thus in the same range as the K$_i$ determined from the binding studies (2.3 nM and 5.9 nM respectively). In summary, this analysis identified GIP(3-30)NH$_2$ and GIP(5-30)NH$_2$ as high affinity competitive GIP receptor antagonists.

The Functionalities of the Ligands Reflect the Binding Properties

Figure 8:
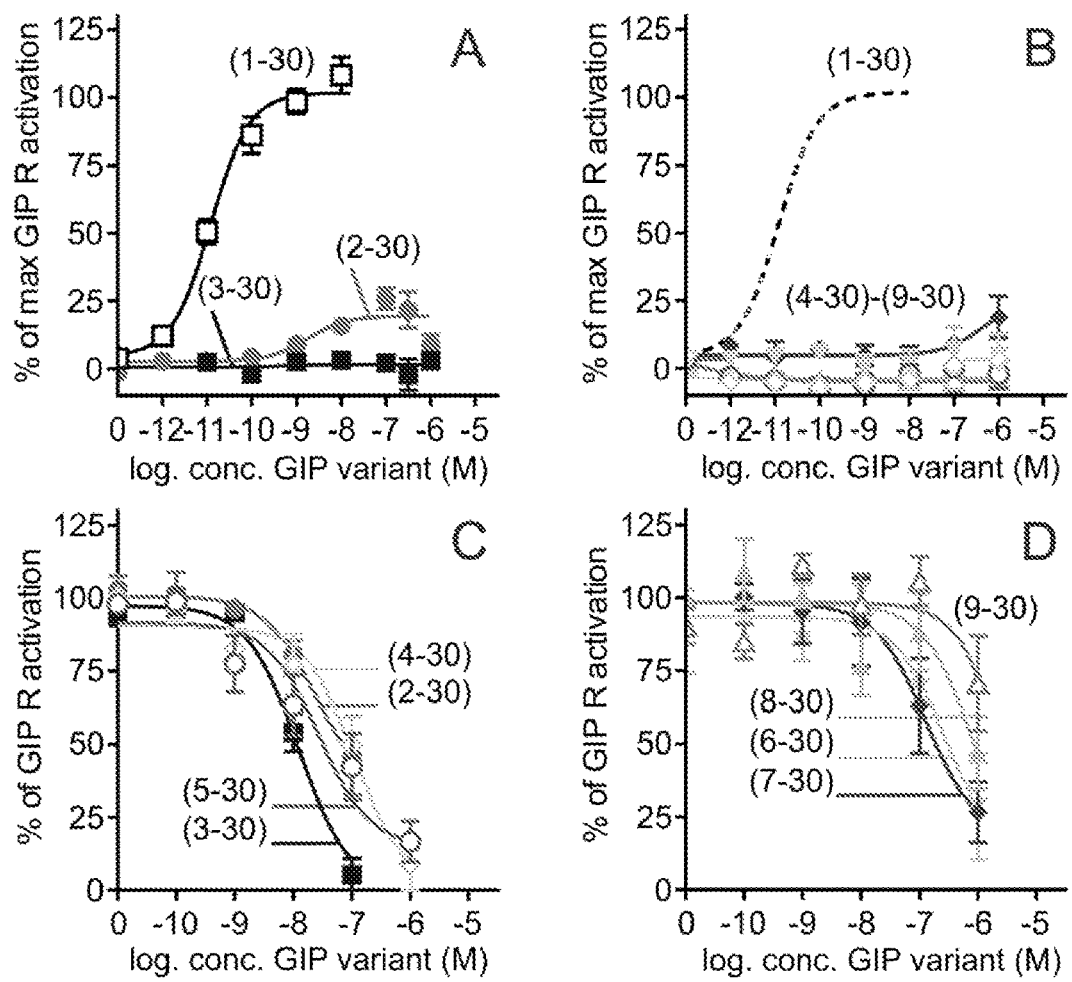
FIG. 8. GIP(3-30) and GIP(5-30) are the most potent GIP receptor antagonists. cAMP accumulation in transiently transfected COS-7 cells with GIP receptor was assessed following incubation with GIP(1-30)NH$_2$ (SEQ ID NO:69) ( - - - ), GIP(2-30)NH$_2$ (•), GIP(3-30)NH$_2$ (SEQ ID NO: 1) (■), GIP(4-30)NH$_2$(SEQ ID NO:77) (◇), GIP(5-30)NH$_2$ (SEQ ID NO:78) (○), GIP(6-30)NH$_2$ (▼), GIP(7-30)NH$_2$ (♦), GIP(8-30)NH$_2$ (▲), or GIP(9-30)NH$_2$ (Δ). A/B) Ligand dose-response stimulated cAMP accumulation, mean±SEM, n=3-6. C/D) Dose response curves of antagonists inhibited a constant amount of native GIP(1-42) corresponding to 50-80% of max receptor activation, mean±SEM, n=4-7.
Figure 10:
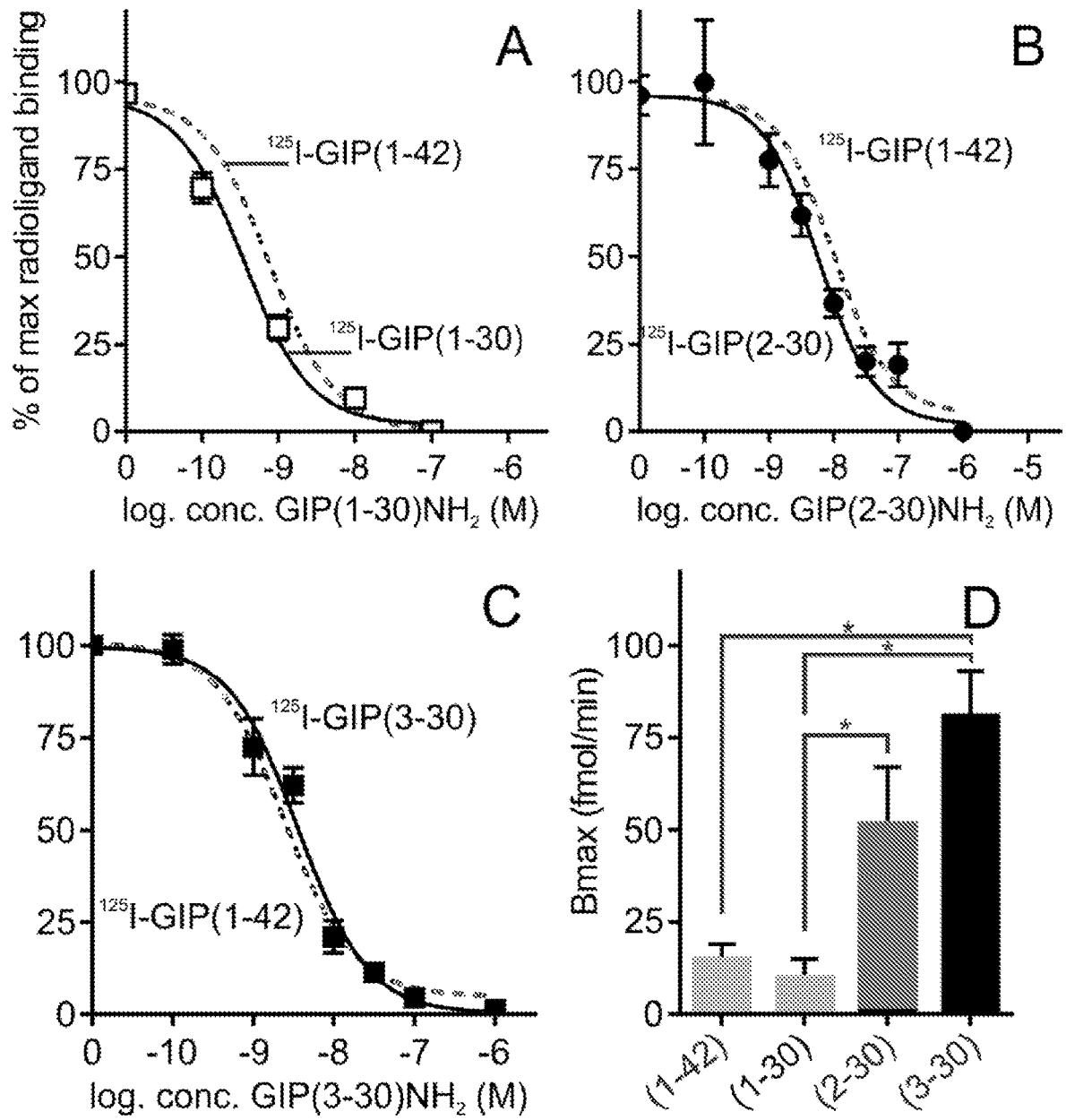
FIG. 10. The homologous binding curves are equivalent to the heterologous binding studies with native $^{125}$I-GIP(1-42) radioligand. A-C) Transiently transfected COS-7 cells with the GIP receptor were used in homolog competitive binding studies with $^{125}$I-GIP(1-30)NH$_2$ (SEQ ID NO:69) (□), $^{125}$I-GIP(2-30)NH$_2$ (•), and $^{125}$I-GIP(3-30)NH$_2$ (SEQ ID NO:1) (■) and heterologous binding studies with $^{125}$I-GIP(1-42) (SEQ ID NO: 65) ( - - - ), mean±SEM, n=3-5. D) B$_{max}$-values calculated from the homologous binding curves for GIP(1-42) (SEQ ID NO: 65), GIP(1-30)NH$_2$ (SEQ ID NO:69), GIP(2-30)NH$_2$, and GIP(3-30)NH$_2$ (SEQ ID NO: 1), mean±SEM, n=5.

The N-terminal truncations of GIP(1-30)NH$_2$ had a span in affinities (Ki) from 1 nM to 350 nM (FIG. 7 and Table 1) and concomitantly, displayed different pharmacodynamics with both competitive and non-competitive antagonistic properties (FIGS. 8 and 9). To further analyse the receptor interaction of these variants we performed homologous competitive binding studies with $^{125}$I-GIP(1-30)NH$_2$, $^{125}$I-GIP(2-30)NH$_2$, and $^{125}$I-GIP(3-30)NH$_2$ as radioligands (representing a full agonist, a partial agonist, and a competitive antagonist, respectively). The K$_d$ values for GIP(1-30)NH$_2$, GIP(2-30)NH$_2$ and GIP(3-30)NH$_2$ obtained from the homologous binding experiments (FIG. 10 and Table 2) were in the same range as the K$_i$ values obtained in the heterologous binding experiments using $^{125}$I-GIP(1-42) as radioligand (Table 1). However, minor, yet significant, changes were observed upon a closer look at the affinities, as higher affinities were observed when GIP(1-30)NH$_2$ and GIP(2-30)NH$_2$ competed with their own iodinated versions (homologous binding), compared to when they competed with $^{125}$I-GIP(1-42) (heterologous binding) (p=0.012 and p=0.0031, respectively, FIGS. 10A and B). Thus, the lack of C-terminus decreased the ability of GIP(1-30)NH$_2$ and GIP(2-30)NH$_2$ to compete with the full length agonist GIP(1-42) for the GIP receptor. In contrast, the N-terminally truncated antagonist GIP(3-30)NH$_2$, was able to displace the homologous radioligand with the same affinity as the full agonist $^{125}$I-GIP(1-42) radioligands (p=0.45, FIG. 10C). The B$_{max}$ was calculated from the homologous binding studies (DeBlasi et al., 1989) and uncovered significantly more binding sites for the antagonists compared to the two agonists (FIG. 10D), which illustrates the general property of antagonists to stabilize several inactive receptor confirmations, while agonists preferentially bind to the active confirmation(s) (Rosenkilde et al., 1994).

TABLE 2 A

| | $^{125}$I-GIP(1-30)NH$_2$ | | | | |
|---|---|---|---|---|---|
| | log (IC$_{50}$) | ±SEM | IC$_{50}$ (nM) | fold change GIP(1-30)NH$_2$ | n |
| GIP(1-42)NH$_2$ | −9.24 | 0.19 | 0.58 | 1.9 | 3 |
| GIP(1-30)NH$_2$ | −9.52 | 0.16 | 0.30 | 1.0 | 5 |
| GIP(2-30)NH$_2$ | −7.59 | 0.18 | 26 | 84.3 | 4 |
| GIP(3-30)NH$_2$ | −8.35 | 0.071 | 4.4 | 14.5 | 4 |
| GIP(6-30)NH$_2$ | −5.97 | 0.066 | 1.065 | 3502 | 5 |
| GIP(7-30)NH$_2$ | −7.43 | 0.25 | 37 | 120.9 | 5 |

TABLE 2 B

| | $^{125}$I-GIP(2-30)NH$_2$ | | | | |
|---|---|---|---|---|---|
| | log (IC$_{50}$) | ±SEM | IC$_{50}$ (nM) | fold change GIP(1-30)NH$_2$ | n |
| GIP(1-42)NH$_2$ | −9.36 | 0.087 | 0.43 | 0.9 | 3 |
| GIP(1-30)NH$_2$ | −9.32 | 0.482 | 0.48 | 1.0 | 3 |
| GIP(2-30)NH$_2$ | −8.57 | 0.28 | 2.7 | 10.5 | 5 |
| GIP(3-30)NH$_2$ | −9.12 | 0.20 | 0.76 | 1.6 | 3 |
| GIP(6-30)NH$_2$ | −6.47 | 0.28 | 340 | 707 | 4 |
| GIP(7-30)NH$_2$ | −7.54 | 0.23 | 29 | 60.6 | 5 |

TABLE 2 C

| | $^{125}$I-GIP(3-30)NH$_2$ | | | | |
|---|---|---|---|---|---|
| | log (IC$_{50}$) | ±SEM | IC$_{50}$ (nM) | fold change GIP(1-30)NH$_2$ | n |
| GIP(1-42)NH$_2$ | −8.97 | 0.0015 | 1.07 | 0.6 | 3 |
| GIP(1-30)NH$_2$ | −8.78 | 0.063 | 1.7 | 1.0 | 3 |
| GIP(2-30)NH$_2$ | −8.11 | 0.065 | 7.7 | 4.6 | 4 |
| GIP(3-30)NH$_2$ | −8.47 | 0.12 | 3.4 | 2.0 | 5 |
| GIP(6-30)NH$_2$ | −6.43 | 0.26 | 370 | 223 | 4 |
| GIP(7-30)NH$_2$ | −7.68 | 0.16 | 21 | 12.7 | 5 |

The binding properties were further elucidated through heterologous binding studies with $^{125}$I-GIP(1-30)NH$_2$, $^{125}$I-GIP(2-30)NH$_2$ $^{125}$I-GIP(3-30)NH$_2$ displaced by GIP(1-42), GIP(1-30)NH$_2$, GIP(2-30)NH$_2$, and GIP(3-30)NH$_2$, and the previously described GIP(6-30)NH$_2$, and GIP(7-30)NH$_2$ (Table 2). Again, the agonists GIP(1-30)NH$_2$ and GIP(1-42) displaced the agonist radioligand ($^{125}$I-GIP(1-30)NH$_2$) most efficiently, while their affinities decreased in competition with the radiolabeled antagonists. The opposite was observed for the antagonists that displaced the partial agonist ($^{125}$I-GIP(2-30)NH$_2$) and the antagonist ($^{125}$I-GIP(3-30)NH$_2$) radioligand with highest affinities. Thereby, when looking at apparent affinities, the largest effects of increased truncation of GIP(1-30)NH$_2$ were observed with the agonist as radioligand with >3000-fold decrease in affinity of GIP (7-30)NH$_2$ compared to GIP(1-30)NH$_2$ measured with agonist radioligand, and only 223-fold decrease when measured with $^{125}$I-GIP(3-30)NH$_2$ as radioligand. This pattern was observed for all four antagonists (Table 2).

The C-Terminal Part of GIP Acts as a Negative Regulator of the Antagonistic Action of GIP(3-42)

Figure 11:
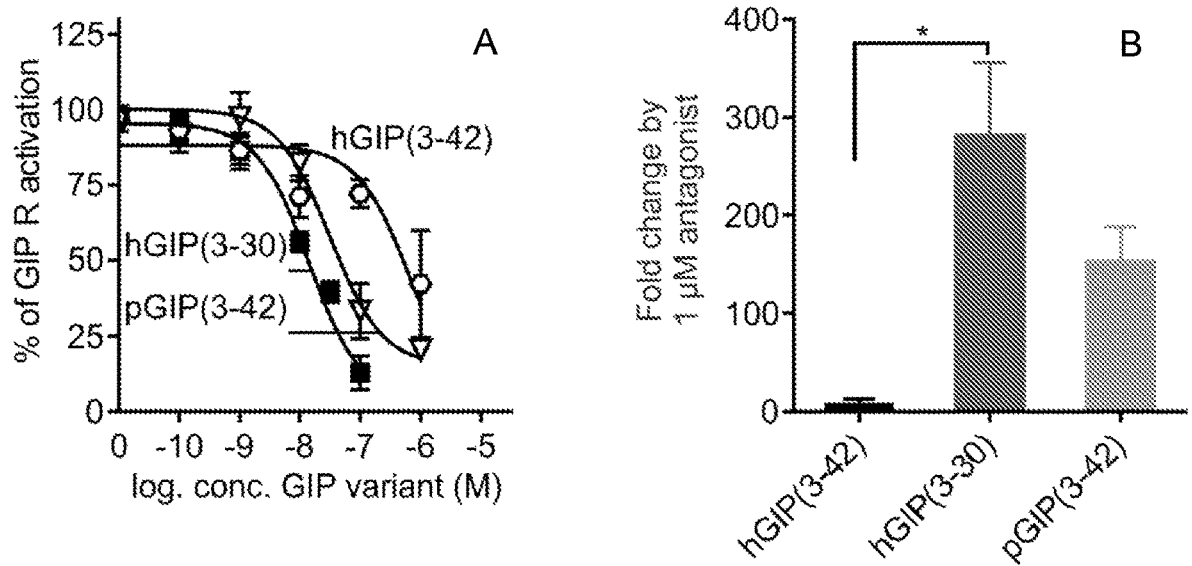
FIG. 11. Human GIP(3-42) is a low potent antagonist on the human GIP receptor compared to human GIP(3-30) and porcine GIP(3-42). Human and porcine GIP(1-42) sequence was acquired from NCBI Protein Database (UniProtKB-P01281 (GIP_PIG). The human GIP receptor transiently transfected in COS-7 cells was used in cAMP accumulation assay. A) Dose-response curves of antagonists inhibited a constant amount of native GIP(1-42) corresponding to 50-80% of max receptor activation, hGIP(3-42) (SEQ ID NO: 62) (○), hGIP(3-30)NH$_2$ (SEQ ID NO: 1) (■), and pGIP(3-42) (∇), mean±SEM, n=3-17. B) Fold change in potency of human GIP(1-42) by 1 µM antagonist. The bars display mean fold change±SEM, n=3-4.
Figure 12:
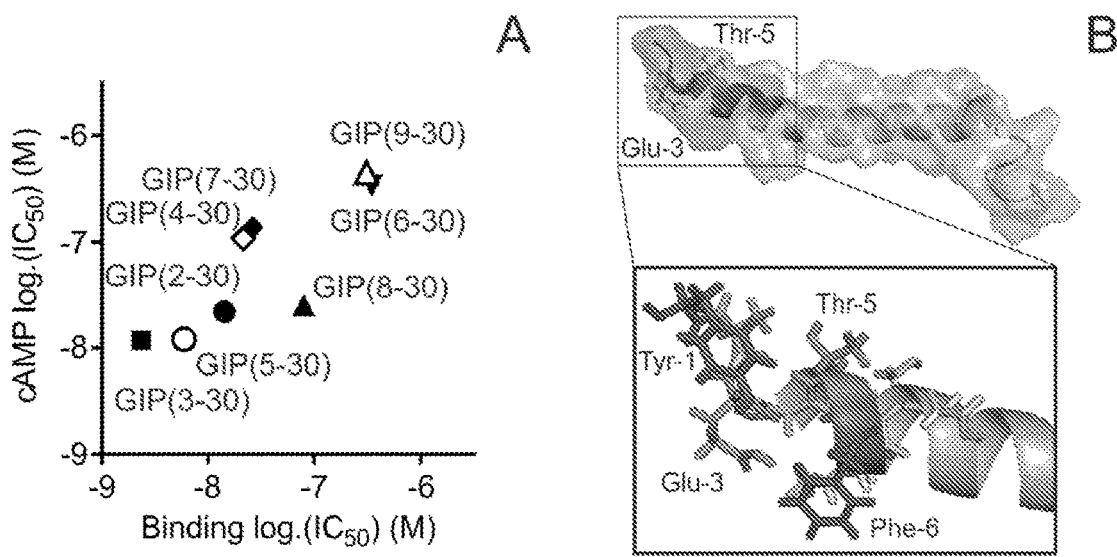
FIG. 12. Correlation of affinity and antagonistic potency (A) and structure of the N-terminus of GIP (B). A) The correlation of calculated affinities (binding log.IC$_{50}$) and antagonistic potencies (cAMP log.IC$_{50}$) plotted for the eight GIP receptor antagonists. GIP(2-30)NH$_2$ (•), GIP(3-30)NH$_2$ (SEQ ID NO: 1) (■), GIP(4-30)NH$_2$ (SEQ ID NO: 177 (◇), GIP(5-30)NH$_2$ (SEQ ID NO: 78) (○), GIP(6-30)NH$_2$ (▼), GIP(7-30)NH$_2$ (♦), GIP(8-30)NH$_2$ (▲), and GIP(9-30)NH$_2$ (Δ). B) The published structure (Parthier et al., 2007) of the native GIP(1-42) peptide with amino acids 1-9 in blue, Glu-3 and Thr-5 in green and Tyr-1 and Phe-6 in pink.

The identification of GIP(3-30)NH$_2$ as the most potent antagonist prompted us to compare it with GIP(3-42) in order to directly determine the impact of the C-terminal amino acids 31 through 42. We also included the porcine GIP(3-42), representing a low-potent antagonist on the human GIP receptor in vitro, with no ability to antagonize porcine GIP(1-42)-mediated insulin secretion in pigs at physiological concentrations (Deacon et al., 2006). Porcine GIP(3-42) has an arginine in position 18 and serine in position 34, whereas the human sequence has histidine and asparagine, respectively. Like GIP(3-30)NH$_2$ (FIG. 8A), neither of the GIP(3-42) variants had any intrinsic agonistic activity in cAMP-accumulation assay (data not shown, n=3), but both were able to antagonize submaximal (50-80%) human GIP(1-42)-induced activation (FIG. 11B). Importantly, human GIP(3-42) was remarkably less potent than human GIP(3-30)NH$_2$ (26-fold lower potency, FIG. 11B) and 1 μM of this resulted in only 7.3-fold shift in the dose-response curve of human GIP(1-42) compared to 281 fold for human GIP(3-30)NH$_2$ (FIG. 11C). The porcine variant displayed higher potency compared to human GIP (3-42), yet not as high as human GIP(3-30)NH$_2$. Thus, the C-terminus has a functional role as its absences improve the antagonistic properties in GIP(3-30)NH$_2$ compared to GIP (3-42).

Figure 13:
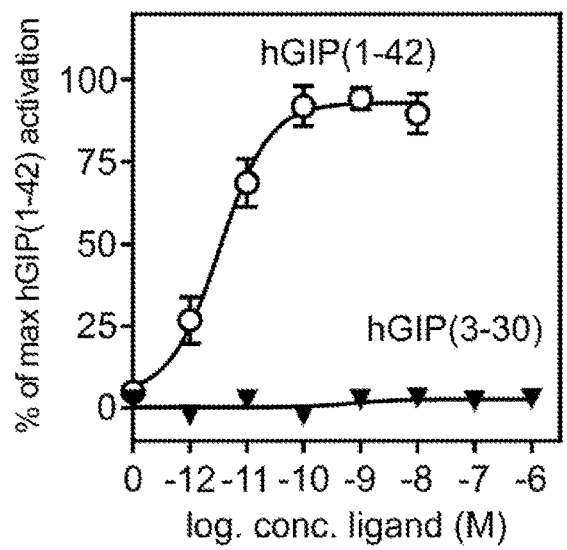
FIG. 13: cAMP accumulation assay showing no GIP(3-30) induced activation. 35.000 COS-7 cells/well were transiently transfected with hGIPR and stimulated with either GIP(1-42) (SEQ ID NO: 65) or hGIP(3-30) (SEQ ID NO: 3); n=4.
Figure 14:
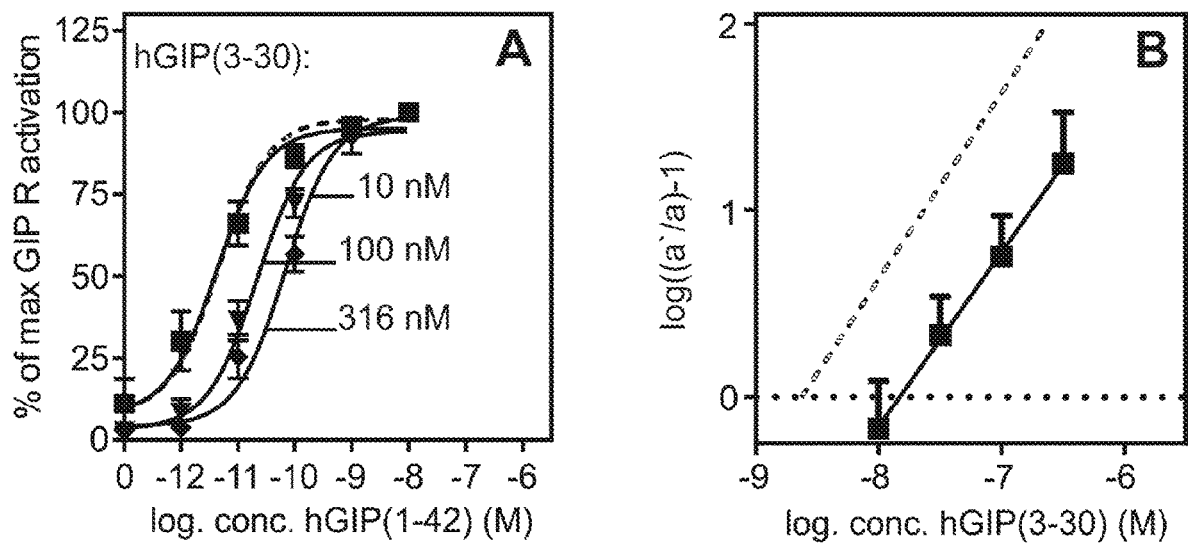
FIG. 14: Schild plot analysis, using the cAMP accumulation assay, defines GIP(3-30) (SEQ ID NO: 1) as a competitive antagonist. 35.000 COS-7 cells/well were transiently transfected with hGIPR. A) cAMP production was measured as a function of GIP concentration in the absence or presence of increasing GIP(3-30) concentrations. These schild curves clearly indicate a competitive nature of GIP (3-30) as seen in the shift in potency. B) The Schild plot analysis for the dose-response curves clearly shows the competitive nature of hGIP(3-30) (SEQ ID NO: 1), seen as in the linearity of the plot with a Hill slope of 1.1 and the Ki (X-intercept) of 15 nM.
Figure 15:
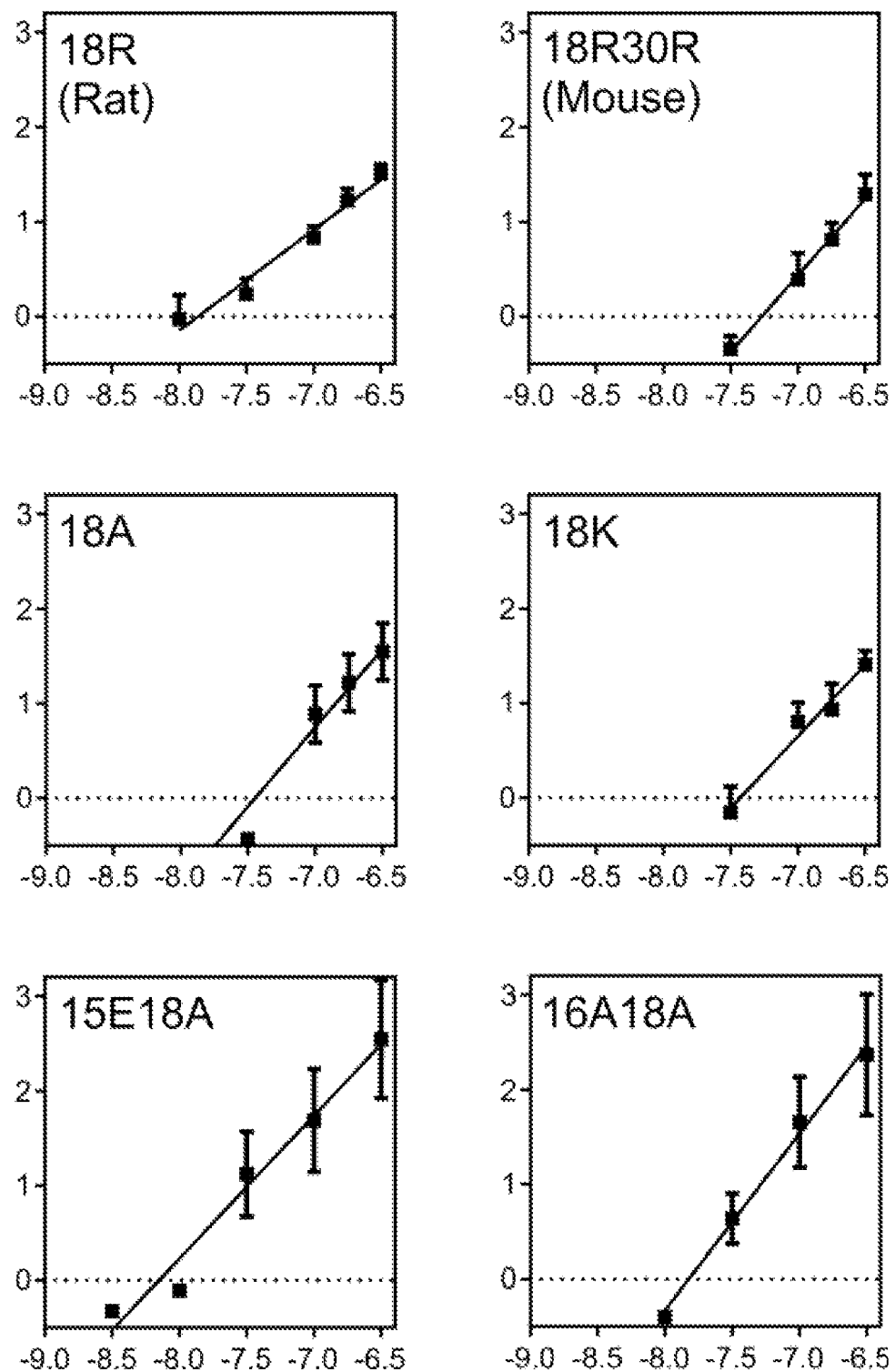
FIG. 15: Schild plot analysis, using the cAMP accumulation assay, analyses the mutated GIP(3-30) variants as competitive antagonists. Only rat GIP(3-30) (SEQ ID NO: 2) shows competitive antagonism. 35.000 COS-7 cells/well were transiently transfected with hGIPR. These schild curves clearly indicate antagonistic properties of the GIP(3-30) variants as seen in the shift in potency.

Example 8—Characterization of GIP Mutations/Variants cAMP accumulation assays and schild plots were performed essentially as outlined in the above examples. Selected mutations in the GIP3-30 peptide were tested. Mutations of the amino acids in position 15 and 18 (GIP(3-30)15E18A) decreased the Ki-value and therefore increased the antagonistic capabilities. See FIGS. 13-15.

| Name | Mutations | Ki (nM) | Hill-slope of plot | Experiments (number) |
|---|---|---|---|---|
| hGIP(3-30) (SEQ ID NO: 1) | — | 15 | 1.1 | 4 |
| 18R (Rat) (SEQ ID NO: 2) | Position 18 to Arginine | 14 | 0.6 | 4 |
| 18R30R (Mouse) (SEQ ID NO: 3) | Pos. 18 and 30 → Arginine | 54 | 0.7 | 4 |
| 18A (SEQ ID NO: 79) | Position 18 to Alanine | 35 | 0.9 | 3 |
| 18K (SEQ ID NO: 80) | Position 18 to Lysine | 37 | 0.6 | 4 |
| 15E18A (SEQ ID NO: 81) | Pos. 15 → Glutamic acid and pos. 18 → Alanine | 7.9 | 0.7 | 3 |
| 16A18A (SEQ ID NO: 82) | Pos. 16 and 18 → Alanine | 15 | 0.5 | 3 |

Example 9

Studies in rodents are conducted to verify the effect of hGIP(3-30) (SEQ ID NO:1) in vivo. The GIP receptor antagonist is administered in rats (n=8-10) before an oral glucose tolerance test (OGTT). The rats are given a glucose load after subcutaneous administration of the antagonist and the glucose tolerance will be measured by plasma concentrations of glucose and insulin the following hour. The same procedure is previously performed with other GIP antagonists (Pathak et al., 2015).

REFERENCES

1. Baggio L L, Drucker D J. Biology of Incretins: GLP-1 and GIP. Gastroenterology 2007; 132(6):2131-2157.
2. Holst J J. On the Physiology of GIP and GLP-1. Horm Metab Res 2004; 36(11/12):747-754.
3. Heer J, Rasmussen C, Coy D H, Holst J J. Glucagon-like peptide-1, but not glucose-dependent insulinotropic peptide, inhibits glucagon secretion via somatostatin (receptor subtype 2) in the perfused rat pancreas. Diabetologia 2008; 51(12):2263-2270.
4. Gutniak M, +ÿrkov C, Holst J J, Ahr+® n B, Efendi-çS. Antidiabetogenic Effect of Glucagon-like Peptide-1 (7GÇô36)amide in Normal Subjects and Patients with Diabetes Mellitus. N Engl J Med 1992; 326(20):1316-1322.
5. Christensen M, Vedtofte L, Holst J J, Vilsboell T, Knop F K. Glucose-Dependent Insulinotropic Polypeptide: A Bifunctional Glucose-Dependent Regulator of Glucagon and Insulin Secretion in Humans. Diabetes 2011; 60(12):3103-3109.
6. Pederson R, Brown J. Interaction of Gastric Inhibitory Polypeptide, Glucose, and Arginine on Insulin and Glucagon Secretion from the Perfused Rat Pancreas. Endocrinology 1978; 103(2):610-615.
7. Adrian T E, Bloom S R, Hermansen K, Iversen J. Pancreatic polypeptide, glucagon and insulin secretion from the isolated perfused canine pancreas. Diabetologia 1978; 14(6):413-417.
8. Brunicardi F C, Druck P, Seymour N E, Sun Y S, Elahi D, Andersen D K. Selective neurohormonal interactions in islet cell secretion in the isolated perfused human pancreas. Journal of Surgical Research 1990; 48(4):273-278.
9. Dupre J, Caussignac Y, McDonald T J, Van Vliet S. Stimulation of Glucagon Secretion by Gastric Inhibitory Polypeptide in Patients with Hepatic Cirrhosis and Hyperglucagonemia. The Journal of Clinical Endocrinology & Metabolism 1991; 72(1):125-129.
10. Ding W G, Renstrom E, Rorsman P, Buschard K, Gromada J. Glucagon-like peptide I and glucose-dependent insulinotropic polypeptide stimulate Ca2+-induced secretion in rat alpha-cells by a protein kinase A-mediated mechanism. Diabetes 1997; 46(5):792-800.
11. Meier J J, Gallwitz B, Siepmann N et al. Gastric inhibitory polypeptide (GIP) dose-dependently stimulates glucagon secretion in healthy human subjects at euglycaemia. Diabetologia 2003; 46(6):798-801.
12. Christensen M B, Calanna S, Holst J J, Vilsboell T, Knop F K. Glucose-dependent Insulinotropic Polypeptide: Blood Glucose Stabilizing Effects in Patients With Type 2 Diabetes. The Journal of Clinical Endocrinology & Metabolism 2013; 99(3):E418-E426.
13. Christensen M, Calanna S, Sparre-Ulrich A H et al. Glucose-Dependent Insulinotropic Polypeptide Augments Glucagon Responses to Hypoglycemia in Type 1 Diabetes. Diabetes 2014.
14. Song D H, GettyGÇôKaushik L, Tseng E, Simon J, Corkey B E, Wolfe M M. Glucose-Dependent Insulinotropic Polypeptide Enhances Adipocyte Development and Glucose Uptake in Part Through Akt Activation. Gastroenterology 2007; 133(6):1796-1805.
15. Miyawaki K, Yamada Y, Ban N et al. Inhibition of gastric inhibitory polypeptide signaling prevents obesity. Nat Med 2002; 8(7):738-742.
16. Starich G H, Bar R S, Mazzaferri E L. GIP increases insulin receptor affinity and cellular sensitivity in adipocytes. Am J Physiol 1985; 249(6 Pt 1):E603-E607.
17. Getty-Kaushik L, Song D H, Boylan M O, Corkey B E, Wolfe M M. Glucose-Dependent Insulinotropic Polypeptide Modulates Adipocyte Lipolysis and Reesterification. Obesity 2006; 14(7):1124-1131.

18. Hauner H, Glatting G, Kaminska D, Pfeiffer E F. Effects of gastric inhibitory polypeptide on glucose and lipid metabolism of isolated rat adipocytes. Ann Nutr Metab 1988; 32(5-6):282-288.
19. Kim S J, Nian C, Karunakaran S, Clee S M, Isales C M, McIntosh C H S. GIP-Overexpressing Mice Demonstrate Reduced Diet-Induced Obesity and Steatosis, and Improved Glucose Homeostasis. PLoS ONE 2012; 7(7): e40156.
20. Nasteska D, Harada N, Suzuki K et al. Chronic Reduction of GIP Secretion Alleviates Obesity and Insulin Resistance Under High-Fat Diet Conditions. Diabetes 2014; 63(7):2332-2343.
21. Miyawaki K, Yamada Y, Yano H et al. Glucose intolerance caused by a defect in the entero-insular axis: A study in gastric inhibitory polypeptide receptor knockout mice. Proceedings of the National Academy of Sciences 1999; 96(26):14843-14847.
22. Ahlqvist E, Osmark P, Kuulasmaa T et al. Link Between GIP and Osteopontin in Adipose Tissue and Insulin Resistance. Diabetes 2013; 62(6):2088-2094.
23. Calanna S, Christensen M, Holst J J et al. Secretion of Glucose-Dependent Insulinotropic Polypeptide in Patients With Type 2 Diabetes: Systematic review and meta-analysis of clinical studies. Diabetes Care 2013; 36(10):3346-3352.
24. Asmar M, Simonsen L, Madsbad S, Stallknecht B, Holst J J, B++low J. Glucose-Dependent Insulinotropic Polypeptide May Enhance Fatty Acid Re-esterification in Subcutaneous Abdominal Adipose Tissue in Lean Humans. Diabetes 2010; 59(9):2160-2163.
25. Deschamps I, Heptner W, Desjeux J F, Baltakse V, Machinot S, Lestradet H. Effects of diet on insulin and gastric inhibitory polypeptide levels in obese children. Pediatr Res 1980; 14(4 Pt 1):300-303.
26. Brøns C, Jensen C B, Storgaard H et al. Impact of short-term high-fat feeding on glucose and insulin metabolism in young healthy men. The Journal of Physiology 2009; 587(10):2387-2397.
27. Raufman J P, Singh L, Eng J. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry 1991; 266(5):2897-2902.
28. Jørgensen N B, Dirksen C, Bojsen-Møller K N et al. Exaggerated Glucagon-Like Peptide 1 Response Is Important for Improved+|−Cell Function and Glucose Tolerance After Roux-en-Y Gastric Bypass in Patients With Type 2 Diabetes. Diabetes 2013; 62(9):3044-3052.
29. Nakamura T, Tanimoto H, Mizuno Y, Tsubamoto Y, Noda H. Biological and functional characteristics of a novel lowGÇômolecular weight antagonist of glucose-dependent insulinotropic polypeptide receptor, SKL-14959, in vitro and in vivo. Diabetes, Obesity and Metabolism 2012; 14(6):511-517.
30. Ebert R, Illmer K, Creutzfeldt W. Release of gastric inhibitory polypeptide (GIP) by intraduodenal acidification in rats and humans and abolishment of the incretin effect of acid by GIP-antiserum in rats. Gastroenterology 1979; 76(3):515-523.
31. Fulurija A, Lutz T A, Sladko K et al. Vaccination against GIP for the Treatment of Obesity. PLoS ONE 2008; 3(9):e3163.
32. Irwin N, McClean P L, Patterson S, Hunter K, Flatt P R. Active immunisation against gastric inhibitory polypeptide (GIP) improves blood glucose control in an animal model of obesity-diabetes. Biological Chemistry. bchm 390, 75. 2009. 16-7-2014.
33. Hinke S A, Manhart S, Pamir N et al. Identification of a bioactive domain in the amino-terminus of glucose-dependent insulinotropic polypeptide (GIP). Biochimica et Biophysica Acta (BBA)-Protein Structure and Molecular Enzymology 2001; 1547(1):143-155.
34. Tseng C C, Kieffer T J, Jarboe L A, Usdin T B, Wolfe M M. Postprandial stimulation of insulin release by glucose-dependent insulinotropic polypeptide (GIP). Effect of a specific glucose-dependent insulinotropic polypeptide receptor antagonist in the rat. J Clin Invest 1996; 98(11): 2440-2445.
35. Irwin N, Green B D, Parker J C, Gault V A, O'Harte F P M, Flatt P R. Biological activity and antidiabetic potential of synthetic fragment peptides of glucose-dependent insulinotropic polypeptide, GIP(1-16) and (Pro3)GIP(1-16). Regulatory Peptides 2006; 135(1GÇô2):45-53.
36. Kerr B D, Flatt A J S, Flatt P R, Gault V A. Characterization and biological actions of N-terminal truncated forms of glucose-dependent insulinotropic polypeptide. Biochemical and Biophysical Research Communications 2011; 404(3):870-876.
37. Gelling R W, Coy D H, Pederson R A et al. GIP(6-30 amide) contains the high affinity binding region of GIP and is a potent inhibitor of GIP1-42 action in vitro. Regulatory Peptides 1997; 69(3):151-154.
38. Deacon C F P. GIP-(3-42) does not antagonize insulinotropic effects of GIP at physiological concentrations. American Journal of Physiology—Endocrinology and Metabolism 2006; 291(3):E468-E475.
39. Gault V A, O'Harte F P M, Harriott P, Flatt P R. Characterization of the Cellular and Metabolic Effects of a Novel Enzyme-Resistant Antagonist of Glucose-Dependent Insulinotropic Polypeptide. Biochemical and Biophysical Research Communications 2002; 290(5):1420-1426.
40. Ravn P, Madhurantakam C, Kunze S et al. Structural and Pharmacological Characterization of Novel Potent and Selective Monoclonal Antibody Antagonists of Glucose-dependent Insulinotropic Polypeptide Receptor. Journal of Biological Chemistry 2013; 288(27):19760-19772.
41. Deacon C F, Plamboeck A, Rosenkilde M M, de Heer J, Holst J J. GIP-(3-42) does not antagonize insulinotropic effects of GIP at physiological concentrations. American Journal of Physiology—Endocrinology and Metabolism 2006; 291(3):E468-E475.
42. Goetze J P, Hunter I, Lippert S K, Bardram L, Rehfeld J F. Processing-independent analysis of peptide hormones and prohormones in plasma. Front Biosci 2012; 17:1804-1815.
43. Goetze J P, Rehfeld J F. Peptide hormones and their prohormones as biomarkers. Biomarkers Med 2009; 3(4): 335-338.
44. Fujita Y, Asadi A, Yang G K, Kwok Y N, Kieffer T J. Differential processing of pro-glucose-dependent insulinotropic polypeptide in gut. American Journal of Physiology—Gastrointestinal and Liver Physiology 2010; 298 (5):G608-G614.
45. Widenmaier S B, Kim S J, Yang G K et al. A GIP Receptor Agonist Exhibits beta-Cell Anti-Apoptotic Actions in Rat Models of Diabetes Resulting in Improved beta-Cell Function and Glycemic Control. PLoS ONE 2010; 5(3):e9590.

46. Graham F L, van der Eb A J. A new technique for the assay of infectivity of human adenovirus 5 DNA. Virology 1973; 52(2):456-467.
47. Kissow H, Hartmann B, Holst J J et al. Glucagon-like peptide-1 (GLP-1) receptor agonism or DPP-4 inhibition does not accelerate neoplasia in carcinogen treated mice. Regulatory Peptides 2012; 179(1GÇô3):91-100.
48. Hoejberg P V, Vilsboell T, Raboel R et al. Four weeks of near-normalisation of blood glucose improves the insulin response to glucagon-like peptide-1 and glucose-dependent insulinotropic polypeptide in patients with type 2 diabetes. Diabetologia 2009; 52(2):199-207.
DEBLASI, A., O'REILLY, K. & MOTULSKY, H. J. 1989. Calculating receptor number from binding experiments using same compound as radioligand and competitor. Trends in Pharmacological Sciences, 10, 227-229.
LAZARENO, S. & BIRDSALL, N. J. 1993. Estimation of competitive antagonist affinity from functional inhibition curves using the Gaddum, Schild and Cheng-Prusoff equations. Br J Pharmacol, 109, 1110-9.
ROSENKILDE, M. M., CAHIR, M., GETHER, U., HJORTH, S. A. & SCHWARTZ, T. W. 1994. Mutations along transmembrane segment II of the NK-1 receptor affect substance P competition with non-peptide antagonists but not substance P binding. J Biol Chem, 269, 28160-4.
HOLST, J. J. & BERSANI, M. 1991. 1—Assays for Peptide Products of Somatostatin Gene Expression. In: CONN, P. M. (ed.) Methods in Neurosciences. Academic Press.
PATHAK, V., GAULT, V. A., FLATT, P. R. & IRWIN, N. 2015. Antagonism of gastric inhibitory polypeptide (GIP) by palmitoylation of GIP analogues with N- and C-terminal modifications improves obesity and metabolic control in high fat fed mice. Mol Cell Endocrinol, 401, 120-9.

Sequences

| | Description | Sequence |
|---|---|---|
| 1 | Human GIP3-30 (hGIP3-30) | EGTFISDYSIAMDKIHQQDFVNWLLAQK |
| 2 | Rat GIP3-30 (rGIP3-30); GIP(3-30)H18R; | EGTFISDYSIAMDKIRQQDFVNWLLAQK |
| 3 | Mouse GIP3-30 (mGIP3-30): GIP(3-30)H18R/K30R | EGTFISDYSIAMDKIRQQDFVNWLLAQR |
| 4 | GIP1-42 (consensus) | YAEGTFISDYSIAMDKIX$_1$QQDFVNWLLAQX$_2$GKKNDWKHNITQ |
| 5 | GIP5-25 | TFISDYSIAMDKIX$_1$QQDFVNW |
| 6 | GIP3-25 | EGTFISDYSIAMDKIX$_1$QQDFVNW |
| 7 | GIP3-26 | EGTFISDYSIAMDKIX$_1$QQDFVNWL |
| 8 | GIP3-27 | EGTFISDYSIAMDKIX$_1$QQDFVNWLL |
| 9 | GIP3-28 | EGTFISDYSIAMDKIX$_1$QQDFVNWLLA |
| 10 | GIP3-29 | EGTFISDYSIAMDKIX$_1$QQDFVNWLLAQ |
| 11 | GIP3-30 (consensus) | EGTFISDYSIAMDKIX$_1$QQDFVNWLLAQX$_2$ |
| 12 | GIP3-31 | EGTFISDYSIAMDKIX$_1$QQDFVNWLLAQX$_2$G |
| 13 | GIP3-32 | EGTFISDYSIAMDKIX$_1$QQDFVNWLLAQX$_2$GK |
| 14 | GIP3-33 | EGTFISDYSIAMDKIX$_1$QQDFVNWLLAQX$_2$GKK |
| 15 | GIP3-34 | EGTFISDYSIAMDKIX$_1$QQDFVNWLLAQX$_2$GKKN |
| 16 | GIP3-35 | EGTFISDYSIAMDKIX$_1$QQDFVNWLLAQX$_2$GKKND |
| 17 | GIP3-36 | EGTFISDYSIAMDKIX$_1$QQDFVNWLLAQX$_2$GKKNDW |
| 18 | GIP3-37 | EGTFISDYSIAMDKIX$_1$QQDFVNWLLAQX$_2$GKKNDWK |
| 19 | GIP3-38 | EGTFISDYSIAMDKIX$_1$QQDFVNWLLAQX$_2$GKKNDWKH |
| 20 | GIP3-39 | EGTFISDYSIAMDKIX$_1$QQDFVNWLLAQX$_2$GKKNDWKHN |
| 21 | GIP3-40 | EGTFISDYSIAMDKIX$_1$QQDFVNWLLAQX$_2$GKKNDWKHNI |
| 22 | GIP3-41 | EGTFISDYSIAMDKIX$_1$QQDFVNWLLAQX$_2$GKKNDWKHNIT |
| 23 | GIP4-25 | GTFISDYSIAMDKIX$_1$QQDFVNW |
| 24 | GIP4-26 | GTFISDYSIAMDKIX$_1$QQDFVNWL |

| | Description | Sequence |
|---|---|---|
| 25 | GIP4-27 | GTFISDYSIAMDKI$X_1$QQDFVNWLL |
| 26 | GIP4-28 | GTFISDYSIAMDKI$X_1$QQDFVNWLLA |
| 27 | GIP4-29 | GTFISDYSIAMDKI$X_1$QQDFVNWLLAQ |
| 28 | GIP4-30 (consensus) | GTFISDYSIAMDKI$X_1$QQDFVNWLLAQ$X_2$ |
| 29 | GIP4-31 | GTFISDYSIAMDKI$X_1$QQDFVNWLLAQ$X_2$G |
| 30 | GIP4-32 | GTFISDYSIAMDKI$X_1$QQDFVNWLLAQ$X_2$GK |
| 31 | GIP4-33 | GTFISDYSIAMDKI$X_1$QQDFVNWLLAQ$X_2$GKK |
| 32 | GIP4-34 | GTFISDYSIAMDKI$X_1$QQDFVNWLLAQ$X_2$GKKN |
| 33 | GIP4-35 | GTFISDYSIAMDKI$X_1$QQDFVNWLLAQ$X_2$GKKND |
| 34 | GIP4-36 | GTFISDYSIAMDKI$X_1$QQDFVNWLLAQ$X_2$GKKNDW |
| 35 | GIP4-37 | GTFISDYSIAMDKI$X_1$QQDFVNWLLAQ$X_2$GKKNDWK |
| 36 | GIP4-38 | GTFISDYSIAMDKI$X_1$QQDFVNWLLAQ$X_2$GKKNDWKH |
| 37 | GIP4-39 | GTFISDYSIAMDKI$X_1$QQDFVNWLLAQ$X_2$GKKNDWKHN |
| 38 | GIP4-40 | GTFISDYSIAMDKI$X_1$QQDFVNWLLAQ$X_2$GKKNDWKHNI |
| 39 | GIP4-41 | GTFISDYSIAMDKI$X_1$QQDFVNWLLAQ$X_2$GKKNDWKHNIT |
| 40 | GIP4-42 | GTFISDYSIAMDKI$X_1$QQDFVNWLLAQ$X_2$GKKNDWKHNITQ |
| 41 | GIP5-26 | TFISDYSIAMDKI$X_1$QQDFVNWL |
| 42 | GIP5-27 | TFISDYSIAMDKI$X_1$QQDFVNWLL |
| 43 | GIP5-28 | TFISDYSIAMDKI$X_1$QQDFVNWLLA |
| 44 | GIP5-29 | TFISDYSIAMDKI$X_1$QQDFVNWLLAQ |
| 45 | GIP5-30 (consensus) | TFISDYSIAMDKI$X_1$QQDFVNWLLAQ$X_2$ |
| 46 | GIP5-31 | TFISDYSIAMDKI$X_1$QQDFVNWLLAQ$X_2$G |
| 47 | GIP5-32 | TFISDYSIAMDKI$X_1$QQDFVNWLLAQ$X_2$GK |
| 48 | GIP5-33 | TFISDYSIAMDKI$X_1$QQDFVNWLLAQ$X_2$GKK |
| 49 | GIP5-34 | TFISDYSIAMDKI$X_1$QQDFVNWLLAQ$X_2$GKKN |
| 50 | GIP5-35 | TFISDYSIAMDKI$X_1$QQDFVNWLLAQ$X_2$GKKND |
| 51 | GIP5-36 | TFISDYSIAMDKI$X_1$QQDFVNWLLAQ$X_2$GKKNDW |
| 52 | GIP5-37 | TFISDYSIAMDKI$X_1$QQDFVNWLLAQ$X_2$GKKNDWK |
| 53 | GIP5-38 | TFISDYSIAMDKI$X_1$QQDFVNWLLAQ$X_2$GKKNDWKH |
| 54 | GIP5-39 | TFISDYSIAMDKI$X_1$QQDFVNWLLAQ$X_2$GKKNDWKHN |
| 55 | GIP5-40 | TFISDYSIAMDKI$X_1$QQDFVNWLLAQ$X_2$GKKNDWKHNI |
| 56 | GIP5-41 | TFISDYSIAMDKI$X_1$QQDFVNWLLAQ$X_2$GKKNDWKHNIT |
| 57 | GIP5-42 | TFISDYSIAMDKI$X_1$QQDFVNWLLAQ$X_2$GKKNDWKHNITQ |
| 58 | Consensus GIP3-42 | EGTFISDYSIAMDKI$X_1$QQDFVNWLLAQ$X_2$GKKNDWKHNITQ |
| 59 | hGIP5-25 | TFISDYSIAMDKIHQQDFVNW |

-continued

| | Description | Sequence |
|---|---|---|
| 60 | mGIP5-25 and rGIP5-25 | TFISDYSIAMDKIRQQDFVNW |
| 61 | GIP5-25 H18A | TFISDYSIAMDKIAQQDFVNW |
| 62 | hGIP3-42 | EGTFISDYSIAMDKIHQQDFVNWLLAQKGKKNDWKHNITQ |
| 63 | rGIP3-42 | EGTFISDYSIAMDKIRQQDFVNWLLAQKGKKNDWKHNITQ |
| 64 | mGIP3-42 | EGTFISDYSIAMDKIRQQDFVNWLLAQRGKKNDWKHNITQ |
| 65 | hGIP1-42 | YAEGTFISDYSIAMDKIHQQDFVNWLLAQKGKKNDWKHNITQ |
| 66 | rGIP1-42 | YAEGTFISDYSIAMDKIRQQDFVNWLLAQKGKKNDWKHNITQ |
| 67 | mGIP1-42 | YAEGTFISDYSIAMDKIRQQDFVNWLLAQRGKKNDWKHNITQ |
| 68 | GIP1-30 (consensus) | YAEGTFISDYSIAMDKI$X_1$QQDFVNWLLAQ$X_2$ |
| 69 | hGIP1-30 | YAEGTFISDYSIAMDKIHQQDFVNWLLAQK |
| 70 | rGIP1-30 | YAEGTFISDYSIAMDKIRQQDFVNWLLAQK |
| 71 | mGIP1-30 | YAEGTFISDYSIAMDKIRQQDFVNWLLAQR |
| 72 | GIP5-25 (H to K) | TFISDYSIAMDKIKQQDFVNW |
| 73 | GIP5-25 (variant) | TFISDYSIAM$X_{0a}X_{0b}$I$X_1$QQDFVNW |
| 74 | GIP3-30 (variant) | EGTFISDYSIAM$X_{0a}X_{0b}$I$X_1$QQDFVNWLLAQ$X_2$ |
| 75 | GIP4-30 (variant) | GTFISDYSIAM$X_{0a}X_{0b}$I$X_1$QQDFVNWLLAQ$X_2$ |
| 76 | GIP5-30 (variant) | TFISDYSIAM$X_{0a}X_{0b}$I$X_1$QQDFVNWLLAQ$X_2$ |
| 77 | hGIP4-30 | GTFISDYSIAMDKIHQQDFVNWLLAQK |
| 78 | hGIP5-30 | TFISDYSIAMDKIHQQDFVNWLLAQK |
| 79 | hGIP(3-30)H18A | EGTFISDYSIAMDKIAQQDFVNWLLAQK |
| 80 | hGIP(3-30)H18K | EGTFISDYSIAMDKIKQQDFVNWLLAQK |
| 81 | hGIP(3-30) D15EH18A | EGTFISDYSIAMEKIAQQDFVNWLLAQK |
| 82 | hGIP(3-30) K16AH18A | EGTFISDYSIAMDAIAQQDFVNWLLAQK |
| 83 | hGIP(3-30)D15E | EGTFISDYSIAMEKIHQQDFVNWLLAQK |
| 84 | hGIP(3-30)D15N | EGTFISDYSIAMNKIHQQDFVNWLLAQK |
| 85 | hGIP(3-30)K16A | EGTFISDYSIAMDAIHQQDFVNWLLAQK |
| 86 | hGIP(3-30)K16H | EGTFISDYSIAMDHIHQQDFVNWLLAQK |
| 87 | hGIP(3-30)K16R | EGTFISDYSIAMDRIHQQDFVNWLLAQK |
| 88 | hGIP(3-30)H18F | EGTFISDYSIAMDKIFQQDFVNWLLAQK |
| 89 | hGIP(3-30)H18W | EGTFISDYSIAMDKIWQQDFVNWLLAQK |
| 90 | hGIP(3-30)K30R | EGTFISDYSIAMDKIHQQDFVNWLLAQR |
| 91 | hGIP(3-30)K30H | EGTFISDYSIAMDKIHQQDFVNWLLAQH |

The invention claimed is:

1. A method of inhibiting or reducing one or more of: i) gastric inhibitory polypeptide (GIP)-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides, and ix) GIP-induced reduction of bone resorption, said method comprising one or more steps of administering to an individual in need thereof a peptide selected from the group consisting of:

a peptide consisting of 28 contiguous amino acids of amino acid sequence EGTFISDYSIAMX$_{oa}$X$_{ob}$IX$_1$QQDFVNWLLAQX$_2$ (GIP3-30; SEQ ID NO: 74):

a peptide consisting of 26 contiguous amino acids of amino acid sequence TFISDYSIAMX$_{oa}$X$_{ob}$IX$_1$QQDFVNWLLAQX$_2$ (GIP5-30; SEQ ID NO: 76), wherein X$_{oa}$ is selected from the group consisting of D, E,
X$_{ob}$ is selected from the group consisting of K, A, H, R,
X$_1$ is selected from the group consisting of H, R, A, K, F, Y and
X$_2$ is selected from the group consisting of K, R, H, A; and
a variant of any one of the above peptides, wherein the amino acid sequence of the variant differs from SEQ ID NO: 74 or SEQ ID NO: 76, only in that the amino acid sequence of the variant comprises one or two amino acid substitutions, wherein said substitutions are selected from the group consisting of: i) substitution of an amino acid having a polar side chain for a different amino acid having a polar side chain wherein amino acids having a polar side chain are Asp, Glu, Lys, Arg, His, Asn, Gln, Ser, Thr, Tyr, and Cys; ii) substitution of an amino acid having a non-polar side chain for a different amino acid having a non-polar side chain wherein amino acids having a non-polar side chain are Gly, Ala, Val, Leu, Ile, Phe, Trp, Pro, and Met; iii) substitution of an amino acid having an aliphatic side chain for a different amino acid having an aliphatic side chain wherein amino acids having a aliphatic side chain are Gly, Ala Val, Leu, and Ile; iv) substitution of an amino acid having a cyclic side chain for a different amino acid having a cyclic side chain wherein amino acids having a cyclic side chain are Phe, Tyr, Trp, His, and Pro; v) substitution of an amino acid having an aromatic side chain for a different amino acid having an aromatic side chain wherein amino acids having an aromatic side chain are Phe, Tyr, and Trp; vi) substitution of an amino acid having an acidic side chain for a different amino acid having an acidic side chain wherein amino acids having an acidic side chain are Asp, and Glu; vii) substitution of an amino acid having a basic side chain for a different amino acid having a basic side chain wherein amino acids having a basic side chain are Lys, Arg, and His; viii) substitution of an amino acid having an amide side chain for a different amino acid having an amide side chain wherein amino acids having an amide side chain are Asn, and Gln; ix) substitution of an amino acid having a hydroxy side chain for a different amino acid having a hydroxy side chain wherein amino acids having a hydroxy side chain are Ser, and Thr; x) substitution of an amino acid having a sulphur-containing side chain for a different amino acid having a sulphur-containing side chain wherein amino acids having a sulphur-containing side chain are Cys, and Met; xi) substitution of a neutral, weakly hydrophobic amino acid for a different neutral, weakly hydrophobic amino acid wherein neutral, weakly hydrophobic amino acids are Pro, Ala, Gly, Ser, and Thr; xii) substitution of a hydrophilic, acidic amino acid for a different hydrophilic, acidic amino acid wherein hydrophilic, acidic amino acids are Gln, Asn, Glu, and Asp, and xiii) substitution of a hydrophobic amino acid for a different hydrophobic amino acid wherein hydrophobic amino acids are Leu, Ile, and Val; wherein said peptide or variant thereof is an antagonist of a GIP receptor (GIPR).

2. The method according to claim 1, wherein said peptide is selected from the group consisting of:
a peptide consisting of 28 contiguous amino acids of sequence
EGTFISDYSIAMDKIX$_1$QQDFVNWLLAQX$_2$
(GIP3-30; SEQ ID NO: 11), a peptide consisting of 26 contiguous amino acids of sequence TFISDYSIAMDKIX$_1$QQDFVNWLLAQX$_2$ (GIP5-30; SEQ ID NO: 45),
wherein X$_1$ is selected from the group consisting of H, R, A, K, F, Y, and
X$_2$ is selected from the group consisting of K, R, H, A, and
a variant of any one of the above peptides, wherein the amino acid sequence of the variant differs from SEQ ID NO: 11 or SEQ ID NO: 45, only in that the amino acid sequence of the variant comprises the one or two amino acid substitutions,
wherein said peptide or variant thereof is an antagonist of a GIP receptor (GIPR).

3. The method according to claim 1, wherein said peptide is selected from the group consisting of:
a peptide consisting of 28 contiguous amino acids of sequence EGTFISDYSIAMDKIHQQDFVNWL-LAQK (hGIP3-30, SEQ ID NO: 1);
a peptide consisting of 28 contiguous amino acids of sequence EGTFISDYSIAMDKIRQQDFVNWL-LAQK (rGIP3-30, SEQ ID NO: 2);
a peptide consisting of 28 contiguous amino acids of sequence: EGTFISDYSIAMDKIRQQDFVNWL-LAQR (mGIP3-30, SEQ ID NO: 3);
a peptide a peptide consisting of 26 contiguous amino acids of sequence TFISDYSIAMDKIHQQDFVNWL-LAQK (hGIP5-30, SEQ ID NO: 78); and
a variant of any one of the above peptides, wherein the amino acid sequence of the variant differs from SEQ ID NO: 1, SEQ ID NO: 2, SEQ ID NO: 3 or SEQ ID NO: 78, only in that the amino acid sequence of the variant comprises the one or two amino acid substitutions,
wherein said peptide or variant thereof is an antagonist of a GIP receptor (GIPR).

4. The method according to claim 1, wherein said peptide is selected from the group consisting of:

```
                                  (hGIP3-30, SEQ ID NO: 1)
EGTFISDYSIAMDKIHQQDFVNWLLAQK, (rGIP3-30, SEQ ID NO: 2)
EGTFISDYSIAMDKIRQQDFVNWLLAQK, (mGIP3-30, SEQ ID NO: 3)
EGTFISDYSIAMDKIRQQDFVNWLLAQR, (hGIP5-30, SEQ ID NO: 78)
TFISDYSIAMDKIHQQDFVNWLLAQK, (hGIP(3-30)H18A; SEQ ID NO: 79)
EGTFISDYSIAMDKIAQQDFVNWLLAQK, (hGIP(3-30)H18K; SEQ ID NO: 80)
EGTFISDYSIAMDKIKQQDFVNWLLAQ, (hGIP(3-30)D15EH18A; SEQ ID NO: 81)
EGTFISDYSIAMEKIAQQDFVNWLLAQK, (hGIP(3-30)K16AH18A; SEQ ID NO: 82)
EGTFISDYSIAMDAIAQQDFVNWLLAQK, (hGIP(3-30)D15E; SEQ ID NO: 83)
EGTFISDYSIAMEKIHQQDFVNWLLAQK, (hGIP(3-30)D15N; SEQ ID NO: 84)
EGTFISDYSIAMNKIHQQDFVNWLLAQK, (hGIP(3-30)K16A; SEQ ID NO: 85)
EGTFISDYSIAMDAIHQQDFVNWLLAQK, (hGIP(3-30)K16H; SEQ ID NO: 86)
EGTFISDYSIAMDHIHQQDFVNWLLAQK,
```

```
                (hGIP(3-30)K16R; SEQ ID NO: 87)
EGTFISDYSIAMDRIHQQDFVNWLLAQK, (hGIP(3-30)H18F; SEQ ID NO: 88)
EGTFISDYSIAMDKIFQQDFVNWLLAQK, (hGIP(3-30)H18W; SEQ ID NO: 89)
EGTFISDYSIAMDKIWQQDFVNWLLAQK, (hGIP(3-30)K30R SEQ ID NO: 90)
EGTFISDYSIAMDKIHQQDFVNWLLAQR,
and (hGIP(3-30)K30H; SEQ ID NO: 91)
EGTFISDYSIAMDKIHQQDFVNWLLAQH.
```

5. The method according to claim 1, wherein said peptide is C-terminally amidated (—NH$_2$) and/or N-terminally acetylated (COCH$_3$).

6. The method of claim 5, wherein said peptide is selected from the group consisting of: EGTFISDYSIAMD-KIHQQDFVNWLLAQK-NH$_2$ (SEQ ID NO:92); TFISDY-SIAMDKIHQQDFVNWLLAQK-NH$_2$ (SEQ ID NO:94); and a variant of any one of the above peptides, wherein the amino acid sequence of the variant differs from SEQ ID NO: 92 or SEQ ID NO: 94, only in that the amino acid sequence of the variant comprises the one or two amino acid substitutions, wherein said peptide or variant thereof is an antagonist of a GIP receptor (GIPR).

7. The method of claim 5, wherein said peptide is selected from the group consisting of:
EGTFISDYSIAMDKIHQQDFVNWLLAQK-NH$_2$ (SEQ ID NO:92); and
TFISDYSIAMDKIHQQDFVNWLLAQK-NH$_2$ (SEQ ID NO:94).

8. The method according to claim 1, wherein said peptide
i) binds to a GIP-receptor (GIPR),
ii) antagonizes GIP1-42-induced activation of a GIPR,
iii) displaces GIP1-42 from a GIPR,
iv) is a competitive antagonist of a GIP-receptor,
v) has an affinity for a GIPR which is higher than the affinity of GIP3-42 for the same GIPR,
vi) is capable of inhibiting and/or antagonizing somatostatin secretion induced by native GIP,
vii) is capable of inhibiting and/or antagonizing insulin secretion induced by native GIP, and/or
viii) is capable of inhibiting and/or antagonizing glucagon secretion induced by native GIP.

9. The method according to claim 1, wherein said peptide is encoded by a nucleic acid construct.

10. A method of treating one or more of: metabolic syndrome, obesity, pre-diabetes, diabetes mellitus type 2, insulin resistance, elevated fasting glucose, elevated fasting serum triglyceride level, low high-density lipoprotein (HDL) levels, fatty acid metabolism disorder, cardiovascular disease, elevated blood pressure and atherosclerosis,
said method comprising one or more steps of administering to an individual in need thereof a peptide selected from the group consisting of:
a peptide consisting of 28 contiguous amino acids of amino acid sequence EGTFISDYSIAMX$_{oa}$X$_{ob}$IX$_1$QQDFVNWLLAQX$_2$ (GIP3-30; SEQ ID NO: 74);
a peptide consisting of 26 contiguous amino acids of amino acid sequence TFISDYSIAMX$_{oa}$X$_{ob}$IX$_1$QQDFVNWLLAQX$_2$ (GIP5-30; SEQ ID NO: 76), wherein X$_{oa}$ is selected from the group consisting of D, E,
X$_{ob}$ is selected from the group consisting of K, A, H, R,
X$_1$ is selected from the group consisting of H, R, A, K, F, Y and
X$_2$ is selected from the group consisting of K, R, H, A; and
a variant of any one of the above peptides, wherein the amino acid sequence of the variant differs from SEQ ID NO: 74 or SEQ ID NO: 76, only in that the amino acid sequence of the variant comprises one or two amino acid substitutions, wherein said substitutions are selected from the group consisting of: i) substitution of an amino acid having a polar side chain for a different amino acid having a polar side chain wherein amino acids having a polar side chain are Asp, Glu, Lys, Arg, His, Asn, Gln, Ser, Thr, Tyr, and Cys; ii) substitution of an amino acid having a non-polar side chain for a different amino acid having a non-polar side chain wherein amino acids having a non-polar side chain are Gly, Ala, Val, Leu, Ile, Phe, Trp, Pro, and Met; iii) substitution of an amino acid having an aliphatic side chain for a different amino acid having an aliphatic side chain wherein amino acids having a aliphatic side chain are Gly, Ala Val, Leu, and Ile; iv) substitution of an amino acid having a cyclic side chain for a different amino acid having a cyclic side chain wherein amino acids having a cyclic side chain are Phe, Tyr, Trp, His, and Pro; v) substitution of an amino acid having an aromatic side chain for a different amino acid having an aromatic side chain wherein amino acids having an aromatic side chain are Phe, Tyr, and Trp; vi) substitution of an amino acid having an acidic side chain for a different amino acid having an acidic side chain wherein amino acids having an acidic side chain are Asp, and Gu; vii) substitution of an amino acid having a basic side chain for a different amino acid having a basic side chain wherein amino acids having a basic side chain are Lys, Arg, and His; viii) substitution of an amino acid having an amide side chain for a different amino acid having an amide side chain wherein amino acids having an amide side chain are Asn, and Gln; ix) substitution of an amino acid having a hydroxy side chain for a different amino acid having a hydroxy side chain wherein amino acids having a hydroxy side chain are Ser, and Thr; x) substitution of an amino acid having a sulphur-containing side chain for a different amino acid having a sulphur-containing side chain wherein amino acids having a sulphur-containing side chain are Cys, and Met; xi) substitution of a neutral, weakly hydrophobic amino acid for a different neutral, weakly hydrophobic amino acid wherein neutral, weakly hydrophobic amino acids are Pro, Ala, Gly, Ser, and Thr; xii) substitution of a hydrophilic, acidic amino acid for a different hydrophilic, acidic amino acid wherein hydrophilic, acidic amino acids are Gln, Asn, Glu, and Asp, and xii) substitution of a hydrophobic amino acid for a different hydrophobic amino acid wherein hydrophobic amino acids are Leu, Ile, and Val; wherein said peptide or variant thereof is an antagonist of a GIP receptor (GIPR).

11. The method according to claim 10, wherein said peptide is selected from the group consisting of:
a peptide consisting of 28 contiguous amino acids of sequence EGTFISDYSIAMDKIX₁QQDFVNWLLAQX₂ (GIP3-30; SEQ ID NO: 11),
a peptide consisting of 26 contiguous amino acids of sequence TFISDYSIAMDKIX₁QQDFVNWLLAQX₂ (GIP5-30; SEQ ID NO: 45),
wherein X₁ is selected from the group consisting of H, R, A, K, F, Y, and
X₂ is selected from the group consisting of K, R, H, A, and
a variant of any one of the above peptides, wherein the amino acid sequence of the variant differs from SEQ ID NO: 11 or SEQ ID NO: 45, only in that the amino acid sequence of the variant comprises the one or two amino acid substitutions,
wherein said peptide or variant thereof is an antagonist of a GIP receptor (GIPR).

12. The method according to claim 10, wherein said peptide is selected from the group consisting of:
a peptide consisting of 28 contiguous amino acids of sequence EGTFISDYSIAMDKIHQQDFVNWLLAQK (hGIP3-30, SEQ ID NO: 1);
a peptide consisting of 28 contiguous amino acids of sequence EGTFISDYSIAMDKIRQQDFVNWLLAQK (rGIP3-30, SEQ ID NO: 2);
a peptide consisting of 28 contiguous amino acids of sequence EGTFISDYSIAMDKIRQQDFVNWLLAQR (mGIP3-30, SEQ ID NO: 3);
a peptide consisting of 26 contiguous amino acids of sequence TFISDYSIAMDKIHQQDFVNWLLAQK (hGIP5-30, SEQ ID NO: 78); and
a variant of any one of the above peptides, wherein the amino acid sequence of the variant differs from SEQ ID NO: 1, SEQ ID NO: 2, SEQ ID NO:3 or SEQ ID NO: 78, only in that the amino acid sequence of the variant comprises the one or two amino acid substitutions,
wherein said peptide or variant thereof is an antagonist of a GIP receptor (GIPR).

13. The method according to claim 10, wherein said peptide is selected from the group consisting of:

```
                          (hGIP3-30, SEQ ID NO: 1)
EGTFISDYSIAMDKIHQQDFVNWLLAQK, (rGIP3-30, SEQ ID NO: 2)
EGTFISDYSIAMDKIRQQDFVNWLLAQK, (mGIP3-30, SEQ ID NO: 3)
EGTFISDYSIAMDKIRQQDFVNWLLAQR, (hGIP5-30, SEQ ID NO: 78)
TFISDYSIAMDKIHQQDFVNWLLAQK, (hGIP(3-30)H18A; SEQ ID NO: 79)
EGTFISDYSIAMDKIAQQDFVNWLLAQK, (hGIP(3-30)H18K; SEQ ID NO: 80)
EGTFISDYSIAMDKIKQQDFVNWLLAQ, (hGIP(3-30)D15EH18A; SEQ ID NO: 81)
EGTFISDYSIAMEKIAQQDFVNWLLAQK, (hGIP(3-30)K16AH18A; SEQ ID NO: 82)
EGTFISDYSIAMDAIAQQDFVNWLLAQK, (hGIP(3-30)D15E; SEQ ID NO: 83)
EGTFISDYSIAMEKIHQQDFVNWLLAQK, (hGIP(3-30)D15N; SEQ ID NO: 84)
EGTFISDYSIAMNKIHQQDFVNWLLAQK, (hGIP(3-30)K16A; SEQ ID NO: 85)
EGTFISDYSIAMDAIHQQDFVNWLLAQK, (hGIP(3-30)K16H; SEQ ID NO: 86)
EGTFISDYSIAMDHIHQQDFVNWLLAQK, (hGIP(3-30)K16R; SEQ ID NO: 87)
EGTFISDYSIAMDRIHQQDFVNWLLAQK, (hGIP(3-30)H18F; SEQ ID NO: 88)
EGTFISDYSIAMDKIFQQDFVNWLLAQK, (hGIP(3-30)H18W; SEQ ID NO: 89)
EGTFISDYSIAMDKIWQQDFVNWLLAQK, (hGIP(3-30)K30R SEQ ID NO: 90)
EGTFISDYSIAMDKIHQQDFVNWLLAQR,
and (hGIP(3-30)K30H; SEQ ID NO: 91)
EGTFISDYSIAMDKIHQQDFVNWLLAQH.
```

14. The method according to claim 10, wherein said peptide is C-terminally amidated (—NH₂) and/or N-terminally acetylated (COCH₃).

15. The method according to claim 10, wherein said peptide
i) binds to a GIP-receptor (GIPR),
ii) antagonises GIP1-42-induced activation of a GIPR,
iii) displaces GIP1-42 from a GIPR,
iv) is a competitive antagonist of a GIP-receptor,
v) has an affinity for a GIPR which is higher than the affinity of GIP3-42 for the same GIPR,
vi) is capable of inhibiting and/or antagonising somatostatin secretion induced by native GIP,
vii) is capable of inhibiting and/or antagonising insulin secretion induced by native GIP, and/or
viii) is capable of inhibiting and/or antagonising glucagon secretion induced by native GIP.

16. The method according to claim 10, wherein said peptide is encoded by a nucleic acid construct.

17. The method of claim 10, wherein said peptide is selected from the group consisting of: EGTFISDYSIAMDKIHQQDFVNWLLAQK-NH₂ (SEQ ID NO:92): TFISDYSIAMDKIHQQDFVNWLLAQK-NH₂ (SEQ ID NO:94); and a variant of any one of the above peptides, wherein the amino acid sequence of the variant differs from SEQ ID NO: 92 or SEQ ID NO: 94, only in that the amino acid sequence of the variant comprises the one or two amino acid substitutions, wherein said peptide or variant thereof is an antagonist of a GIP receptor (GIPR).

18. The method of claim 10, wherein said peptide is selected from the group consisting of:
EGTFISDYSIAMDKIHQQDFVNWLLAQK-NH₂ (SEQ ID NO:92); and
TFISDYSIAMDKIHQQDFVNWLLAQK-NH₂ (SEQ ID NO:94).

* * * * *

SEQUENCE LISTING

<160> NUMBER OF SEQ ID NOS: 94

<210> SEQ ID NO 1
<211> LENGTH: 28
<212> TYPE: PRT
<213> ORGANISM: Homo sapiens

<400> SEQUENCE: 1

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 2
<211> LENGTH: 28
<212> TYPE: PRT
<213> ORGANISM: Rattus norvegicus

<400> SEQUENCE: 2

Glu Gly Thr Phe Ile Ser Asp Tyr Ser Ile Ala Met Asp Lys Ile Arg
1               5                   10                  15

Gln Gln Asp Phe Val Asn Trp Leu Leu Ala Gln Lys
            20                  25

<210> SEQ ID NO 3
<211> LENGTH: 28
<212> TYPE: PRT
<213> ORGANISM: Mus musculus

<400> SEQUENCE: 3

Glu Gly Thr Phe Ile Ser Asp Tyr Ser Ile Ala Met Asp Lys Ile Arg
1               5                   10                  15

Gln Gln Asp Phe Val Asn Trp Leu Leu Ala Gln Arg
            20                  25

<210> SEQ ID NO 4
<211> LENGTH: 42
<212> TYPE: PRT
<213> ORGANISM: Artificial sequence
<220> FEATURE:
<223> OTHER INFORMATION: GIP analogue
<220> FEATURE:
<221> NAME/KEY: MISC_FEATURE
<222> LOCATION: (1)..(42)
<223> OTHER INFORMATION: <GIP1-42 (consensus); X is independently any
      amino acid

<400> SEQUENCE: 4

Tyr Ala Glu Gly Thr Phe Ile Ser Asp Tyr Ser Ile Ala Met Asp Lys
1               5                   10                  15

Ile Xaa Gln Gln Asp Phe Val Asn Trp Leu Leu Ala Gln Xaa Gly Lys
            20                  25                  30

Lys Asn Asp Trp Lys His Asn Ile Thr Gln
            35                  40

<210> SEQ ID NO 5
<211> LENGTH: 21
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(21)
<223> OTHER INFORMATION: GIP5-25; X is independently any amino acid

<400> SEQUENCE: 5

Thr Phe Ile Ser Asp Tyr Ser Ile Ala Met Asp Lys Ile Xaa Gln Gln
1               5                   10                  15

Asp Phe Val Asn Trp
            20

<210> SEQ ID NO 6
<211> LENGTH: 23
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(23)
<223> OTHER INFORMATION: GIP3-25; X is independently any amino acid

<400> SEQUENCE: 6

Glu Gly Thr Phe Ile Ser Asp Tyr Ser Ile Ala Met Asp Lys Ile Xaa
1               5                   10                  15

Gln Gln Asp Phe Val Asn Trp
            20

<210> SEQ ID NO 7
<211> LENGTH: 24
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(24)
<223> OTHER INFORMATION: GIP3-26; X is independently any amino acid

<400> SEQUENCE: 7

Glu Gly Thr Phe Ile Ser Asp Tyr Ser Ile Ala Met Asp Lys Ile Xaa
1               5                   10                  15

Gln Gln Asp Phe Val Asn Trp Leu
            20

<210> SEQ ID NO 8
<211> LENGTH: 25
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(25)
<223> OTHER INFORMATION: GIP3-27; X is independently any amino acid

<400> SEQUENCE: 8

Glu Gly Thr Phe Ile Ser Asp Tyr Ser Ile Ala Met Asp Lys Ile Xaa
1               5                   10                  15

Gln Gln Asp Phe Val Asn Trp Leu Leu
            20                  25

<210> SEQ ID NO 9
<211> LENGTH: 26
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(26)

<223> OTHER INFORMATION: GIP3-28; X is independently any amino acid

<400> SEQUENCE: 9

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala
            20                  25

<210> SEQ ID NO 10
<211> LENGTH: 27
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(27)
<223> OTHER INFORMATION: GIP3-29; X is independently any amino acid

<400> SEQUENCE: 10

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln
            20                  25

<210> SEQ ID NO 11
<211> LENGTH: 28
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(28)
<223> OTHER INFORMATION: GIP3-30 consensus; X is independently any amino
      acid

<400> SEQUENCE: 11

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa
            20                  25

<210> SEQ ID NO 12
<211> LENGTH: 29
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(29)
<223> OTHER INFORMATION: GIP3-31; X is independently any amino acid

<400> SEQUENCE: 12

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly
            20                  25

<210> SEQ ID NO 13
<211> LENGTH: 30
<212> TYPE: PRT
<213> ORGANISM: Artificial sequence
<220> FEATURE:
<223> OTHER INFORMATION: GIP analogues
<220> FEATURE:

-continued

```
<221> NAME/KEY: MISC_FEATURE
<222> LOCATION: (1)..(30)
<223> OTHER INFORMATION: GIP3-32; X is independently any amino acid

<400> SEQUENCE: 13

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys
            20                  25                  30

<210> SEQ ID NO 14
<211> LENGTH: 31
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(31)
<223> OTHER INFORMATION: GIP3-33; X is independently any amino acid

<400> SEQUENCE: 14

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys
            20                  25                  30

<210> SEQ ID NO 15
<211> LENGTH: 32
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(32)
<223> OTHER INFORMATION: GIP3-34; X is independently any amino acid

<400> SEQUENCE: 15

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

<210> SEQ ID NO 16
<211> LENGTH: 33
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(33)
<223> OTHER INFORMATION: GIP3-35; X is independently any amino acid

<400> SEQUENCE: 16

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp

<210> SEQ ID NO 17
<211> LENGTH: 34
<212> TYPE: PRT
<213> ORGANISM: Artificial sequence
```

```
<220> FEATURE:
<223> OTHER INFORMATION: GIP analogues
<220> FEATURE:
<221> NAME/KEY: MISC_FEATURE
<222> LOCATION: (1)..(34)
<223> OTHER INFORMATION: GIP3-36 X is independently any amino acid

<400> SEQUENCE: 17

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp

<210> SEQ ID NO 18
<211> LENGTH: 35
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(35)
<223> OTHER INFORMATION: GIP3-37; X is independently any amino acid

<400> SEQUENCE: 18

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp Lys
        35

<210> SEQ ID NO 19
<211> LENGTH: 36
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(36)
<223> OTHER INFORMATION: GIP3-38; X is independently any amino acid

<400> SEQUENCE: 19

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp Lys His
        35

<210> SEQ ID NO 20
<211> LENGTH: 37
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(37)
<223> OTHER INFORMATION: GIP3-39; X is independently any amino acid

<400> SEQUENCE: 20

Glu Gly Thr Phe Ile Ser Asp Tyr Ser Ile Ala Met Asp Lys Ile Xaa
1               5                   10                  15
```

Gln Gln Asp Phe Val Asn Trp Leu Leu Ala Gln Xaa Gly Lys Lys Asn
            20                  25                  30

Asp Trp Lys His Asn
        35

<210> SEQ ID NO 21
<211> LENGTH: 38
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (3)..(40)
<223> OTHER INFORMATION: GIP3-40; X is independently any amino acid

<400> SEQUENCE: 21

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp Lys His Asn Ile
        35

<210> SEQ ID NO 22
<211> LENGTH: 39
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(39)
<223> OTHER INFORMATION: GIP3-41; X is independently any amino acid

<400> SEQUENCE: 22

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp Lys His Asn Ile Thr
        35

<210> SEQ ID NO 23
<211> LENGTH: 22
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(22)
<223> OTHER INFORMATION: GIP4-25; X is independently any amino acid

<400> SEQUENCE: 23

Gly Thr Phe Ile Ser Asp Tyr Ser Ile Ala Met Asp Lys Ile Xaa Gln
1               5                   10                  15

Gln Asp Phe Val Asn Trp
            20

<210> SEQ ID NO 24
<211> LENGTH: 23
<212> TYPE: PRT
<213> ORGANISM: Artificial sequence
<220> FEATURE:

```
<223> OTHER INFORMATION: GIP analogues
<220> FEATURE:
<221> NAME/KEY: MISC_FEATURE
<222> LOCATION: (1)..(23)
<223> OTHER INFORMATION: GIP4-26; X is independently any amino acid

<400> SEQUENCE: 24

Gly Thr Phe Ile Ser Asp Tyr Ser Ile Ala Met Asp Lys Ile Xaa Gln
1               5                   10                  15

Gln Asp Phe Val Asn Trp Leu
            20

<210> SEQ ID NO 25
<211> LENGTH: 24
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(24)
<223> OTHER INFORMATION: GIP4-27; X is independently any amino acid

<400> SEQUENCE: 25

Gly Thr Phe Ile Ser Asp Tyr Ser Ile Ala Met Asp Lys Ile Xaa Gln
1               5                   10                  15

Gln Asp Phe Val Asn Trp Leu Leu
            20

<210> SEQ ID NO 26
<211> LENGTH: 25
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(25)
<223> OTHER INFORMATION: GIP4-28; X is independently any amino acid

<400> SEQUENCE: 26

Gly Thr Phe Ile Ser Asp Tyr Ser Ile Ala Met Asp Lys Ile Xaa Gln
1               5                   10                  15

Gln Asp Phe Val Asn Trp Leu Leu Ala
            20                  25

<210> SEQ ID NO 27
<211> LENGTH: 26
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(26)
<223> OTHER INFORMATION: GIP4-29; X is independently any amino acid

<400> SEQUENCE: 27

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln
            20                  25

<210> SEQ ID NO 28
<211> LENGTH: 27
<212> TYPE: PRT
<213> ORGANISM: Artificial sequence
```

```
<220> FEATURE:
<223> OTHER INFORMATION: GIP analogues
<220> FEATURE:
<221> NAME/KEY: MISC_FEATURE
<222> LOCATION: (1)..(27)
<223> OTHER INFORMATION: GIP4-30 consensus; X is independently any amino
      acid

<400> SEQUENCE: 28

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa
            20                  25

<210> SEQ ID NO 29
<211> LENGTH: 28
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(28)
<223> OTHER INFORMATION: GIP4-31; X is independently any amino acid

<400> SEQUENCE: 29

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly
            20                  25

<210> SEQ ID NO 30
<211> LENGTH: 29
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(29)
<223> OTHER INFORMATION: GIP4-32; X is independently any amino acid

<400> SEQUENCE: 30

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys
            20                  25

<210> SEQ ID NO 31
<211> LENGTH: 30
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(30)
<223> OTHER INFORMATION: GIP4-33; X is independently any amino acid

<400> SEQUENCE: 31

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys
            20                  25                  30

<210> SEQ ID NO 32
<211> LENGTH: 31
```

```
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(31)
<223> OTHER INFORMATION: GIP4-34; X is independently any amino acid

<400> SEQUENCE: 32

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn
            20                  25                  30

<210> SEQ ID NO 33
<211> LENGTH: 32
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(32)
<223> OTHER INFORMATION: GIP4-35; X is independently any amino acid

<400> SEQUENCE: 33

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

<210> SEQ ID NO 34
<211> LENGTH: 33
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(33)
<223> OTHER INFORMATION: GIP4-36; X is independently any amino acid

<400> SEQUENCE: 34

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp

<210> SEQ ID NO 35
<211> LENGTH: 34
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(34)
<223> OTHER INFORMATION: GIP4-37; X is independently any amino acid

<400> SEQUENCE: 35

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30
```

Trp Lys

```
<210> SEQ ID NO 36
<211> LENGTH: 35
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(35)
<223> OTHER INFORMATION: GIP4-38; X is independently any amino acid

<400> SEQUENCE: 36

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp Lys His
        35

<210> SEQ ID NO 37
<211> LENGTH: 36
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(36)
<223> OTHER INFORMATION: GIP4-39; X is independently any amino acid

<400> SEQUENCE: 37

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp Lys His Asn
        35

<210> SEQ ID NO 38
<211> LENGTH: 37
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(37)
<223> OTHER INFORMATION: GIP4-40; X is independently any amino acid

<400> SEQUENCE: 38

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp Lys His Asn Ile
        35

<210> SEQ ID NO 39
<211> LENGTH: 38
<212> TYPE: PRT
<213> ORGANISM: Artificial sequence
<220> FEATURE:
<223> OTHER INFORMATION: GIP analogues
<220> FEATURE:
```

```
<221> NAME/KEY: MISC_FEATURE
<222> LOCATION: (1)..(38)
<223> OTHER INFORMATION: GIP4-41; X is independently any amino acid

<400> SEQUENCE: 39

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp Lys His Asn Ile Thr
        35

<210> SEQ ID NO 40
<211> LENGTH: 39
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(39)
<223> OTHER INFORMATION: GIP4-42; X is independently any amino acid

<400> SEQUENCE: 40

Gly Thr Phe Ile Ser Asp Tyr Ser Ile Ala Met Asp Lys Ile Xaa Gln
1               5                   10                  15

Gln Asp Phe Val Asn Trp Leu Leu Ala Gln Xaa Gly Lys Lys Asn Asp
            20                  25                  30

Trp Lys His Asn Ile Thr Gln
        35

<210> SEQ ID NO 41
<211> LENGTH: 22
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(22)
<223> OTHER INFORMATION: GIP5-26; X is independently any amino acid

<400> SEQUENCE: 41

Thr Phe Ile Ser Asp Tyr Ser Ile Ala Met Asp Lys Ile Xaa Gln Gln
1               5                   10                  15

Asp Phe Val Asn Trp Leu
            20

<210> SEQ ID NO 42
<211> LENGTH: 23
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(23)
<223> OTHER INFORMATION: GIP5-27; X is independently any amino acid

<400> SEQUENCE: 42

Thr Phe Ile Ser Asp Tyr Ser Ile Ala Met Asp Lys Ile Xaa Gln Gln
1               5                   10                  15

Asp Phe Val Asn Trp Leu Leu
            20
```

```
<210> SEQ ID NO 43
<211> LENGTH: 24
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(24)
<223> OTHER INFORMATION: GIP5-28; X is independently any amino acid

<400> SEQUENCE: 43

Thr Phe Ile Ser Asp Tyr Ser Ile Ala Met Asp Lys Ile Xaa Gln Gln
1               5                   10                  15

Asp Phe Val Asn Trp Leu Leu Ala
            20

<210> SEQ ID NO 44
<211> LENGTH: 25
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(25)
<223> OTHER INFORMATION: GIP5-29; X is independently any amino acid

<400> SEQUENCE: 44

Thr Phe Ile Ser Asp Tyr Ser Ile Ala Met Asp Lys Ile Xaa Gln Gln
1               5                   10                  15

Asp Phe Val Asn Trp Leu Leu Ala Gln
            20                  25

<210> SEQ ID NO 45
<211> LENGTH: 26
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(26)
<223> OTHER INFORMATION: GIP5-30 consensus; X is independently any amino
      acid

<400> SEQUENCE: 45

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa
            20                  25

<210> SEQ ID NO 46
<211> LENGTH: 27
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(27)
<223> OTHER INFORMATION: GIP5-31; X is independently any amino acid

<400> SEQUENCE: 46

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly
            20                  25
```

```
<210> SEQ ID NO 47
<211> LENGTH: 28
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(28)
<223> OTHER INFORMATION: GIP5-32; X is independently any amino acid

<400> SEQUENCE: 47

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys
            20                  25

<210> SEQ ID NO 48
<211> LENGTH: 29
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(29)
<223> OTHER INFORMATION: GIP5-22; X is independently any amino acid

<400> SEQUENCE: 48

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys
            20                  25

<210> SEQ ID NO 49
<211> LENGTH: 30
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(30)
<223> OTHER INFORMATION: GIP5-34; X is independently any amino acid

<400> SEQUENCE: 49

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn
            20                  25                  30

<210> SEQ ID NO 50
<211> LENGTH: 31
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(31)
<223> OTHER INFORMATION: GIP5-35; X is independently any amino acid

<400> SEQUENCE: 50

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp
```

<210> SEQ ID NO 51
<211> LENGTH: 32
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(32)
<223> OTHER INFORMATION: GIP5-36; X is independently any amino acid

<400> SEQUENCE: 51

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
            20                  25                  30

<210> SEQ ID NO 52
<211> LENGTH: 33
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(33)
<223> OTHER INFORMATION: GIP5-37; X is independently any amino acid

<400> SEQUENCE: 52

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
            20                  25                  30

Lys

<210> SEQ ID NO 53
<211> LENGTH: 34
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(34)
<223> OTHER INFORMATION: GIP5-38; X is independently any amino acid

<400> SEQUENCE: 53

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
            20                  25                  30

Lys His

<210> SEQ ID NO 54
<211> LENGTH: 35
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(35)
<223> OTHER INFORMATION: GIP5-39; X is independently any amino acid

<400> SEQUENCE: 54

```
Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
                20                  25                  30

Lys His Asn
        35

<210> SEQ ID NO 55
<211> LENGTH: 36
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(36)
<223> OTHER INFORMATION: GIP5-40; X is independently any amino acid

<400> SEQUENCE: 55

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
                20                  25                  30

Lys His Asn Ile
        35

<210> SEQ ID NO 56
<211> LENGTH: 37
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(37)
<223> OTHER INFORMATION: GIP5-41; X is independently any amino acid

<400> SEQUENCE: 56

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
                20                  25                  30

Lys His Asn Ile Thr
        35

<210> SEQ ID NO 57
<211> LENGTH: 38
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(38)
<223> OTHER INFORMATION: GIP5-42; X is independently any amino acid

<400> SEQUENCE: 57

Thr Phe Ile Ser Asp Tyr Ser Ile Ala Met Asp Lys Ile Xaa Gln Gln
1               5                   10                  15

Asp Phe Val Asn Trp Leu Leu Ala Gln Xaa Gly Lys Lys Asn Asp Trp
                20                  25                  30

Lys His Asn Ile Thr Gln
        35
```

<210> SEQ ID NO 58
<211> LENGTH: 40
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(40)
<223> OTHER INFORMATION: Consensus GIP3-42; X is independently any amino acid

<400> SEQUENCE: 58

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Xaa Gly Lys Lys Asn
            20                  25                  30

Asp Trp Lys His Asn Ile Thr Gln
        35                  40

<210> SEQ ID NO 59
<211> LENGTH: 21
<212> TYPE: PRT
<213> ORGANISM: Homo sapiens

<400> SEQUENCE: 59

Thr Phe Ile Ser Asp Tyr Ser Ile Ala Met Asp Lys Ile His Gln Gln
1               5                   10                  15

Asp Phe Val Asn Trp
            20

<210> SEQ ID NO 60
<211> LENGTH: 21
<212> TYPE: PRT
<213> ORGANISM: Mus musculus

<400> SEQUENCE: 60

Thr Phe Ile Ser Asp Tyr Ser Ile Ala Met Asp Lys Ile Arg Gln Gln
1               5                   10                  15

Asp Phe Val Asn Trp
            20

<210> SEQ ID NO 61
<211> LENGTH: 21
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(21)
<223> OTHER INFORMATION: GIP5-25 H18A

<400> SEQUENCE: 61

Thr Phe Ile Ser Asp Tyr Ser Ile Ala Met Asp Lys Ile Ala Gln Gln
1               5                   10                  15

Asp Phe Val Asn Trp
            20

<210> SEQ ID NO 62
<211> LENGTH: 40
<212> TYPE: PRT
<213> ORGANISM: Homo sapiens

<400> SEQUENCE: 62

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Gly Lys Lys Asn
                20                  25                  30

Asp Trp Lys His Asn Ile Thr Gln
        35                  40

<210> SEQ ID NO 63
<211> LENGTH: 40
<212> TYPE: PRT
<213> ORGANISM: Rattus norvegicus

<400> SEQUENCE: 63

Glu Gly Thr Phe Ile Ser Asp Tyr Ser Ile Ala Met Asp Lys Ile Arg
1               5                   10                  15

Gln Gln Asp Phe Val Asn Trp Leu Leu Ala Gln Lys Gly Lys Lys Asn
                20                  25                  30

Asp Trp Lys His Asn Ile Thr Gln
        35                  40

<210> SEQ ID NO 64
<211> LENGTH: 40
<212> TYPE: PRT
<213> ORGANISM: Mus musculus

<400> SEQUENCE: 64

Glu Gly Thr Phe Ile Ser Asp Tyr Ser Ile Ala Met Asp Lys Ile Arg
1               5                   10                  15

Gln Gln Asp Phe Val Asn Trp Leu Leu Ala Gln Arg Gly Lys Lys Asn
                20                  25                  30

Asp Trp Lys His Asn Ile Thr Gln
        35                  40

<210> SEQ ID NO 65
<211> LENGTH: 42
<212> TYPE: PRT
<213> ORGANISM: Homo sapiens

<400> SEQUENCE: 65

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 66
<211> LENGTH: 42
<212> TYPE: PRT
<213> ORGANISM: Rattus norvegicus

<400> SEQUENCE: 66

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 67
<211> LENGTH: 42
<212> TYPE: PRT
<213> ORGANISM: Mus musculus

<400> SEQUENCE: 67

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Asn Asp Trp Lys His Asn Ile Thr Gln
        35                  40

<210> SEQ ID NO 68
<211> LENGTH: 30
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(30)
<223> OTHER INFORMATION: Consensus GIP1-30; X is independently any amino
      acid

<400> SEQUENCE: 68

Tyr Ala Glu Gly Thr Phe Ile Ser Asp Tyr Ser Ile Ala Met Asp Lys
1               5                   10                  15

Ile Xaa Gln Gln Asp Phe Val Asn Trp Leu Leu Ala Gln Xaa
            20                  25                  30

<210> SEQ ID NO 69
<211> LENGTH: 30
<212> TYPE: PRT
<213> ORGANISM: Homo sapiens

<400> SEQUENCE: 69

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 70
<211> LENGTH: 30
<212> TYPE: PRT
<213> ORGANISM: Rattus norvegicus

<400> SEQUENCE: 70

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 71
<211> LENGTH: 30
<212> TYPE: PRT
<213> ORGANISM: Mus musculus

<400> SEQUENCE: 71

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg
            20                  25                  30

```
<210> SEQ ID NO 72
<211> LENGTH: 21
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(21)
<223> OTHER INFORMATION: GIP5-25 (H18K)

<400> SEQUENCE: 72

Thr Phe Ile Ser Asp Tyr Ser Ile Ala Met Asp Lys Ile Lys Gln Gln
1               5                   10                  15

Asp Phe Val Asn Trp
            20

<210> SEQ ID NO 73
<211> LENGTH: 21
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(21)
<223> OTHER INFORMATION: GIP5-25 (variant); X is independently any amino
      acid

<400> SEQUENCE: 73

Thr Phe Ile Ser Asp Tyr Ser Ile Ala Met Xaa Xaa Ile Xaa Gln Gln
1               5                   10                  15

Asp Phe Val Asn Trp
            20

<210> SEQ ID NO 74
<211> LENGTH: 28
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(28)
<223> OTHER INFORMATION: GIP3-30 (variant); X is independently any amino
      acid

<400> SEQUENCE: 74

Glu Gly Thr Phe Ile Ser Asp Tyr Ser Ile Ala Met Xaa Xaa Ile Xaa
1               5                   10                  15

Gln Gln Asp Phe Val Asn Trp Leu Leu Ala Gln Xaa
            20                  25

<210> SEQ ID NO 75
<211> LENGTH: 27
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(27)
<223> OTHER INFORMATION: GIP4-30 (variant); X is independently any amino
      acid

<400> SEQUENCE: 75

Gly Thr Phe Ile Ser Asp Tyr Ser Ile Ala Met Xaa Xaa Ile Xaa Gln
1               5                   10                  15
```

```
Gln Asp Phe Val Asn Trp Leu Leu Ala Gln Xaa
            20                  25

<210> SEQ ID NO 76
<211> LENGTH: 26
<212> TYPE: PRT
<213> ORGANISM: Artificial sequence
<220> FEATURE:
<223> OTHER INFORMATION: GIP analogues
<220> FEATURE:
<221> NAME/KEY: MISC_FEATURE
<222> LOCATION: (1)..(26)
<223> OTHER INFORMATION: GIP5-30 (variant); X is independently any amino
      acid

<400> SEQUENCE: 76

Thr Phe Ile Ser Asp Tyr Ser Ile Ala Met Xaa Xaa Ile Xaa Gln Gln
1               5                   10                  15

Asp Phe Val Asn Trp Leu Leu Ala Gln Xaa
            20                  25

<210> SEQ ID NO 77
<211> LENGTH: 27
<212> TYPE: PRT
<213> ORGANISM: Homo sapiens

<400> SEQUENCE: 77

Gly Thr Phe Ile Ser Asp Tyr Ser Ile Ala Met Asp Lys Ile His Gln
1               5                   10                  15

Gln Asp Phe Val Asn Trp Leu Leu Ala Gln Lys
            20                  25

<210> SEQ ID NO 78
<211> LENGTH: 26
<212> TYPE: PRT
<213> ORGANISM: Homo sapiens

<400> SEQUENCE: 78

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 79
<211> LENGTH: 28
<212> TYPE: PRT
<213> ORGANISM: Homo sapiens

<400> SEQUENCE: 79

Glu Gly Thr Phe Ile Ser Asp Tyr Ser Ile Ala Met Asp Lys Ile Ala
1               5                   10                  15

Gln Gln Asp Phe Val Asn Trp Leu Leu Ala Gln Lys
            20                  25

<210> SEQ ID NO 80
<211> LENGTH: 28
<212> TYPE: PRT
<213> ORGANISM: Homo sapiens

<400> SEQUENCE: 80

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
```

20          25

<210> SEQ ID NO 81
<211> LENGTH: 28
<212> TYPE: PRT
<213> ORGANISM: Homo sapiens

<400> SEQUENCE: 81

Glu Gly Thr Phe Ile Ser Asp Tyr Ser Ile Ala Met Glu Lys Ile Ala
1               5                   10                  15

Gln Gln Asp Phe Val Asn Trp Leu Leu Ala Gln Lys
            20                  25

<210> SEQ ID NO 82
<211> LENGTH: 28
<212> TYPE: PRT
<213> ORGANISM: Homo sapiens

<400> SEQUENCE: 82

Glu Gly Thr Phe Ile Ser Asp Tyr Ser Ile Ala Met Asp Ala Ile Ala
1               5                   10                  15

Gln Gln Asp Phe Val Asn Trp Leu Leu Ala Gln Lys
            20                  25

<210> SEQ ID NO 83
<211> LENGTH: 28
<212> TYPE: PRT
<213> ORGANISM: Homo sapiens

<400> SEQUENCE: 83

Glu Gly Thr Phe Ile Ser Asp Tyr Ser Ile Ala Met Glu Lys Ile His
1               5                   10                  15

Gln Gln Asp Phe Val Asn Trp Leu Leu Ala Gln Lys
            20                  25

<210> SEQ ID NO 84
<211> LENGTH: 28
<212> TYPE: PRT
<213> ORGANISM: Homo sapiens

<400> SEQUENCE: 84

Glu Gly Thr Phe Ile Ser Asp Tyr Ser Ile Ala Met Asn Lys Ile His
1               5                   10                  15

Gln Gln Asp Phe Val Asn Trp Leu Leu Ala Gln Lys
            20                  25

<210> SEQ ID NO 85
<211> LENGTH: 28
<212> TYPE: PRT
<213> ORGANISM: Homo sapiens

<400> SEQUENCE: 85

Glu Gly Thr Phe Ile Ser Asp Tyr Ser Ile Ala Met Asp Ala Ile His
1               5                   10                  15

Gln Gln Asp Phe Val Asn Trp Leu Leu Ala Gln Lys
            20                  25

<210> SEQ ID NO 86
<211> LENGTH: 28
<212> TYPE: PRT
<213> ORGANISM: Homo sapiens

<400> SEQUENCE: 86

Glu Gly Thr Phe Ile Ser Asp Tyr Ser Ile Ala Met Asp His Ile His
1               5                   10                  15

Gln Gln Asp Phe Val Asn Trp Leu Leu Ala Gln Lys
            20                  25

<210> SEQ ID NO 87
<211> LENGTH: 28
<212> TYPE: PRT
<213> ORGANISM: Homo sapiens

<400> SEQUENCE: 87

Glu Gly Thr Phe Ile Ser Asp Tyr Ser Ile Ala Met Asp Arg Ile His
1               5                   10                  15

Gln Gln Asp Phe Val Asn Trp Leu Leu Ala Gln Lys
            20                  25

<210> SEQ ID NO 88
<211> LENGTH: 28
<212> TYPE: PRT
<213> ORGANISM: Homo sapiens

<400> SEQUENCE: 88

Glu Gly Thr Phe Ile Ser Asp Tyr Ser Ile Ala Met Asp Lys Ile Phe
1               5                   10                  15

Gln Gln Asp Phe Val Asn Trp Leu Leu Ala Gln Lys
            20                  25

<210> SEQ ID NO 89
<211> LENGTH: 28
<212> TYPE: PRT
<213> ORGANISM: Homo sapiens

<400> SEQUENCE: 89

Glu Gly Thr Phe Ile Ser Asp Tyr Ser Ile Ala Met Asp Lys Ile Trp
1               5                   10                  15

Gln Gln Asp Phe Val Asn Trp Leu Leu Ala Gln Lys
            20                  25

<210> SEQ ID NO 90
<211> LENGTH: 28
<212> TYPE: PRT
<213> ORGANISM: Homo sapiens

<400> SEQUENCE: 90

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Arg
            20                  25

<210> SEQ ID NO 91
<211> LENGTH: 28
<212> TYPE: PRT
<213> ORGANISM: Homo sapiens

<400> SEQUENCE: 91

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln His
            20                  25

<210> SEQ ID NO 92

```
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: AMIDATION

<400> SEQUENCE: 92

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 93
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 93

Gly Thr Phe Ile Ser Asp Tyr Ser Ile Ala Met Asp Lys Ile His Gln
1               5                   10                  15

Gln Asp Phe Val Asn Trp Leu Leu Ala Gln Lys
            20                  25

<210> SEQ ID NO 94
<211> LENGTH: 26
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: AMIDATION

<400> SEQUENCE: 94

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25
```